(12) United States Patent
Polansky

(10) Patent No.: US 7,381,526 B2
(45) Date of Patent: Jun. 3, 2008

(54) ASSAYS FOR DRUG DISCOVERY BASED ON MICROCOMPETITION WITH A FOREIGN POLYNUCLEOTIDE

(76) Inventor: Hanan Polansky, 294 Avalon Ct., Rochester, NY (US) 14618

( * ) Notice: Subject to any disclaimer, the term of this patent is extended or adjusted under 35 U.S.C. 154(b) by 380 days.

(21) Appl. No.: 10/211,295

(22) Filed: Aug. 1, 2002

(65) Prior Publication Data

US 2004/0023207 A1  Feb. 5, 2004

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search .................. 435/6; 536/23.1, 24.3
See application file for complete search history.

(56) References Cited

U.S. PATENT DOCUMENTS

| | | | | |
|---|---|---|---|---|
| 5,601,975 A | * | 2/1997 | Bonyhadi et al. | 435/5 |
| 6,060,310 A | * | 5/2000 | Cho-Chung | 435/375 |
| 6,310,197 B1 | * | 10/2001 | Rogers | 536/24.1 |

OTHER PUBLICATIONS

Goodman RH, Smolik S. CBP/p300 in cell growth, transformation, and development. Genes Dev. Jul. 1, 2000;14(13):1553-77.
Hottiger MO, Nabel GJ. Viral replication and the coactivators p300 and CBP. Trends Microbiol. Dec. 2000;8(12):560-5.
Scholer HR, Gruss P. Specific interaction between enhancer-containing molecules and cellular components. Cell. Feb. 1984;36(2):403-11.
Mercola M, Goverman J, Mirell C, Calame K. Immunoglobulin heavy-chain enhancer requires one or more tissue-specific factors. Science. Jan. 18, 1985;227(4684):266-70.
Scholer H, Haslinger A, Heguy A, Holtgreve H, Karin M. In Vivo Competition Between a Metallothionein Regulatory Element and the SV40 Enhancer. Science 1986 232: 76-80.
Cherington V, Brown M, Paucha E, St Louis J, Spiegelman BM, Roberts TM. Separation of simian virus 40 large-T-antigen-transforming and origin-binding functions from the ability to block differentiation. Mol Cell Biol. Mar. 1988;8(3):1380-4.
Adam GI, Miller SJ, Ulleras E, Franklin GC. Cell-type-specific modulation of PDGF-B regulatory elements via viral enhancer competition: a caveat for the use of reference plasmids in transient transfection assays. Gene. Oct. 31, 1996;178(1-2):25-9.
Higgins C, Chatterjee S, Cherington V. The block of adipocyte differentiation by a C-terminally truncated, but not by full-length, simian virus 40 large tumor antigen is dependent on an intact retinoblastoma susceptibility protein family binding domain. J Virol. Feb. 1996;70(2):745-52.
Awazu S, Nakata K, Hida D, Sakamoto T, Nagata K, Ishii N, Kanematsu T. Stable transfection of retinoblastoma gene promotes contact inhibition of cell growth and hepatocyte nuclear factor-1-mediated transcription in human hepatoma cells. Biochem Biophys Res Commun. Nov. 9, 1998;252(1):269-73.
Hofman K, Swinnen JV, Claessens F, Verhoeven G, Heyns W. Apparent coactivation due to interference of expression constructs with nuclear receptor expression. Mol Cell Endocrinol. Oct. 25, 2000;168(1-2):21-9.
Choi SJ, Oba Y, Gazitt Y, Alsina M, Cruz J, Anderson J, Roodman GD. Antisense inhibition of macrophage inflammatory protein 1-alpha blocks bone destruction in a model of myeloma bone disease. J Clin Invest. Dec. 2001;108(12):1833-41.
Hu Z, Garen A. Targeting tissue factor on tumor vascular endothelial cells and tumor cells for immunotherapy in mouse models of prostatic cancer. Proc Natl Acad Sci U S A. Oct. 9, 2001;98(21):12180-5.

* cited by examiner

*Primary Examiner*—Ethan Whisenant

(57) ABSTRACT

A recent discovery showed that microcompetition between a foreign polynucleotide and a cellular polynucleotide is a risk factor for some of the major chronic diseases. The invention uses this novel discovery to present assays for screening compounds based on their effectiveness in modulating such microcompetition. The effective compounds can be used in treatment of these chronic diseases. The invention also presents assays for screening compounds that can be used in treatment of chronic diseases resulting from other foreign polynucleotide-type disruptions.

95 Claims, 6 Drawing Sheets

US 7,381,526 B2

ASSAYS FOR DRUG DISCOVERY BASED ON MICROCOMPETITION WITH A FOREIGN POLYNUCLEOTIDE

BACKGROUND OF THE INVENTION

The cause of many cases of the major chronic diseases is unknown. Therefore, treatment is focused on clinical symptoms associated with the disease rather than the cause. As a result, in many cases, the treatment shows limited efficacy and serious negative side effects.

Recently, the National Cancer Institute (NIH Guide 2000[1]) announced a program aimed to "reorganize the "front-end," or gateway, to drug discovery in cancer. The new approach promotes a three stage discovery process; first, discovery of the molecular mechanisms underlying neoplastic transformations, cancer growth and metastasis; second, selection of a novel molecular target within the discovered biochemical pathway associated with the disease state; finally, design of a new drug that modifies the selected target. The program encourages moving away from screening based on a clinical effects, such as tumor cell shrinkage, either in vivo or in vitro, to screening, or drug design, based on molecular effects. According to the NCI, screening by a desired clinical effect identified drugs that traditionally demonstrated clear limitations in patients, while screening by a desired molecular effect should produce more efficacious and specific drugs.

The best drugs reverse the molecular events that cause a disease. Following the discovery of microcompetition between foreign polynucleoitdes and cellular genes as the cause of many chronic disease cases, the present invention presents methods for treating chronic diseases, methods for evaluating the effectiveness of a compound for use in modulating the progression of chronic diseases, and methods for determining whether a subject has a chronic disease, or has an increased risk of developing clinical symptoms associated with such disease.

BRIEF SUMMARY OF THE INVENTION

In one aspect, the invention presents methods for treating chronic diseases. In a preferred embodiment, the methods feature administration to a subject a therapeutically effective amount of a pharmaceutical or nutraceutical composition that attenuates microcompetition between a foreign polynucleotide and a cellular polynucleotide, attenuates an effect of such microcompetition, or attenuates an effect of another foreign polynucleotide-type disruption. A pharmaceutical or nutraceutical composition may include, but not limited to, small molecule (organic or inorganic), polynucleotide, polypeptide or antibody.

For example, to ameliorate a disease symptom resulting from microcompetition between a foreign polynucleotide and a cellular polynucleotide, a pharmaceutical composition can be administered to the subject that reduces the cellular copy number of the foreign polynucleotide, reduces complex formation between the foreign polynucleotide and a cellular transcription factor, increases complex formation between the microcompeted cellular transcription factor and the cellular polynucleotide, or reverses an effect of microcompetition on the expression or activity of a polypeptide with expression regulated by the cellular polynucleotide. For example, in the case of a p300/cbp virus and the cellular Rb gene, a pharmaceutical composition can be administered to the subject that reduces the copy number of the p300/cbp virus by, for instance, reducing viral replication, reduces binding of a p300/cbp transcription factor, such as GABP, to the p300/cbp virus, increases expression of the p300/cbp transcription factor, increases binding of the p300/cbp transcription factor to the Rb promoter by, for instance, stimulating phosphorylation of the p300/cbp transcription factor, or increases expression of Rb, through, for instance, transfection of an exogenous Rb gene, reduced degradation of the Rb protein, or administration of exogenous Rb protein (see more examples below).

In the case of another foreign polynucleotide-type disruption, for example, the composition may reverse the effects of such disruption. For instance, microcompetition with a p300/cbp virus reduces expression of Rb. A mutation can also reduce the expression of Rb. Therefore, such mutation is a foreign polynucleotide-type disruption. Microcompetition with a p300/cbp virus can result in cancer, and, therefore, a mutation in the Rb promoter that reduces Rb expression can also result in cancer. To ameliorate the symptoms of cancer resulting from such mutation in the Rb gene, a pharmaceutical composition can be administered to the subject that stimulates complex formation between a p300/cbp transcription factor and Rb.

In second aspect, the invention provides assays for screening test compounds to find compounds which modulate microcompetition between a foreign polynucleotide and a cellular polynucleotide, an effect of such microcompetition, or an effect of another foreign polynucleotide-type disruption.

A further aspect of the invention provides methods for determining the risk of developing the molecular, cellular and clinical symptoms associated with a chronic disease. The method may include detecting in a biological sample obtained from a subject at least one of the following: (i) a foreign polynucleotide, specifically, a p300/cbp virus (ii) modified expression or bioactivity of a gene suceptible to microcompetition with a foreign polynuleotide, specifially, a p300/cbp regulated gene (iii) presence of a genetic lesion in a gene suceptible to microcompetition with a foreign polynculetide, specifically, a gene encoding a p300/cbp factor, a p300/cbp regulated gene, p300/cbp factor kinase or p300/cbp phosphatase, or p300/cbp agent (iv) presence of a genetic lesion in a DNA binding box of a p300/cbp transcription factor.

DETAILED DESCRIPTION OF THE INVENTION

A. Introduction of Invention

1. Detailed Description of New Elements

Figure 1:
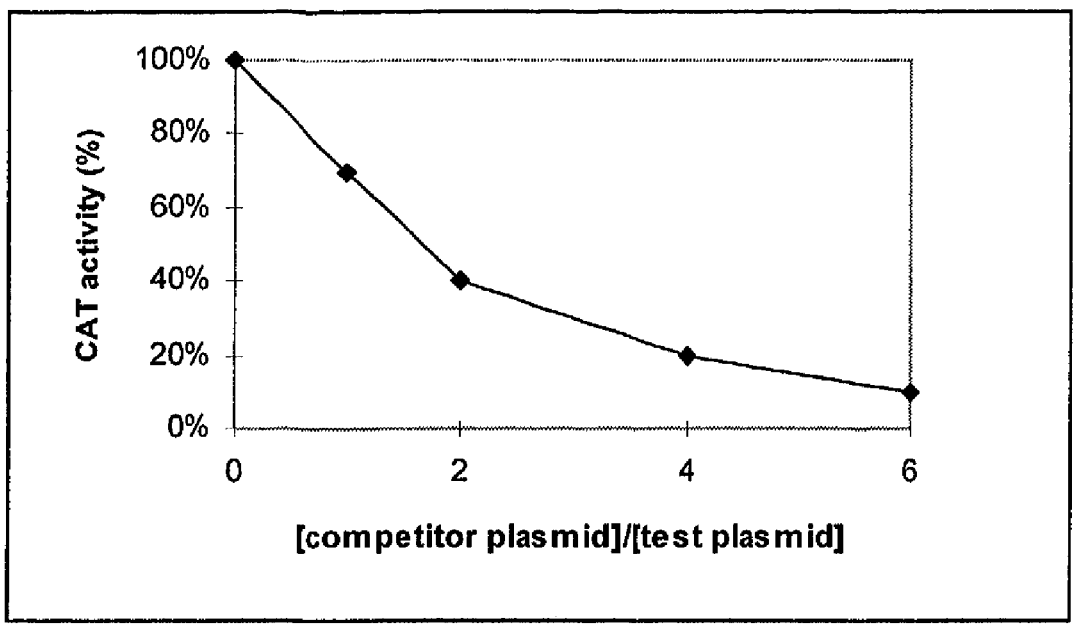
FIG. 1 shows the observed relative CAT activity as a function of the relative concentration of the competitor plasmid pX1.0 to the test plasmid pSV2CAT.

The following sections present descriptions of elements used in the present invention. Following each definition, one or more exemplary assays are provided to illustrate to one skilled in the art how to use the element. Each assay may include, as its own elements, standard methods in molecular biology, microbiology, cell biology, cell culture, transgenic biology, recombinant DNA, immunology, pharmacology, and toxicology, well known in the art. Details of the standard methods are available further below.

a) Microcompetition Related Elements
(1) Microcompetition

Definition

Assume the DNA sequences $DNA_1$ and $DNA_2$ bind the transcription complexes $C_1$ and $C_2$, respectively. If $C_1$ and $C_2$ include the same transcription factor, $DNA_1$ and $DNA_2$ are called "microcompetitors." A special case of microcompetition is two DNA sequences which bind the same transcription complex.

Notes:

1. Transcription factors include transcription coactivators.
2. Sharing the same environment, such as cell, or chemical mix, is not required to be regarded microcompetitors. For instance, two genes which were shown once to bind the same transcription factor are regarded microcompetitors independent of their actual physical environment. To emphasize such independence, the terminology "susceptible to microcompetition" may be used.

Exemplary Assays

1. If $DNA_1$ and $DNA_2$ are endogenous in the cell of interest, assay the transcription factors bound to the DNA sequences (see in "Detailed description of standard protocols" below, the section entitled "Identifying a polypeptide bound to DNA or protein complex") and compare the two sets of polypeptides. If the two sets include a common transcription factor, $DNA_1$ and $DNA_2$ are microcompetitors.

2. In assay 1, if $DNA_1$ and/or $DNA_2$ are not endogenous, introduce $DNA_1$ and/or $DNA_2$ to the cell by, for instance, transfecting the cell with plasmids carrying $DNA_1$ and/or $DNA_2$, infecting the cell with a virus that includes $DNA_1$ and/or $DNA_2$, and mutating endogenous DNA to produce a sequence identical to $DNA_1$ and/or $DNA_2$.

Notes:

1. Introduction of exogenous $DNA_1$ and/or $DNA_2$ is a special case of modifying the cellular copy number of a DNA sequence. Such introduction increases the copy number from zero to a positive number. Generally, copy number may be modified by means such as the ones mentioned above, for instance, transfecting the cell with plasmids carrying a DNA sequence of interest, infecting the cell with a virus that includes the DNA sequence of interest, and mutating endogenous DNA to produce a sequence identical to the DNA sequence of interest.

2. Assume $DNA_1$ and $DNA_2$ microcompete for the transcription factor F. Assaying the copy number of at least one of the two sequences, that is, $DNA_1$ and/or $DNA_2$, is regarded as assaying microcompetition for F, and observing a change in the copy number of at least one of the two sequences is regarded as identification of modified microcompetition for F.

3. Assume the transcription factor F binds the DNA box $DNA_F$. Consider a specific DNA sequence, $DNA_1$ which includes a $DNA_F$ box, then:

$$[F \cdot DNA_1] = f([DNA_F], [F], \text{F-affinity, F-avidity})$$

The concentration of F bound to $DNA_1$ is a function of the $DNA_F$ copy number, the concentration of F in the cell, F affinity and avidity to its box. Using f, a change in microcompetition can be defined as a change in $[DNA_F]$, and a change in $[F \cdot DNA_1]$ as an effect of such change.

4. Note that under certain conditions (fixed [F], fixed F-affinity, fixed F-avidity, and limiting transcription factor (see below)), there is a "one to one" relation between $[F \cdot DNA_1]$ and $[DNA_F]$. Under such conditions, assaying $[F \cdot DNA_1]$ is regarded assaying microcompetition.

Examples

See studies in the section below entitled "Microcompetition with a limiting transcription complex."

(2) Microavailable

Definition

Let $L_1$ and $L_2$ be two molecules. Assume $L_1$ can take s = (1 ... n) shapes. Let $L_{1,s}$ denote $L_1$ in shape s, and let $[L_{1,s}]$ denote concentration of $L_{1,s}$. If $L_{1,s}$ can bind $L_2$, an increase (or decrease) in $[L_{1,s}]$ in the environment of $L_2$ is called "increase (or decrease) in microavailability of $L_{1,s}$ to $L_2$." Microavailability of $L_{1,s}$ is denoted $_{ma}L_{1,s}$. A shape that does not bind $L_2$ is called "microunavailable to $L_2$."

Let s=(1 ... m) denote the set of all $L_{1,s}$ that can bind $L_2$. Any increase (or decrease) in the sum of $[L_{1,s}]$ over all s =

(1 . . . m) is called "increase (or decrease) in microavailability of $L_1$ to $L_2$." Microavailability of $L_1$ to $L_2$ is denoted $_{ma}L_1$.

Figure 6:
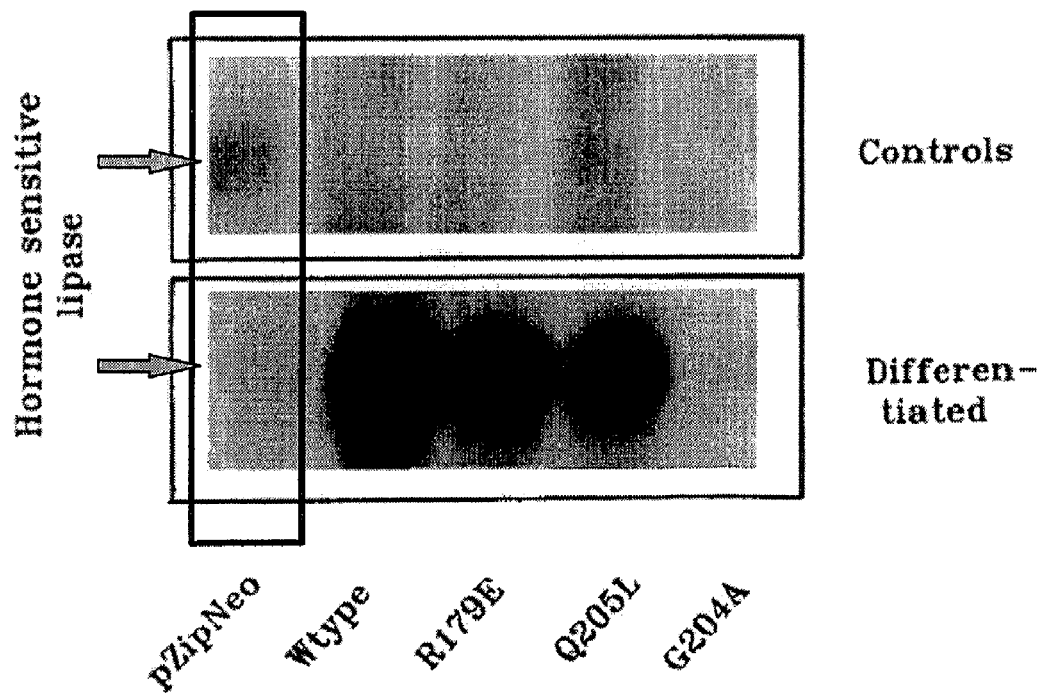
FIG. 6 shows the observed HSL mRNA in undifferentiated confluent controls and in differentiated 3T3-L1 cells transfected with the pZipNeo vector.

Notes:
1. A molecule in a complex is regarded in a different shape relative to the same molecule uncomplexed, or free.
2. Consider an example of an antibody against $L_{1,j}$, a specific shape of $L_1$. Assume the antibody binds $L_{1,j}$ in the region contacting $L_2$. Assume the antibody binds a single region of $L_{1,j}$, and that antibody binding prevents formation of the $L_1 \cdot L_2$ complex. By binding $L_{1,j}$, the antibody changes the shape of $L_1$ from $L_{1,j}$ to $L_{1,k}$ (from exposed to hidden contact region). Since $L_{1,k}$ does not bind $L_2$, the decrease in $[L_{1,j}]$ decreases $_{ma}L_1$, or the microavailability of $L_1$ to $L In another exemplary study by Hottiger 1998[3], the two genes are HIV-CAT, which binds NF-κB, and GAL4-CAT, which binds the fusion protein GAL4-Stat2(TA). NF-κB binds p300/cbp. The GAL4-Stat2(TA) fusion protein includes the Stat2 transactivation domain which also binds p300/cbp. The study showed a close dependent inhibition of gene activation by the transactivation domain of Stat2 following transfection of a RelA expression vector (Hottiger 1998, ibid, FIG. 6A).

5. Transfect F and modify the copy number of $DNA_2$, another DNA sequence, or $G_2$, a another gene, which also bind F (by, for instance, transfecting the cell with $DNA_2$ or $G_2$, see also above). Following transfection:
(a) Assay concentration of F bound to $DNA_1$. Attenuated decrease in concentration of F bound to $DNA_1$ indicates that F is limiting in respect to $DNA_1$.
(b) If DNA1 is the gene $G_1$, assay $G_1$ transcription. Attenuated decrease in $G_1$ transactivation caused by $DNA_2$ or $G_2$, indicates that F is limiting in respect to $G_1$ (see Hottiger 1998, ibid, FIG. 6D).

6. Call the box which binds F the "F-box." Transfect a cell with $DNA_2$, another DNA sequence, or $G_2$, another gene, carrying a wild type F-box. Transfect another cell with with $DNA_2$ or $G_2$, after mutating the F-box in the transfected $DNA_2$ or $G_2$.
(a) Assay the concentration of F bound to $DNA_1$. Attenuated decrease in the concentration of F bound to $DNA_1$ with the wild type but not the mutated F-box indicates that F is limiting in respect to $DNA_1$.
(b) If DNA1 is the gene $G_1$, assay $G_1$ transcription. Attenuated decrease in $G_1$ transactivation with the wild type but not the mutated F-box indicates that F is limiting in respect to $G_1$.

If DNA1 is the gene $G_1$, a mutation in the F-box results in diminished binding of F to $DNA_2$ or $G_2$, and an attenuated inhibitory effect on $G_1$ transactivation. In Kamei 1996 (ibid), mutations in the RAR AF2 domain that inhibit binding of CBP, and other coactivator proteins, abolished AP-1 repression by nuclear receptors.

7. Let $t_1$ and $t_2$ be two transcription factors which bind F. Let $G_1$ and $G_2$ be two genes transactivated by the $t_1 \bullet F$ and $t_2 \bullet F$ complexes, respectively.
(a) Transfect a cell of interest with $t_1$ and assay $G_2$ transcription. If the increase in [$t_1$] reduces transcription of $G_2$, F is limiting in respect to G. Call $t_2 \bullet F$ the microavailable shape of F in respect to $G_2$. The increase in [$t_1$] increases [$t_1 \bullet F$], which, in turn, reduces [$t_2 \bullet F$]. The decrease in the shape of F microavailable to $G_2$ reduces transactivation of $G_2$. In Hottiger 1998 (ibid), $t_1$ is RelA, $t_2$ is GAL4-Stat2(TA) and $G_2$ is GAL4-CAT. See results of the increase in $t_1$ on $G_2$ transactivation shown in Hottiger (1998, ibid) FIG. 6A. (b) Transfect F and assay the concatenation of F bound to G, or transactivation of G. If the increase in F decreases the inhibitory effect of $t_1$, F is limiting in respect to G (see Hottiger 1998 (ibid), FIG. 6C showing the effect of p300/cbp transfection). (c) Assay the concentration of $t_1$, $t_2$ and F. If $t_1$ and $t_2$ have a high molar excess compared to F, F is limiting in respect to G (see Hottiger 1998, (ibid)). (4) Microcompetition for a Limiting Factor Definition Assume $DNA_1$ and $DNA_2$ microcompete for the transcription factor F. If F is limiting in respect to $DNA_1$ and $DNA_2$, $DNA_1$ and $DNA_2$ are called "microcompetitiors for a limiting factor."

Exemplary Assays

1. The assays 4-7 in the section entitled "Limiting transcription factor" above, can be used to identify microcompetition for a limiting factor.
2. Modify the copy number of $DNA_1$ and $DNA_2$ (by, for instance, co-transfecting recombinant vector carrying $DNA_1$ and $DNA_2$, see also above).
(a) Assay DNA, protection against enzymatic digestion ("DNase footprint assay"). A change in protection indicates microcompetition for a limiting factor.
(b) Assay $DNA_1$ electrophoretic gel mobility ("electrophoretic mobility shift assay"). A change in mobility indicates microcompetition for a limiting factor.
3. If $DNA_1$ is a segment of a promoter or enhancer, or can function as a promoter or enhancer, independently, or in combination of other DNA sequences, fuse $DNA_1$ to a reporter gene such as CAT or LUC. Co-transfect the fused $DNA_1$ and $DNA_2$. Assay for expression of the reporter gene. Specifically, assay transactivation of reporter gene following an increase in $DNA_2$ copy number. A change in transactivation of the reporter gene indicates microcompetition for a limiting factor.
4. A special case is when $DNA_1$ is the entire cellular genome responsible for normal cell morphology and function. Transfect $DNA_2$, and assay cell morphology and/or function (such as, binding of extracellular protein, cell replication, cellular oxidative stress, gene transcription, etc). A change in cell morphology and/or function indicates microcompetition for a limiting factor.

Notes:
1. Preferably, following co-transfection of $DNA_1$ and $DNA_2$, verify that the polynucleotides do not produce mRNA. If the sequences transcribe mRNA, block translation of proteins with, for instance, an antisense oligonucleotide specific for the exogenous mRNA. Alternatively, verify that the proteins are not involved in binding of F to either sequence. Also, verify that co-transfection does not mutate the F-boxes in $DNA_1$ and $DNA_2$, and that the sequences do not change the methylation patterns of their F-boxes. Finally, check that $DNA_1$ and $DNA_2$ do not contact each other in the F-box region.

Examples

See studies in the section below entitled "Microcompetition with a limiting transcription complex."
(5) Foreign to Definition 1

Consider an organism R with standard genome O. Consider $O_s$ a segment of O. If a polynucleotide Pn is different from $O_s$ for all $O_s$ in O, Pn is called "foreign to R."

Notes:
1. As an example for different organisms consider the list of standard organisms in the PatentIn 3.1 software. The list includes organisms such as, homo sapiens (human), mus musculus (mouse), ovis aries (sheep), and gallus gallus (chicken).
2. A standard genome is the genome shared by most representatives of the same organism.
3. A polynucleotide and DNA sequence (see above) are interchangeable concepts.
4. In multicellular organism, such as humans, the standard genome of the organism is not necessarily found in every cell. The genomes found in sampled cells can vary as a result of somatic mutations, viral integration, etc (see definition below of foreign polynucleotide in a specific cell).

5. Assume Pn expresses the polypeptide Pp. If Pn is foreign to R, then Pp is foreign to R.

6. When the reference organism is evident, instead of the phrase "a polynucleotide foreign to organism R," the "foreign polynucleotide" phrase might be used.

Exemplary Assays

1. Compare the sequence of Pn with the sequence, or sequences of the published, or self sequenced standard genome of R. If the sequence is not a segment of the standard genome, Pn is foreign to R.

2. Isolate DNA from O (for instance, from a specific cell, or a virus). Try to hybridize Pn to the isolated DNA. If Pn does not hybridize, it is foreign.

Notes:

1. Pn can still be foreign if it hybridizes with DNA from a specific O specimen. Consider, for example, the case of integrated viral genomes. Viral sequences integrated into cellular genomes are foreign. To increase the probability of correct identification, repeat the assay with N>1 specimens of O (for instance, by collecting N cells from different representatives of R). Define the genome of R as all DNA sequences found in all O specimens. Following this definition, integrated sequences which are only segments of certain O specimens are identified as foreign. Note that the test is dependent on the N population. For instance, a colony which propagates from a single cell might include a foreign polynucleotide in all daughter cells. Therefore, the N specimens should include genomes (or cells) from different lineages.

2. A polynucleotide can also be identified as potentially foreign if it is found episomally in the nucleus. If the DNA is found in the cytoplasm, it is most likely foreign. Also, a large enough polynucleotide can be identified as foreign if many copies of the polynucleotide can be observed in the nucleus. Finally, if Pn is identical to sequences in genomes of other organisms, such as viruses or bacteria, known to invade R cells, and specifically nuclei of R cells, Pn is likely foreign to R.

Definition 2

Consider an organism R. If a polynucleotide Pn is immunologically foreign to R, Pn is called "foreign to R."

Notes:

1. In Definition 1, the comparison between O, the genome of the R organism, and Pn is performed logically by the observer. In definition 2, the comparison is performed biologically by the immune system of the organism R.

2. Definition 2 can be generalized to any compound or substance. A compound X is called foreign to organism R, if X is immunologically foreign to R.

Exemplary Assays

1. If the test polynucleotide includes a coding region, incorporate the test polynucleotide in an expressing plasmid and transfer the plasmid into organism R, through, for instance, injection (see DNA-based immunization protocols). An immune response against the expressed polypeptide indicates that the polynucleotide is foreign.

2. Inject the test polynucleotide in R. An immune response against the injected polynucleotide indicates that the test polynucleotide is foreign.

Examples

Many viruses, nuclear, such as Epstein-Barr, and cytoplasmic, such as Vaccinia, express proteins which are antigenic and immunogenic in their respective host cells.

Definition 3

Consider an organism R with standard genome O. Consider Os, a segment of O. If a polynucleotide Pn is chemically or physically different than $O_s$ for all $O_s$ in O, Pn is called "foreign to R."

Notes:

1. In Definition 3, the observer compares O, the genome of the R organism, with Pn using the molecules chemical or physical characteristics.

Exemplary Assays

In general, many assays in the "Detection of a genetic lesion" section below compare a test polynucleotide and a wild-type polynucleotide. In these assay, let $O_s$ be the wild-type polynucleotide and use the assays to identify a foreign polynucleotide. Consider the following examples.

1. Compare the electrophoretic gel mobility of $O_s$ and the test polynucleotide. If mobility is different, the polynucleotides are different.

2. Compare the patterns of restriction enzyme cleavage of $O_s$ and the test polynucleotide. If the patterns are different, the polynucleotides are different.

3. Compare the patterns of methylation of $O_s$ and the test polynucleotide (by, for instance, electrophoretic gel mobility). If the patterns are different, the polynucleotides are different.

Definition 4

Consider an organism R with standard genome O. Let [Pn] denote the copy number of Pn in O. Consider a cell $Cell_i$. Let $[Pn]_i$ denote the copy number of Pn in $Cell_i$. If $[Pn]_i > [Pn]$, Pn is called "foreign to $Cell_i$."

Note

1. $[Pn]_i$ is the copy number of all Pn in $Cell_i$, from all sources. For instance, [Pn] includes all Pn segments in O, all Pn segments of viral DNA in the cell (if available), all Pn segments of plasmid DNA in the cell (if available), etc.

1. If [Pn]=0, the definition is identical to definition 1 of foreign polynucleotide.

Exemplary Assays

1. Sequence the genome of $Cell_i$. Count the number of time Pn appears in the genome. Compare the result to the number of times Pn appears in the published standard genome. If the number is greater, Pn is foreign to $Cell_i$.

2. Sequence the genome of $Cell_i$ and a group of other cells $Cell_j, \ldots, Cell_{j+m}$. If $[Pn]_i > [Pn]_j = \ldots = [Pn]_{j+m}$, Pn is foreign to $Cell_i$.

(6) Natural to

Definition

Consider an organism R with standard genome O. If a polynucleotide Pn is a fragment of O, Pn is called "natural to R."

Notes:

1. "Natural to" and "foreign to" are mutually exclusive. A polynucleotide cannot be both foreign and natural to R. If a polynucleotide is natural, it is not foreign to R, and if a polynucleotide is foreign, it is not natural to R.

2. If Pn is a gene natural to R, then, the its gene product is also natural to R.

3. The products of a reaction carried out in a cell between gene products natural to the cell, under normal conditions, are natural to the cell. For instance, cellular splicing by factors natural to the cell produce splice products natural to the cell.

Exemplary Assays

1. Compare the sequence of Pn with the sequence, or sequences of the published, or self sequenced standard genome of R. If the sequence is a segment of the standard genome, Pn is natural to R.

2. Isolate DNA from O (for instance, from a specific cell, or a virus). Try to hybridize Pn to the isolated DNA. If Pn hybridizes, it is natural.

Notes:

1. Hybridization with DNA from a specific O specimen of R is not conclusive evidence that Pn is natural to R. Consider, for example, the case of integrated viral genomes. Viral sequences integrated into cellular genomes are foreign. To increase the probability of correct identification, repeat the assay with N>1 specimens of O (for instance, by collecting N cells from different representatives of R). Define the genome of R as all DNA sequences found in all O specimens. Following this definition, integrated sequences which are only segments of certain O specimens are identified as foreign. Note that the test is dependent on the N population. For instance, a colony which propagates from a single cell might include a foreign polynucleotide in all daughter cells. Therefore, the N specimens should include genomes (or cells) from different lineages.

(7) Empty Polynucleotide

Definition

Consider the Pn polynucleotide. Consider an organism R with genome $O_R$ Let Pp(Pn), and Pp($O_R$) denote a gene product (polypeptide) of a Pn or $O_R$ gene, respectively. If Pp(Pn)≈Pp($O_R$) for all Pp(Pn), Pn will be called an "empty polynucleotide" in respect to R.

Notes:

1. A vector is a specific example of a polynucleotide.

2. A vector that includes a non coding polynucleotide natural to R is considered empty in respect to the R. ("natural to" is the opposite of "foreign to." Note: A natural polynucleotide means, a polynucleotide natural to at least one organism. An artificial polynucleotide means a polynucleotide foreign to all known organisms. A viral enhancer is a natural polynucleotide. A plasmid with a viral enhancer fused to a human gene is artificial.)

3. A vector that includes a coding gene natural to Q, an organism different from R, can still be considered empty in respect to R. For instance, a vector that includes the bacterial chloramphenicol transacetylase (CAT), bacterial neomycin phosphotransferase (neo), or the firefly luciferase (LUC) as reporter genes, but no human coding gene is considered empty in respect to the humans if it does not express a gene natural to humans.

Exemplary Assays

1. Identify all gene products encoded by Pn. Compare to the gene products of $O_R$. If all gene products are different, Pn is considered empty in respect to the R.

Examples pSV2CAT, which expresses the chloramphenicol acethyltransferase (CAT) gene under the control of the SV40 promoter/enhancer, pSV2neo, which expresses the neo gene under the control of the SV40 promoter/enhancer, HSV-neo, which expresses the neomycin-resistance gene under control of the murine Harvey sarcoma virus long terminal repeat (LTR), pZIP-Neo, which expresses the neomycin-resistant gene under control of the Moloney murine leukemia virus long terminal repeat (LTR), are considered empty polynucleotides, or empty vectors, in respect to humans and in respect to the respective virus. See more examples below.

Note: These vectors can be considered as "double" empty, empty in respect to humans, and empty in respect to the respective virus.

(8) Latent Foreign Polynucleotide

Definition

Consider Pn, a polynucleotide foreign to organism R. Pn will be called latent in a $Cell_i$ of R if over an extended period of time, either:

1. Pn produces no Pn transcripts.

2. Denote the set of gene products expressed by Pn in $Cell_i$ with $Cell_i\_Pp(Pn)$ and the set of all possible gene products of Pn with All_Pp(Pn), then, $Cell_i\_Pp(Pn) \subset All\_Pp(Pn)$, that is, the set of Pn gene products expressed in $Cell_i$ is a subset of all possible Pn gene products.

3. Pn shows limited or no replication.

4. Pn is undetected by the host immune system.

5. $Cell_i$ shows no lytic symptoms.

6. R shows no macroscopic symptoms.

Notes:

1. A virus in a host cell is a foreign polynucleotide. According to the definition, a virus is considered latent if, over an extended period of time, it either shows partial expression of its gene products, no viral mRNA, limited or no replication, is undetected by the host immune system, causes no lytic symptoms in the infected cell, or causes no macroscopic symptoms in the host.

2. The above list of characterizations is not exhaustive. The medical literature includes more aspects of latency that can be added to the definition.

Exemplary Assays

1. Introduce, or identify a foreign polynucleotide in a host cell. Assay the polynucleotide replication, or transcription, or mRNA, or gene products over an extended period of time. If the polynucleotide shows limited replication, no transcription, or a limited set of transcripts, the polynucleotide is latent.

2. Introduce, or identify a foreign polynucleotide in a host cell. Assay the cell over an extended period of time, if the cell shows no lytic symptoms, the polynucleotide is latent.

Examples

Using PCR, a study (Gonelli 2001[4]) observed persistent presence of viral human herpes virus 7 (HHV-7) DNA in biopsies from 50 patients with chronic gastritis. The study also observed no U14, U17/17, U31, U42 and U89/90, HHV-7 specific transcripts highly expressed during replication. Based on these observations, the study concluded that "gastric tissue represents a site of HHV-7 latent infection and potential reservoir for viral reactivation." To test the effect of treatment on the establishment of latent herpes simplex virus, type 1 (HSV-1) in sensory neurons, another study (Smith 2001[5]) assays the expression of the latency-associated transcript (LAT), the only region of the viral genome transcribed at high levels during the period of viral latency. A recent review (Young 2000[6]) discusses the limited sets of Epstein-Barr viral (EBV) gene products expressed during the period of viral latency.

(9) Partial Description

Definition

Let $C_i$ be a characteristic of a system. Let the set Ci, i= (1 . . . m) be the set of characteristics providing a complete description of the system. Any subset of Ci, i=(1 . . . m) is called a "partial description" of the system.

Exemplary Assays

1. Chose any set of characteristics describing the system and assay these characteristics.

Examples

Assaying blood pressure, blood triglycerides, glucose tolerance, body weight, etc.

(10) Equilibrium

Definition

If a system persists in a state $St_0$ over time, $St_0$ is called equilibrium.

Note:

The system related definitions can be modified to accommodate partial descriptions. For example, consider a description of a system which includes only a proper subset of Ci, i=(1 . . . m). If the values measured for the subset of characteristics in $St_0$ persist over time, the probability that $St_0$ is an equilibrium is greater than zero. However, since the values are measured only on a subset of Ci, i=(1 . . . m), the probability is less than 1. Overall, an increase in the size of the subset of characteristics increases the probability.

Exemplary Assays

1. Assay the values of the complete (sub) set of the system characteristics. Repeat the assays over time. If the values persist, the system is (probably) in equilibrium.

Examples

Regular physicals include standard tests, such as blood count, cholesterol levels, HDL cholesterol, triglycerides, kidney function tests, thyroid function tests, liver function tests, minerals, blood sugar, uric acid, electrolytes, resting electrocardiogram, an exercise treadmill test, vision testing, and audiometry. When the values in these tests remain within a narrow range over time, the medical condition of the subject can be labeled as a probable equilibrium. Other tests performed to identify deviations from equilibrium are mammograms and prostate cancer screenings.

(11) Stable Equilibrium

Definition

Consider an equilibrium $E_0$. If, after small disturbances, the system always returns to $E_0$, the equilibrium is called "stable." If the system moves away from $E_0$ after small disturbances, the equilibrium is called "unstable."

Exemplary Assays

1. Take a biological system (e.g., cell, whole organism, etc). Assay a set of characteristics. Verify that the system is in equilibrium, that is, the values of these characteristics persist over time. Apply treatment to the system and assay the set of characteristics again. Repeat assaying over time. If the treatment changed the values of the characteristics, and within a reasonable time the values returned to the original levels, the equilibrium is stable.

(12) Chronic Disease

Definition

Let a healthy biological system be identified with a certain stable equilibrium. A stable equilibrium different from the healthy system equilibrium is called "chronic disease."

Notes:

1. In chronic disease, in contrast to acute disease, the system does not return to the healthy equilibrium on its own.

Exemplary Assays

1. Take a biological system (e.g., cell, whole organism, etc). Assay a set of characteristics. Compare the results with the values of the same characteristics in healthy controls. If some values deviate from the values of healthy controls, and the values continue to deviate over time, the equilibrium of the system can be characterizes as chronic disease.

Examples

High blood pressure, high body weight, hyperglycemia, etc.

(13) Disruption

Definition

Let a healthy biological system be identified with a certain stable equilibrium. Any exogenous event which produces a new stable equilibrium is called "disruption."

Notes:

1. Using the above definitions it can be said that a disruption is an exogenous event that produces a chronic disease.

2. A disruption is a disturbance with a persisting effect.

Exemplary Assays

1. Take a biological system (e.g., cell, whole organism, etc). Assay a set of characteristics. Compare the results with the values of the same characteristics in healthy controls. Verify that the system is in healthy equilibrium. Apply a chosen treatment to the system. Following treatment, assay the same characteristics again. If some values deviate from the values of healthy controls, continue to assay these characteristics over time. If the values continue to deviate over time, the treatment produced a chronic disease, and, therefore, can be considered a disruption.

Examples

Genetic knockout, carcinogens, infection with persistent viruses (e.g., HIV, EBV), etc.

(14) Foreign Polynucleotide-type Disruption (Cause of Disruption)

Definition

Let Pp be a polypeptide. Assume microcompetition with a foreign polynucleotide Pn directly, or indirectly reduces (or increases) Pp bioactivity. A disruption that directly, or indirectly reduces (or increases) Pp bioactivity is called "foreign polynucleotide-type disruption."

Notes:

1. The first "indirectly" in the definition means that Pp can be downstream from the gene microcompeting with Pn. The second "indirectly" means that Pp can be downstream from the gene, or polypeptide, directly affected by the exogenous event. According to the definition, if both microcompetition with a foreign polynucleotide and an exogenous event increase, or both decrease bioactivity of Pp, the exogenous event can be considered as a foreign polynucleotide-type disruption.

2. Microcompetition with a foreign polynucleotide is a special case of foreign polynucleotide-type disruption.

3. Treatment is a special case of an exogenous event.

4. A foreign polynucleotide-type disruption can first affect a gene or a polypeptide. For instance, a mutation is an effect on a gene. Excessive protein phosphorylation is an effect on a polypeptide.

Exemplary Assays

1. Take a biological system (e.g., cell, whole organism, etc). Assay a set of characteristics. Compare the results with the values of the same characteristics in healthy controls to verify that the system is in a healthy equilibrium. Modify the copy number of Pn, a polynucleotide of interest (by, for instance, transfection, infection, mutation, etc, see above). Identify a gene with modified expression. Assume the assays show decreased expression of G. Take another specimen of the system in healthy equilibrium and apply a chosen treatment to the healthy specimen. Following treatment, assay G expression. Continue to assay G expression over time. If G expression is persistently decreased, the exogenous event can be considered a foreign polynucleotide-type disruption.

Examples

A mutation in the leptin receptor, a mutation in the leptin gene, etc (see more examples below).

(15) Disrupted (Gene, Polypeptide) (Result of Disruption)

Definition

Let Pp be a polypeptide. If a foreign polynucleotide-type disruption modifies (reduces or increases) Pp bioactivity, Pp and the gene encoding Pp are called "disrupted."

Notes:

1. Pp can be downstream from G, the microcompeted gene.

Exemplary Assays

1. Take a biological system (e.g., cell, whole organism, etc). Modify the copy number of Pn, a polynucleotide of interest, (by, from instance, transfection, infection, mutation, etc, see above). Assay bioactivity of genes and polypeptides in the treated system and controls to identify genes and polypeptides with modified bioactivity relative to controls. These genes and polypeptides are disrupted.

Examples

See studies in the section below entitled "Microcompetition with a limiting transcription complex." See also all GABP regulated genes below.

(16) Disrupted Pathway

Definition

Let the polypeptide $Pp_x$ be disrupted. A polypeptide $Pp_i$ which functions downstream or upstream of $Pp_x$, and the gene encoding $Pp_i$, are considered a polypeptide and gene, respectively, in a $Pp_x$ "disrupted pathway."

Exemplary Assays

1. Take a biological system (e.g., cell, whole organism, etc). Apply a treatment to the system that modifies $Pp_i$ bioactivity. Assay $Pp_x$ bioactivity. If the bioactivity of $Pp_x$ changed, $Pp_i$ is in a $Pp_x$ disrupted pathway.

2. Take a biological system (e.g., cell, whole organism, etc). Apply a treatment to the system that modifies $Pp_x$ bioactivity. Assay $Pp_i$ bioactivity. If the bioactivity of $Pp_i$ changed, $Pp_i$ is in a $Pp_x$ disrupted pathway.

Examples

See examples below.

(17) Disruptive Pathway

Definition

Consider a polypeptide $Pp_k$ and a foreign polynucleotide Pn. If a change in bioactivity of $Pp_k$ increases or decreases Pn copy number, $Pp_k$ and the gene encoding $Pp_k$ are considered a polypeptide and a gene in a Pn "disruptive pathway."

Notes:

Consider, as an example, microcompetition between a cell and a viral polynucleotide, including the entire viral genome. $Pp_k$ can be any viral or cellular protein which increase or decreases viral replication.

Exemplary Assays

1. Take a biological system (e.g., cell, whole organism, etc). Apply a treatment to the system that modifies $Pp_k$ bioactivity, for instance, by increasing expression of a foreign or cellular gene encoding $Pp_k$. Assay Pn copy number. If the copy number changed, $Pp_k$ and the gene encoding $Pp_k$, are in a Pn disruptive pathway.

Examples

Consider a GABP virus. The viral proteins which increase viral replication increase the copy number of viral N-boxes in infected cells. According to the definition, these proteins belong to a disruptive pathway. See specific examples below.

b) p300/cbp Related Elements (1) p300/cbp

Definition

A member of the p300/cAMP response element (CREB) binding protein (CBP) family of proteins is called p300/cbp.

Notes:

1. For reviews on the p300/cbp family of proteins, see, for instance, Vo 2001[7], Blobel 2000[8], Goodman 2000[9], Hottiger 2000[10], Giordano 1999[11], Eckner 1996[12].

2. CREB binding protein (CBP, or CREBBP) is also called RTS, Rubinstein-Taybi syndrome protein, and RSTS.

3. See sequences of p300/cbp genes and p300/cbp proteins in the List of Sequences below.

Exemplary Assays 1. p300/cbp may be identified using antibodies in binding assays, oligonucleotide probes in hybridization assays, transcription factors such as GABP, NF-κB, E1A in binding assays, etc. (see protocols for binding and hybridization assays below).

Examples

See examples of below.

(2) p300/cbp Polynucleotide

Definition

Assume the polynucleotide Pn binds the transcription complex C. If C contains p300/cbp, Pn is called "p300/cbp polynucleotide."

Exemplary Assays

1. Take a cell of interest. Modify the copy number of Pn (by, for instance, transfection, infection, mutation, etc, see also above). Use assays described in the section entitled "Identifying a polypeptide bound to DNA or protein complexes," or similar assays, to test if the protein-Pn complexes contain p300/cbp.

2. See more assays below.

Examples

See below in p300/cbp virus and p300/cbp regulated gene.

(3) p300/cbp Factor

Definition

Assume the transcription factor F binds the complex C. If C contains p300/cbp, F is called "p300/cbp factor."

Exemplary Assays

1. Use assays describe in the section entitled "Identifying a polypeptide bound to DNA or protein complexes," or similar assays, to test whether the complexes which contain F also contain p300/cbp.

Examples

The following table lists some cellular and viral p300/cbp factors.

| p300/cbp factor | Gene symbol | Other names | References |
|---|---|---|---|
| Cellular | | | |
| AML1 | RUNX1<br>CBFA2<br>AML1 | acute myeloid leukemia 1 protein (AML1); core-binding factor α2 subunit (CBFα2); oncogene AML-1; Polyomavirus enhancer binding protein 2αB subunit (PEBP2αB); PEA2αB; SL3-3 enhancer factor 1, αB subunit; SL3/AKV core-binding factor αB subunit; SEF1; runt-related transcription factor 1; RUNX1; CBFA2 | Kitabayashi 1998[13] |
| A-Myb | MYBL1<br>AMYB | Myb-related protein A; v-myb avian myeloblastosis viral oncogene homolog-like 1 | Facchinetti 1997[14] |
| ATF1 | ATF1<br>TREB36 | activating transcription factor 1 (ATF1); TREB36 protein; cAMP-dependent transcription factor ATF-1 | Goodman 2000 (ibid) |
| ATF2 | ATF2<br>CREB2<br>CREBP1 | Activating transcription factor 2 (ATF2); cAMP response element binding protein 1 (CRE-BP1); HB16; cAMP-dependent transcription factor ATF-2; TREB7; CREB2 | Goodman 2000 (ibid), Dunyndam 1999[15] |
| ATF4 | ATF4<br>CREB2<br>TAXREB67 | activating transcription factor 4 (ATF4); DNA-binding protein TAXREB67; tax-responsive enhancer element B67 | Goodman 2000 (ibid), Yukawa 1999[16] |

| p300/cbp factor | Gene symbol | Other names | References |
|---|---|---|---|
| | | (TAXREB67); TXREB; cAMP response element-binding protein 2 (CREB2); cAMP-dependent transcription factor ATF-4; CCAAT/enhancer binding protein related activating transcription factor (mouse); ApCREB2 (Aplysia) | |
| BRCA1 | BRCA1 PSCP | Breast cancer type 1 susceptibility protein (BRCA1) | Goodman 2000 (ibid) |
| C/EBPβ | CEBPB TCF5 | CCAAT/enhancer binding protein β (C/EBPβ); nuclear factor NF-IL6 (NFIL6); transcription factor 5; CRP2; LAP; IL6DBP; CEBPB; TCF5 | Goodman 2000 (ibid), Mink 1997[17] |
| c-Fos | FOS G0S7 | proto-oncogene protein c-fos; cellular oncogene fos; G0/G1 switch regulatory protein 7; v-fos FBJ murine osteosarcoma viral oncogene homolog; FOS; G0S7 | Goodman 2000 (ibid), Sato 1997 (ibid) |
| C2TA | MHC2TA CIITA C2TA | MHC class II transactivator; MHC2TA; CIITA | Goodman 2000 (ibid), Sisk 2000 (ibid) |
| AP1 | JUN | transcription factor AP-1; proto-oncogene c-Jun (c-Jun); p39; v-jun avian sarcoma virus 17 oncogene homolog | Goodman 2000 (ibid), Hottiger 2000 (ibid) |
| c-Myb | MYB | Myb proto-oncogene protein; MYB; v-myb avian myeloblastosis viral oncogene homolog | Goodman 2000 (ibid), Hottiger 2000 (ibid) |
| CREB | CREB1 | cAMP-respone-element-binding protein (CREB) | Hottiger 2000 (ibid) |
| CRX | CRX CORD2 CRD | cone-rod homeobox (CRX); CRD; cone rod dystrophy 2 (CORD2) | Yanagi 2000[18] |
| CID | CI-D | cubitus interruptus dominant (CID) | Goodman 2000 (ibid) |
| DBP | DBP | D-site binding protein (DBP); albumin D box-binding protein; D site of albumin promoter (albumin D-box) binding protein; TAXREB302 | Lamprecht 1999[19] |
| E2F1 | E2F1 RBBP3 | retinoblastoma binding protein 3 (RBBP-3); PRB-binding protein E2F-1; PBR3; retinoblastoma-associated protein 1 (RBAP-1) | Goodman 2000 (ibid) Marzio 2000 |
| E2F2 | E2F2 | transcription factor E2F2 | Marzio 2000 (ibid) |
| E2F3 | E2F3 KIAA0075 | transcription factor E2F3; KIAA0075 | Marzio 2000 (ibid) |
| Egr1 | EGR1 ZNF225 | early-growth response factor-1 (Egr1); Krox-24 protein; ZIF268; nerve growth factor-induced protein A; NGFI-A; transcription factor ETR103; zinc finger protein 225 (ZNF225); AT225; TIS8; G0S30; ZIF-268 | Silverman 1998[21] |
| ELK1 | ELK1 | ets-domain protein ELK-1 | Hottiger 2000 (ibid) |
| ERα | ESR1 NR3A1 ESR | estrogen receptor α (ERα); estrogen receptor 1; estradiol receptor | Kim 2001[22], Wang 2001[23], Speir 2000[24], Hottiger 2000 (ibid) |
| ERβ | ESR2 NR3A2 ESTRB | estrogen receptor β; ESR2; NR3A2; ESTRB | Kobayashi 2000[25] |
| ER81 | | Ets translocation variant 1 (ETV1) | Papoutsopoulou 2000[26] |
| Ets1 | ETS1 | C-ets-1 protein; v-ets avian erythroblastosis virus E2 oncogene homolog 1; p54 | Goodman 2000 (ibid), Jayaraman 1999[27] |
| Ets2 | ETS2 | C-ets-2 protein; human erythroblastosis virus oncogene homolog 2; v-ets avian erythroblastosis virus E2 oncogene homolog 2 | Jayaraman 1999 (ibid) |
| GABPα | GABPA E4TF1A | GA binding protein, α subunit (GABPA); GABP-alpha subunit; transcription factor E4TF1-60; nuclear respiratory factor-2 subunit alpha (NRF-2A) | Bannert 1999[28] |

-continued

| p300/cbp factor | Gene symbol | Other names | References |
|---|---|---|---|
| GABPβ1 | GABPB1 GABPB E4TF1B | GA binding protein beta-1 chain (GABPB1); GABP-beta-1 subunit; transcription factor E4TF1-53; nuclear respiratory factor-2 subunit beta 2 (NRF-2B) | Bannert 1999 (ibid) |
| GABPβ2 | GABPB1 GABPB E4TF1B | GA binding protein beta-2 chain (GABPB2); GABP-beta-2 subunit; transcription factor E4TF1-47 | Bannert 1999 (ibid) |
| GATA1 | GATA1 GF1 ERYF1 NFE1 | globin transcription factor 1; GATA-binding protein 1 erythroid transcription factor; ERYF1; GF1; NF-E1 | Goodman 2000 (ibid) |
| Gli3 | GLI3 | zinc finger protein GLI3; PAP-A; GCPS; GLI-Kruppel family member GLI3 (Greig cephalopolysyndactyly syndrome); Pallister-Hall syndrome (PHS) | Goodman 2000 (ibid) |
| GR | NR3C1 GRL GCR | glucocorticoid receptor (GR); nuclear receptor subfamily 3, group C, member 1 (NR3C1); GRL | Pfitzner 1998 (ibid), Hottiger 2000 (ibid) |
| HIF1α | HIF1A | hypoxia-inducible factor-1 α (HIF1α); ARNT interacting protein; member of PAS protein 1; MOP1 | Goodman 2000 (ibid), Bhattacharya 1999[29], Kallio 1998[30], Ema 1999[31], Hottiger 2000 (ibid) |
| HNF4α | HNF4A NR2A1 TCF14 HNF4 | heaptocyte nulcear factor-1 α; HNF-4-α; transcription factor HNF-4; transcription factor 14; MODY; maturity onset diabetes of the young 1; MODY1; HNF4A; NR2A1; TCF14; HNF | Goodman 2000 (ibid), Soutoglou 2000[32] |
| IRF-3 | IRF3 | interferon regulatory factor-3 (IRF-3) | Goodman 2000 (ibid), Yoneyama 1998[33] |
| JunB | JUNB | transcription factor JunB; proto-oncogene JunB | Goodman 2000 (ibid) |
| Mdm2 | MDM2 | mouse double minute 2; human homolog of p53-binding protein (Mdm2); ubiquitin-protein ligase E3 Mdm2; EC 6.3.2.-; p53-binding protein Mdm2; oncoprotein Mdm2; double minute 2 protein; Hdm2 | Goodman 2000 (ibid) |
| MEF2C | MEF2C | myocyte enhancer factor 2C (MEF2C); myocyte-specific enhancer factor 2C; MADS box transcription enhancer factor 2 polypeptide C | Sartorelli 1997 (ibid) |
| Mi | MITF | microphthalmia-associated transcription factor | Goodman 2000 (ibid), Sato 1997[34] |
| MyoD | MYOD1M YF3 | myoblast determination protein 1 (MyoD); myogenic factor MYF-3; myogenic factor 3; PUM | Yuan 1996 Ref, Sartorelli 1997[35] |
| NF-AT1 | NFAT1 NFATC2 NFATP | nuclear factor of activated T cells, cytoplasmic 2; T cell transcription factor NFAT1; NFAT pre-existing subunit; NF-ATp | Garcia-Rodriguez 1998[36], Sisk 2000[37] |
| NF-YB | NFYB HAP3 | NF-Y protein chain B (NF-YB); nuclear transcription factor Y subunit beta; α-CP1, CP1; CCAAT-binding transcription factor subunit A (CBF-A); CAAT-box DNA binding protein subunit B | Li 1998[38], Faniello 1999[39] |
| NF-YA | NFYA HAP2 | NF-Y protein chain A (NF-YA); CCAAT-binding transcription factor subunit B (CBF-B); CAAT-box DNA binding protein subunit A; nuclear transcription factor Y α | Li 1998 (ibid) |
| RelA | RELA NFKB3 | NF-κB RelA, transcription factor p65; nuclear factor NF-kappa-B, p65 subunit; v-rel avian reticuloendotheliosis viral oncogene homolog A; nuclear factor of kappa light polypeptide gene enhancer in B-cells 3 (p65) | Hottiger 1998[40], Gerritsen 1997[41], Speir 2000[42], Hottiger 2000 (ibid) |
| P/CAF | P/CAF | p300/cbp-associated factor | Goodman 2000 (ibid) |
| p/CIP | TRAM-1 NCOA3 AIB1 | p300/cbp interacting protein (p/CIP); thyroid hormone receptor activator molecule; DJ1049g16.2; nuclear receptor coactivator 3 (thyroid hormone receptor | Goodman 2000 (ibid) |

-continued

| p300/cbp factor | Gene symbol | Other names | References |
|---|---|---|---|
| | | activator molecule TRAM-1; receptor-associated coactivator RAC3; amplified in breast cancer AIB1; ACTR | |
| PPARγ | PPARG NR1C3 | peroxisome proliferator activated receptor γ (PPARG); PPAR-gamma; PPARG1; PPARG2 | Iannone 2001[43], Kodera 2000[44] |
| MRG1 | CITED2 MRG1 | Cbp/p300-interacting transactivator 2; MSG-related protein 1; melanocyte-specific gene 1; MRG1 protein | Bhattacharya 1999 (ibid), Han 2001[45] |
| p45 NF-E2 | NFE2 | nuclear factor, erythroid-derived 2 45 kDa subunit; NF-E2 45 kDa subunit (p45 NF-E2); leucine zipper protein NF-E2 | Goodman 2000 (ibid) |
| p53 | TP53 P53 | cellular tumor antigen p53; tumor suppressor p53;, phosphoprotein p53; Li-Fraumeni syndrome | Goodman 2000 (ibid), Avantaggiati 1997[46] Van Order 1999[47], Hottiger 2000 (ibid) |
| p73 | TP73 P73 | tumor protein p73; p53-like transcription factor; p53-related protein | Goodman 2000 (ibid) |
| Pit-1 | POU1F1 PIT1 GHF1 | pituitary-specific positive transcription factor 1; PIT-1; growth hormone factor 1, GHF-1; POU domain, class 1, transcription factor 1 | Goodman 2000 (ibid) |
| RSK1 | RPS6KA1 RSK1 | 90-kDA ribosomal S6 kinase, ribosomal protein S6 kinase alpha 1; EC 2.7.1.-; S6K-alpha 1; 90 kDa ribosomal protein S6 kinase 1; p90-RSK1;, ribosomal S6 kinase 1; RSK-1; pp90RSK1; HU-1 | Goodman 2000 (ibid), Hottiger 2000 |
| RSK3 | RPS6KA2 RSK3 | Ribosomal protein S6 kinase alpha 2; EC 2.7.1.-; S6K-alpha 2; 90 kDa ribosomal protein S6 kinase 2;, p90-RSK 2; ribosomal S6 kinase 3; RSK-3; pp90RSK3; HU-2 | Hottiger 2000 (ibid) |
| RSK2 | RPS6KA3 RSK2 ISPK1 | ribosomal protein S6 kinase alpha 3; EC 2.7.1.-; S6K-alpha 3; 90 kDa ribosomal protein S6 kinase 3; p90-RSK 3; ribosomal S6 kinase 2; RSK-2; pp90RSK2; Insulin-stimulated protein kinase 1; ISPK-1; HU-2;, HU-3 | Hottiger 2000 (ibid) |
| RARγ | RARG NR1B3 | retinoic acid receptor γ (RARγ); retinoic acid receptor gamma-1, RAR-gamma-1; RARC; retinoic acid receptor gamma-2; RAR-gamma-2 | Hottiger 2000 (ibid), Yang 2001 (ibid) |
| RNA helicase A | DDX9 NDH2 | ATP-dependent RNA helicase A; nuclear DNA helicase II (NDH II); DEAD-box protein 9; leukophysin (LKP) | Goodman 2000 (ibid) |
| RXRα | RXRA NR2B1 | retinoic acid receptor RXR-α | Goodman 2000 (ibid), Yang 2001 (ibid) |
| ELK4 | ELK4 SAP1 | ETS-domain protein ELK-4; serum response factor accessory protein 1 (SAP-1); SRF accessory protein 1 | Goodman 2000 (ibid), Hottiger 2000 (ibid) |
| SF-1 | NR5A1 FTZF1 AD4BP SF1 | steroidogenic factor 1 (STF-1, SF-1); steroid hormone receptor AD4BP; Fushi tarazu factor (Drosophila) homolog 1; FTZ1; ELP; NR5A1 (nuclear receptor subfamily 5, group A, member 1) | Goodman 2000 (ibid) |
| Smad3 | MADH3 SMAD3 MAD3 | mothers against decapentaplegic (Drosophila) homolog 3 (SMAD 3); mothers against DPP homolog 3; Mad3; hMAD-3; mMad3; JV15-2; hSMAD3 | Goodman 2000 (ibid), Janknecht 1998[49], Feng 1998[50], Pouponnot 1998 (ibid) |
| Smad4 | MADH4 SMAD4 DPC4 | mothers against decapentaplegic (Drosophila) homolog 4 (SMAD 4); mothers against DPP homolog 4; deletion target in pancreatic carcinoma 4, hSMAD4 | de Caestecker[51], Pouponnot 1998 (ibid) |
| Smad1 | MADH1 SMAD1 MADR1 BSP1 | mothers against decapentaplegic (Drosophila) homolog 1 (SMAD 1); mothers against DPP homolog 1; Mad-related protein 1; transforming growth factor-beta signaling protein-1; BSP-1; hSMAD1; JV4-1 | Pearson 1999[52], Pouponnot 1998 (ibid) |
| Smad2 | MADH2 SMAD2 MADR2 | mothers against decapentaplegic (Drosophila) homolog 2 (SMAD 2); mothers against DPP homolog 2; Mad- | Pouponnot 1998 (ibid) |

-continued

| p300/cbp factor | Gene symbol | Other names | References |
|---|---|---|---|
| | | related protein 2; hMAD-2; JV18-1; hSMAD2 | |
| SRC-1 | SRC1 NCOA1 | steroid receptor coactivtor - 1 (SRC-1); F-SRC-1; nuclear receptor coactivator 1 (NCoA-1); SRC1 | Goodman 2000 (ibid), Hottoger 2000 (ibid) |
| SREBP1 | SREBF1 SREBP1 | sterol regulatory element binding protein-1 (SREBP-1); sterol regulatory element-binding transcription factor 1 | Goodman 2000 (ibid), Oliner 1996[54] |
| SREBP2 | SREBF2 SREBP2 | sterol regulatory element binding protein-2 (SREBP-2); sterol regulatory element-binding transcription factor 2 | Goodman 2000 (ibid), Oliner 1996 (ibid) |
| Stat-1 | STAT1 | signal transducer and activator or transcription - 1α/β; transcription factor ISGF-3 components p91/p84; signal transducer and activator of transcription 1, 91kD (STAT91) | Goodman 2000 (ibid), Paulson 1999[55], Hottiger 1998 (ibid), Gingras 1999 (ibid), Zhang 1996[56] |
| Stat-2 | STAT2 | signal transducer and activator or transcription - 2 (STAT2); ; signal transducer and activator of transcription 2, 113kD (STAT113); p113 | Goodman 2000 (ibid) Paulson 1999 (ibid), Hottiger 1998 (ibid) Gringras 1999 (ibid) Bhattacharya 1996[57], Hottiger 2000 (ibid) |
| Stat-3 | STAT3 APRF | signal transducer and activator or transcription - 3; acute-phase response factor | Paulson 1999 (ibid), Hottiger 1998 (ibid) |
| Stat-4 | STAT4 | signal transducer and activator or transcription - 4 | Paulson 1999 (ibid) |
| Stat-5 | STAT5 STAT5A STAT5B | signal transducer and activator or transcription - 5A (STAT5A); MGF; signal transducer and activator or transcription - 5B (STAT5B); STAT5 | Paulson 1999 (ibid) check, Gingras 1999 (ibid), Pfitzner 1998[58] |
| Stat-6 | STAT6 | signal transducer and activator or transcription - 6 (STAT6); IL-4 Stat; D12S1644 | Paulson 1999 (ibid) check, Gingras 1999[59] |
| TAL1 | TAL1 SCL TCL5 | T-cell acute lymphocytic leukemia-1 protein; TAL-1 protein; STEM cell protein; T-cell leukemia/lymphoma-5 protein | Goodman 2000 (ibid) |
| TBP | TBP TFIID TF2D | TATA box binding protein (TBP); transcription initiation factor TFIID; TATA-box factor; TATA sequence-binding protein; SCA17; GTF2D1; HGNC:15735; GTF2D | Goodman 2000 (ibid) |
| TFIIB | TFIIB TF2B GTF2B | transcription factor IIB (TFIIB, TF2B); transcription initiation factor IIB; general transcription factor IIB (GTFIIB, GTF2B) | Goodman 2000 (ibid), Hottiger 2000 (ibid) |
| THRA | THRA NR1A1 THRA1 ERBA1 | thyroid hormone receptor α (THRA); C-erbA-alpha; c-erbA-1; EAR-7; EAR7; AR7; avian erythroblastic leukemia viral (v-erb-a) oncogene homolog; ERBA; THRA1; THRA2; THRA3; EAR-7.1/EAR-7.2 | Hottiger 2000 (ibid) |
| THRB | THRB NR1A2 THR1 ERBA2 | thyroid hormone receptor β1 (THRB); thyroid hormone receptor, beta; avian erythroblastic leukemia viral (v-erb-a) oncogene homolog 2; THRB1; THRB2; ERBA2; NR1A2; thyroid hormone receptor β2 (THRB) | Hottiger 2000 (ibid) |
| Twist | TWIST | Twist related protein; H-twist; acrocephalosyndactyly 3 (Saethre-Chotzen syndrome); twist (Drosophila) homolog; acrocephalosyndactyly 3 (ACS3) | Goodman 2000 (ibid), Hamamori 1999[60] |
| YY1 | YY1 | Ying Yang 1 (YY1); transcriptional repressor protein YY1; delta transcription factor; NF-E1; UCRBP; CF1; Yin Yang 1; DELTA; YY1 transcription factor | Goodman 2000 (ibid) |

Viral

| | | | |
|---|---|---|---|
| E1A | | | Goodman 2000 (ibid), Hottiger 2000 (ibid) |
| EBNA2 | | EBV | Goodman 2000 (ibid) |
| Py LT | | polyomavirus large T antigen | Goodman 2000 (ibid) |

-continued

| p300/cbp factor | Gene symbol | Other names | References |
|---|---|---|---|
| SV40 LT | | simian virus 40 large T antigen, TAg | Goodman 2000 (ibid), Hottiger 2000 (ibid) |
| HPV E2 | | human papillomavirus E2 | Goodman 2000 (ibid) |
| HPV E6 | | human papillomavirus E6 | Goodman 2000 (ibid), Hottiger 2000 (ibid) |
| Tat | | HIV-1 | Goodman 2000 (ibid), Hottiger 2000 (ibid) |
| Tax | | Human T-cell leukemia virus type 1 | Goodman 2000 (ibid), Hottiger 2000 (ibid) |
| Bacterial | | | |
| JMY | | H pylori (cag) | Goodman 2000 (ibid) |

The two major lists are from reviews by Goodman 2000[61] and Hottiger 2000[62].

Mutations in some of these p300 factors are currently associated with chronic diseases. HNF4A with MODY, ESR1 with breast cancer and bronchial asthma, GR with cortisol resistance, etc. Consider the following definition.

(4) p300/cbp Regulated (Gene, Polypeptide)

Definition

Assume the gene G is transactivated, or suppressed by the transcription complex C. If C contains p300/cbp, the gene G, and the polypeptide encoded by G, are called "p300/cbp regulated."

Exemplary Assays

1. Co-transfect a cell with the gene promoter fused to a reporter gene, such as CAT or LUC, and a vector expressing p300/cbp. Assay reporter gene expression in the p300/cbp transfected cell and in control cells transfected with the fused gene promoter along with an "empty" plasmid. If reporter gene expression is higher or lower in the p300/cbp transfected cell, the gene is p300/cbp regulated.

2. Select a cell which expresses the gene of interest and transfect it with a vector expressing p300/cbp. Assay endogenous gene expression in the p300/cbp transfected cell and in control cells transfected with an "empty" plasmid. If gene expression is higher or lower in the p300/cbp transfected cell, the gene is p300/cbp regulated.

Note:

Preferably, verify that co-transfection did not induce a change in cellular microcompetition, a mutation in the gene promoter, or a change in methylation of gene promoter.

3. Transfect a cell with the gene promoter fused to a reporter gene, such as CAT or LUC. Contact the cell with an antibody against p300/cbp (or with a protein such as E1A). Assay gene expression in the antibody treated cell and in the untreated controls. If reporter gene expression is higher or lower in the antibody treated cell, the gene is p300/cbp regulated.

4. Select a cell which expresses a gene of interest. Contact the cell with an antibody against p300/cbp (or with a protein such as E1A). Assay gene expression in both the treated cell and in the untreated controls. If gene expression is higher or lower in the antibody treated cell, the gene is p300/cbp regulated.

5. Perform chromatin assembly of the gene promoter, for instance, with chromatin assembly extract from *Drosophila* embryos. Add a transcription factor during the chromatin assembly reactions. After the chromatin assembly reaction is complete add the p300/cbp proteins. Allow time for the interaction of the proteins with the chromatin template. Perform in vitro transcription reaction. Measure the concentration of the RNA products, by for instance, primer extension analysis. Compare to the RNA products before the addition of the p300/cbp proteins. If the addition of p300/cbp increased the concentration of the RNA products, the gene is p300/cbp regulated.

6. See more assays below.

Examples

Direct evidence shows transactivation of certain promoters by p300/cbp (Manning 2001[63], Kraus 1999[64], Kraus 1998[65]).

Indirect evidence is available in studies with p300/cbp factors. Consider, for example, the p300/cbp factor GABP. GABP binds promoters and enhancers of many cellular genes including $\beta_2$ leukocyte integrin (CD18) (Rosmarin 1998[66]), interleukin 16 (IL-16) (Bannert 1999[67]), interleukin 2 (IL-2) (Avots 1997[68]), interleukin 2 receptor β-chain (IL-2Rβ) (Lin 1993[69]), IL-2 receptor γ-chain (IL-2 γc) (Markiewicz 1996[70]), human secretory interleukin-1 receptor antagonist (secretory IL-1ra) (Smith 1998[71]), retinoblastoma (Rb) (Sowa 1997[72]), human thrombopoietin (TPO) (Kamura 1997[73]), aldose reductase (Wang 1993[74]), neutrophil elastase (NE) (Nuchprayoon 1999[75], Nuchprayoon 1997[76]), folate binding protein (FBP) (Sadasivan 1994[77]), cytochrome c oxidase subunit Vb (COXVb) (Basu 1993[78], Sucharov 1995[79]), cytochrome c oxidase subunit IV (Carter 1994[80], Carter 1992[81]), mitochondrial transcription factor A (mtTFA) (Virbasius 1994[82]), β subunit of the FoF1 ATP synthase (ATPsynβ) (Villena 1998[83]), prolactin (prl) (Ouyang 1996[84]) and the oxytocin receptor (OTR) (Hoare 1999[85]) among others. For some of these genes, for instance, CD18, COXVb, COXIV, GABP binds to the promoter while for others, for example IL-2 and ATPsynβ, GABP binds an enhancer. More examples see below.

Another p300/cbp factor is NF-Y (see above). Mantovani 1998[86], provides a list of genes which include a NF-Y binding site (Mantovani 1998, ibid, Table 1). For the listed genes, the table indicates whether the referenced studies report the presence of a proven binding site for a transcription factor close to the NF-Y binding site, whether cross-competition data with bona fide NF-Y binding sites are available, whether EMSA supershift experiments with anti NF-Y antibodies were performed, and whether the studies performed in vitro or in vivo transactivation studies with NF-Y. Some of the genes listed in the paper are MCH II, Ii, Mig, GP91 Phox, CD10, RAG-1, IL4, Thy-1, globin α, ζ, $γ^D$ $γ^P$, Coll α2 (I) α1 (I), osteopontin, BSP, apoA-I, aldolase B, TAT, γ-GT, SDH, fibronectin, arg lyase, factor VIII, factor X, MSP, ALDH, LPL, ExoKII, FAS, TSP-1, FGF-4, α1-chim, Tr Hydr, NaKATPsea-3, PDFGβ, FerH, MHC IA2 B8, Cw2Ld and B7, MDR1, CYP1A1, c-JUN, Grp78, Hsp70, ADH2, GPAT, FPP, HMG, HSS, SREBP2, GHR, CP2, β-actin, TK, TopoIIα, I, II, III, IV, cdc25, cdc2, cyclA, cyclB1, E2F1, PLK, RRR2, HisH2B, H is H3.

(5) p300/cbp Factor Kinase (p300/cbp Factor Phosphatase)

Definition

Assume F is a p300/cbp factor. If a molecule L stimulates phosphorylation or dephosphorylation of F, L is called "p300/cbp factor kinase" or "p300/cbp factor phosphatase", respectively.

Exemplary Assays

1. Contact a system (for instance, organism, cell, cell lysate, chemical mixture) with a test molecule L. Use assays described in the section entitled "Assaying protein phosphorylation," or similar assays, to uncover a change in phosphorylation of the p300/cbp factor of interest. An increase in phosphorylation indicates that L is a p300/cbp factor kinase, and a decrease indicates that L is a p300/cbp factor phosphatase.

Example

Ras, Raf, MEK1, MEK2, MEK4, ERK, JNK, three classes of ERK inactivators: type 1/2 serine/threonine phosphatases, such as PP2A, tyrosine-specific phosphatases (also called protein-tyrosine phosphatase, denoted PTP), such as PTP1B, and dual specificity phosphatases, such as MKP-1 which affect phosphorylation of a number of transcription factors, for instance, GABP, NF-κB. See also below.

(6) p300/cbp Agent

Definition

Assume the polynucleotide Pn binds the transcription complex C. Assume C contains p300/cbp. If a molecule L stimulates or suppresses binding of C to Pn, L is called "p300/cbp agent." Specifically, such an agent can stimulate or suppress binding of p300/cbp to a p300/cbp factor, binding of p300/cbp to DNA, or binding of a p300/cbp factor to DNA.

Exemplary Assays

1. Contact a system (for instance, whole organism, cell, cell lysate, chemical mixture) with a test molecule L. Use assays described in the section entitled "Assaying binding to DNA," or similar assays, to uncover a change in binding of the C to DNA. Specifically, assay for binding between p300/cbp and DNA, or p300/cbp and p300/cbp factor, or p300/cbp factor and DNA.

Examples

Examples of p300/cbp agents include sodium butyrate (SB), trichostatin A (TSA), trapoxin (for SB, TSA and trapoxin see in Espinos 1999[87]), phorbol ester (phorbol 12-myristate 13-acetate, PMA, TPA), thapsigargin (for PMA and thapsigargin see Shiraishi 2000[88], for PMA see Herrera 1998[89], Stadheim 1998[90]), retinoic acid (RA, vitamin A) (Yen 1999[91]), interferon-γ (IFNγ) (Liu 1994[92], Nishiya 1997[93]), heregulin (HRG, new differentiation factor, NDF, neuregulin, NRG) (Lessor 1998[94], Marte 1995[95], Sepp-Lorenzino 1996[96], Fiddes 1998[97]), zinc (Zn) (Park 1999[98], Kiss 1997[99]), copper (Cu) (Wu 1999[100], Samet 1998[101], both studies also show phosphorylation of ERK1/2 by Zn), estron, estradiol (Migliaccio 1996[102], Ruzycky 1996[103], Nuedling 1999[104]), interleukin 1β (IL-1β) (Laporte 1999[105], Larsen 1998[106]), interleukin 6 (IL-6) (Daeipoou 1993[107]), tumor necrosis factor α (TNFα) (Leonard 1999[108]), transforming growth factor β (TGFβ) (Hartsough 1995[109], Yonekura 1999[110], oxytocin (OT) (Strakova 1998[111], Copland 1999[112], Hoare 1999[113]). All studies show phosphorylation of ERK1/2 by these agents. See more agents below.

Other examples include agents which modify oxidative stress, such as, diethyl maleate (DEM), a glutathione (GSH)-depleting agent, and N-acetylcysteine (NAC), an antioxidant and a precursor of GSH synthesis. See more agents below.

(7) Foreign p300/cbp Polynucleotide

Definition

Assume Pn is a polynucleotide foreign to organism R. If Pn is a p300/cbp polynucleotide, Pn is called "p300/cbp polynucleotide foreign to R."

Exemplary Assays

Combine assays in the p300/cbp polynucleotide and foreign polynucleotide sections above.

Examples

See examples in "p300/cbp virus" below.

(8) p300/cbp Virus

Definition

Assume Pn is a p300/cbp polynucleotide. If Pn is a segment of the genome of a virus V, V is called a "p300/cbp virus."

Exemplary Assays

1. Verify that Pn is a p300/cbp polynucleotide (see assays above). Compare the sequence of Pn with the sequence of the published V genome. If the sequence is a segment of the V genome, Pn is a p300/cbp virus. If the V genome is not published, its sequence can be determined empirically.

2. Verify that Pn is a p300/cbp polynucleotide (see assays above) by hybridizing Pn to the V genome. If Pn hybridizes, Pn is a p300/cbp virus.

Examples

Direct evidence shows transactivation of certain viruses by p300/cbp. See, for instance, Subramanian 2002[114] on Epstein-Barr virus, Banas 2001, Deng 2000[115] on HIV-1[116], Cho 2001[117] on SV40 and polyomavirus, Wong 1994[118], on adenovirus type 5. See also Hottiger 2000[119], a review on viral replication and p300/cbp.

Indirect evidence is available in studies with p300/cbp factors. Consider, for instance, the p300/cbp factor GABP. Since GABP binds p300/cbp (see above), a complex on DNA which includes GABP, also includes p300/cbp. The DNA motif (A/C)GGA(A/T)(G/A), termed the N-box, is the core binding sequence for GABP. The N-box is the core binding sequence of many viral enhancers including the polyomavirus enhancer area 3 (PEA3) (Asano 1990[120]), adenovirus E1A enhancer (Higashino 1993[121]), Rous Sarcoma Virus (RSV) enhancer (Laimins 1984[122]), Herpes Simplex Virus 1 (HSV-1) (in the promoter of the immediate early gene ICP4) (LaMarco 1989[123], Douville 1995[124]), Cytomegalovirus (CMV) (IE-1 enhancer/promoter region) (Boshart 1985[125]), Moloney Murine Leukemia Virus (Mo-MuLV) enhancer (Gunther 1994[126]), Human Immunodeficiency Virus (HIV) (the two NF-κB binding motifs in the HIV LTR) (Flory 1996[127]), Epstein-Barr virus (EBV) (20 copies of the N-box in the +7421/+8042 or iP/enhancer) (Rawlins 1985[128]) and Human T-cell lymphotropic virus (HTLV) (8 N-boxes in the enhancer (Mauclere 1995 129) and one N-box in the LTR (Kornfeld 1987[130])). Moreover, some viral enhancers, for example SV40, lack a precise N-box, but still bind the GABP transcription factor (Bannert 1999[131]).

Ample evidence exists which supports the binding of GABP to the N-boxes in these viral enhancers. For instance, Flory, et al., 1996[132] show binding of GABP to the HIV LTR, Douville, et al., 1995[133] show binding of GABP to the promoter of ICP4 of HSV-1, Bruder, et al., 1991[134] and Bruder, et al., 1989[135] show binding of GABP to the adenovirus E1A enhancer element I, Ostapchuk, et al., 1986[136] show binding of GABP (called EF-1A in this paper) to the polyomavirus enhancer and Gunther, et al., 1994[137] show binding of GABP to Mo-MuLV.

Other studies demonstrate competition between these viral enhancers and enhancers of other viruses. Scholer and Gruss, 1984[138] show competition between the Moloney Sarcoma Virus (MSV) enhancer and SV40 enhancer and also competition between the RSV enhancer and the BK virus enhancer.

Another p300/cbp factor is NF-Y (see above). Mantovani 1998 (ibid), provides a list of viruses which include a NF-Y binding site (Table 1). The list includes HBV S, MSV LTR, RSV LTR, ad EIIL II, Ad MK, CMV gpUL4, HSV IE110k, VZV ORF62, MVM P4.

More Exemplary Assays for Identification of a Polynucleotide Pn as a p300/cbp Polynucleotide:

1. Take a cell of interest. Modify the copy number of Pn in the cell (by, for instance, transfection, infection, mutation, etc, see also above). Assay binding of all p300/cbp factors to Pn. If a p300/cbp factor binds Pn, Pn is a p300/cbp polynucleotide.

2. Assay binding of a p300/cbp factor to endogenous DNA or to exogenous DNA following introduction to the cell of interest. Modify the copy number of Pn in the cell. Assay binding of the p300/cbp factor again. If binding changed, Pn is a p300/cbp polynucleotide.

3. Identify a binding site on Pn for p300/cbp or a p300/cbp factor by computerized sequence analysis.

4. Take a cell of interest. Co-transfect a vector expressing Pn (or change the copy number of Pn in the cell through other means), and a promoter of a p300/cbp regulated gene fused to a reporter gene. Assay reporter gene expression and compare to cells co-transfected with an empty plasmid. If expression in the Pn transfected cell is different than controls, Pn is a p300/cbp polynucleotide.

5. Take a cell of interest which express a p300/cbp regulated gene. Modify the copy number of Pn in the cell (by, for instance, transfection, infection, mutation, etc, see also above). Assay expression of the p300/cbp regulated gene and compare to cells with an unmodified copy number of Pn (for instance in cells transfected with an empty plasmid). If expression in the Pn transfected cell is different than controls, Pn is a p300/cbp polynucleotide.

6. Take a cell of interest. Infect the cell with a p300/cbp virus. Modify the copy number of Pn in the cell (by, for instance, transfection, infection, mutation, etc, see also above). Assay viral replication and compare to cells with unmodified copy number of Pn (for instance, in cells infected with a non p300/cbp virus). If viral replication is different, Pn is a p300/cbp polynucleotide.

7. Compare the sequence of Pn to the genome of a p300/cbp virus using a sequence alignment algorithm such as BLAST. If a segment of the Pn sequence is identical (or homologous) to a segment in viral genome, Pn is a p300/cbp polynucleotide. A polynucleotide of at least 18 nucleotides should be sufficient to ensure specificity and validate alignment.

8. Try to hybridize Pn to the genome of a p300/cbp virus. If Pn hybridizes to the viral genome, Pn is a p300/cbp polynucleotide. Hybridization conditions should be sufficiently stringent to permit specific, but not promiscuous, hybridization. Such conditions are well known in the art.

c) Agents Related Elements (1) Modulator

Definition

Consider a polynucleotide Pn. An agent, or treatment (called agent for short), is called "modulator" if the agent modifies microcompetition with Pn, modifies at least one effect of microcompetition with Pn, or modifies at least one effect of another foreign polynucleotide-type disruption.

Notes:

1. A treatment, such as irradiation, can also be a modulator. In principle, according to the definition, any foreign polynucleotide-type disruption is a modulator.

Exemplary Assays

1. Assay the effect of an agent on Pn copy number.

Specifically, take a biological system (e.g. cell, whole organism, etc). Modify the copy number of Pn (by, for instance, transfection, infection, mutation, etc, see above). Call this cell the Pn cell. Assay the Pn copy number in the Pn cell (see above). Contact the biological system with an agent of interest. Assay again the Pn copy number. If the Pn copy number is higher or lower compared to the copy number in Pn cells not contacted with the agent, the agent is a modulator.

2. Assay the effect of an agent on binding of p300/cbp to Pn, directly or in a complex.

Specifically, take a biological system (e.g. cell, whole organism, etc). Modify the copy number of Pn (by, for instance, transfection, infection, mutation, etc, see above). Call this cell the Pn cell. Assay binding of p300/cbp to Pn (see above). Contact the biological system with an agent of interest. Assay again the binding of p300/cbp to Pn. If the binding is higher or lower compared to binding in Pn cells not contacted with the agent, the agent is a modulator.

3. Assay the effect of an agent on binding of a p300/cbp factor to Pn.

Specifically, take a biological system (e.g. cell, whole organism, etc). Modify the copy number of Pn (by, for instance, transfection, infection, mutation, etc, see above). Call this cell the Pn cell. Assay binding of a p300/cbp factor to Pn (see above). Contact the biological system with an agent of interest. Assay again the binding of the p300/cbp factor to Pn. If binding is higher or lower compared to binding in Pn cells not contacted with the agent, the agent is a modulator.

4. Assay the effect of an agent on binding of p300/cbp to a p300/cbp factor.

Specifically, take a biological system (e.g. cell, whole organism, etc). Modify the copy number of Pn (by, for instance, transfection, infection, mutation, etc, see above). Call this cell the Pn cell. Assay binding of p300/cbp to a p300/cbp factor (see above). Contact the biological system with an agent of interest. Assay again the binding of p300/cbp to a p300/cbp factor. If binding is higher or lower compared to binding in Pn cells not contacted with the agent, the agent is a modulator.

5. Assay the effect of an agent on expression of a disrupted gene and/or polypeptide.

Specifically, take a biological system (e.g. cell, whole organism, etc). Modify the copy number of Pn (by, for instance, transfection, infection, mutation, etc, see above). Call this cell the Pn cell. Identify a disrupted gene and/or polypeptide (see assays above). Contact the biological system with an agent of interest. Assay the bioactivity of the disrupted gene and/or polypeptide. If the bioactivity of the disrupted gene and/or polypeptide is higher or lower compared to the bioactivity in Pn cells not contacted with the agent, the agent is a modulator.

EXAMPLES

See below in constructive/disruptive.
(2) Constructive/Disruptive

Definition

A modulator, which attenuates or accentuates microcompetition with a foreign polynucleotide, attenuates or accentuates at least one effect of microcompetition with a foreign polynucleotide, or attenuates or accentuates at least one effect of another foreign polynucleotide-type disruption, is called "constructive" or "disruptive," respectively.

Notes:

1. A modulator can be both constructive and disruptive.

2. Consider a gene suppressed by microcompetition with a foreign polynucleotide. Consider such a gene in a cell without a foreign polynucleotide. Now consider a mutation which reduces the gene bioactivity. An agent which stimulates expression of such mutated gene will also be called constructive. If, on the other hand, the mutation stimulates the gene bioactivity, an agent which suppresses its bioactivity will also be called constructive.

3. A constructive agent can be an agonist, if it stimulates expression of a gene suppressed by microcompetition with a foreign polynucleotide, or if is stimulates bioactivity of a polypeptide encoded by such a gene. A constructive agent can also be an antagonist if it inhibits expression of a gene stimulated by microcompetition with a foreign polynucleotide, or inhibits the bioactivity of a polypeptide encoded by such a gene.

4. A foreign polynucleotide-type disruption can be constructive.

Exemplary Assays

1. See assays in Modulator section above. In these assay if either;

(a) Pn copy number in the Pn cell contacted with the agent is higher relative to Pn cells not contacted by the agent;

(b) binding of p300/cbp to Pn in the Pn cell contacted with the agent is higher compared to binding in Pn cells not contacted with the agent;

(c) binding of p300/cbp factor to Pn in the Pn cell contacted with the agent is higher compared to binding in Pn cells not contacted with the agent;

(d) binding of p300/cbp to a p300/cbp factor in the Pn cell contacted with the agent is higher or lower compared to binding in Pn cells not contacted with the agent;

(e) bioactivity of the disrupted gene and/or polypeptide in the Pn cell contacted with the agent is higher (for genes and/or polypeptides with suppressed bioactivity) compared to the bioactivity in Pn cells not contacted with the agent:

the agent is constructive.

If the effect is in the opposite direction, the agent is disruptive.

Examples

Antiviral drugs, sodium butyrate, garlic, etc. See more examples in Treatment section below.

2. Detailed Description of Standard Elements a) General Comments

The elements of the present invention may include, as their own elements, standard methods in molecular biology, microbiology, cell biology, transgenic biology, recombinant DNA, immunology, cell culture, pharmacology, and toxicology, well known in the art. The following sections provide details for some standard methods. Complete descriptions are available in the literature. For instance, see the "Current Protocols" series published by John Wiley & Sons. The following list provides a sample of books in the series: Current Protocols in Cell Biology, edited by: Juan S. Bonifacino, Mary Dasso, Jennifer Lippincott-Schwartz, Joe B Harford, and Kenneth M Yamada; Current Protocols in Human Genetics, edited by: Nicholas C Dracopoli, Jonathan L Haines, Bruce R Korf, Cynthia C Morton, Christine E Seidman, J G Seidman, Douglas R Smith; Current Protocols in Immunology, edited by: John E Coligan, Ada M Kruisbeek, David H Margulies, Ethan M Shevach, and Warren Strober; Current Protocols in Molecular Biology, edited by: Frederick M Ausubel, Roger Brent, Robert E Kingston, David D Moore, J G Seidman, John A Smith, and Kevin Struhl; Current Protocols in Nucleic Acid Chemistry, edited by: Serge L Beaucage, Donald E Bergstrom, Gary D Glick, Roger A Jones; Current Protocols in Pharmacology, edited by: S J Enna, Michael Williams, John W Ferkany, Terry Kenakin, Roger D Porsolt, James P Sullivan; Current Protocols in Protein Science, edited by: John E Coligan, Ben M Dunn, Hidde L Ploegh, David W Speicher, Paul T Wingfield: Current Protocols in Toxicology edited by: Mahin Maines (Editor-in-Chief), Lucio G Costa, Donald J Reed, Shigeru Sassa, I Glenn Sipes. The following lists includes more books with standard methods. Basic DNA and RNA Protocols (Methods in Molecular Biology, Vol 58), edited by Adrian J Harwood, Humana Press, 1994; DNA-Protein Interactions: Principles and Protocols (Methods in Molecular Biology, Volume 148), edited by Tom Moss, Humana Press, 2001; Transcription Factor Protocols (Methods in Molecular Biology), edited by Martin J Tymms, Humana Press, 2000; Gene Transcription: A Practical Approach, edited by B D Hames, and S J Higgins, IRL Press at Oxford University Press, 1993; Gene Transcription, DNA Binding Proteins: Essential Techniques, edited by Kevin Docherty, Jossey Bass, 1997; Gene Probes Principles and Protocols (Methods in Molecular Biology, 179), edited by Marilena Aquino de Muro and Ralph Rapley, Humana Press, 2001; Gene Isolation and Mapping Protocols (Methods in Molecular Biology Vol 68), edited by Jackie Boultwood and Jacqueline Boultwood, Humana Press, 1997; Gene Targeting Protocols (Methods in Molecular Biology, Vol 133), edited by Eric B Kmiec and Dieter C Gruenert, Humana Press 2000; Epitope Mapping Protocols (Methods in Molecular Biology, Vol 66), edited by Glenn E Morris, Humana Press, 1996; Protein Targeting Protocols (Methods in Molecular Biology, Vol 88), edited by Roger A Clegg, Humana Press, 1998; Monoclonal Antibody Protocols (Methods in Molecular Biology, 45), edited by William C Davis, Humana Press, 1995; Immunochemical Protocols (Methods in Molecular Biology Vol 80), edited by John D Pound, Humana Press, 1998; Immunoassay Methods and Protocols (Methods in Molecular Biology), edited by Andrey L Ghindilis, Andrey R Pavlov and Plamen B Atanassov, Humana Press, 2002; In situ Hybridization Protocols (Methods in Molecular Biology, 123), edited by Ian A Darby, Humana Presse, 2000; Bioluminescence Methods & Protocols, edited by Robert A Larossa, Humana Press, 1998; Affinity Chromatography: Methods and Protocols (Methods in Molecular Biology), etided by Pascal Bailon, George K Ehrlich, Wen-Jian Fung, wo Berthold and Wolfgang Berthold, Humana Press, 2000; Protocols for Oligonucleotide Conjugates: Synthesis and Analytical Techniques (Methods in Molecular Biology, Vol 26), edited by Sudhir Agrawal, Humana Press, 1993; RNA Isolation and Characterization Protocols (Methods in Molecular Biology, No 86). edited by Ralph Rapley and David L Manning, Humana Press, 1998; Protocols for Oligonucleotides and Analogs: Synthesis and Properties (Methods in Molecular Biology, 20), edited by Sudhir Agrawal, Humana Press, 1993; Basic Cell Culture Protocols (Methods in Molecular Biology, 75), edited by Jeffrey W Pollard and John M Walker, Humana Press, 1997; Quantitative PCR Protocols (Methods in Molecular Medicine, 26), edited by Bernd Kochanowski and Udo Reischl, Humana Press, 1999; In situ PCR Techniques, edited by Omar Bagasra and John Hansen, John Wiley & Sons, 1997; PCR Cloning Protocols: From Molecular Cloning to Genetic Engineering (Methods in Molecular Biology, No 67), edited by Bruce A White, Humana Press, 1996; PRINS and In situ PCR Protocols (Methods in Molecular Biology, 71), edited by John R Gosden, Humana Press, 1996; PCR Protocols: Current Methods and Applications (Methods in Molecular Biology, 15), edited by Bruce A White, Humana Press 1993; Transmembrane Signaling Protocols (Methods in Molecular Biology, Vol 84), edited by Dafna Bar-Sagi, Humana Press, 1998; Chemokine Protocols (Methods in Molecular Biology, 138), edited by Amanda E I Proudfoot, Timothy N C Wells and Chris Power, Humana Press, 2000; Baculovirus Expression Protocols (Methods in Molecular Biology, Vol 39), edited by Christopher D Richardson, Humana Press, 1998; Recombinant Gene Expression Protocols (Methods in Molecular Biology, 62), edited by Rocky S Tuan, Humana Press, 1997; Recombinant Protein Protocols: Detection and Isolation (Methods in Molecular Biology, Vol 63), edited by Rocky S Tuan, Humana Press, 1997; DNA Repair Protocols: Eukaryotic Systems (Methods in Molecular Biology, Vol 113), edited by Daryl S Henderson, Humana Press, 1999; DNA Sequencing Protocols, editors Hugh G Griffin and Annette M Griffin, Humana Press, 1993; Protein Sequencing Protocols (Methods in Molecular Biology, No 64), edited by Bryan John Smith, Humana Press, 2001; Gene Transfer and Expression Protocols (Methods in Molecular Biology, Vol 7), edited by E J Murray, Humana Press, 1991; Transgenesis Techniques, Principles and Protocols (Methods in Molecular Biology, 180), edited by Alan R Clarke, Humana Press, 2002; Regulatory Protein Modification Techniques and Protocols (Neuromethods, 30), edited by Hugh C Hemmings, Humana Press, 1996; Downstream Processing of Proteins Methods and Protocols (Methods in Biotechnology, 9), edited by Mohamed A Desai, Humana Press. 2000: DNA Vaccines Methods and Protocols (Methods in Molecular Medicine, 29), edited by Douglas B Lowrie and Robert Whalen, Humana Press, 1999; DNA Arrays Methods and Protocols (Methods in Molecular Biology, 170), edited by Jang B Rampal, Humana Press, 2001; Drug-DNA Interaction Protocols, editor Keith Fox, Humana Press, 1997; In vitro Mutagenesis Protocols, edited Michael K. Trower, Humana Press, 1996; In vitro Toxicity Testing Protocols (Methods in Molecular Medicine, 43), edited by Sheila O'Hare and C K Atterwill, Humana Press, 1995; Mutation Detection: A Practical Approach (Practical Approach Series (Paper), No 188), edited by Richard G H Cotton, E Edkins and S Forrect, Irl Press, 1998; Herpes Simplex Virus Protocols (Methods in Molecular Medicine, 10), edited by S Moira Brown and Alasdair R MacLean, Humana Press, 1997; HIV Protocols (Methods in Molecular Medicine, 17), edited by Nelson Michael and Jerome H Kim, Humana Press, 1999; Cytomegalovirus Protocols (Methods in Molecular Medicine, 33), edited by John Sinclair, Humana Press, 1999; Antiviral Methods and Protocols (Methods in Molecular Medicine, 24), edited by Derek Kinchington and Raymond F Schinazi, Humana Press, 1999; Epstein-Barr Virus Protocols (Methods in Molecular Biology Vol 174), edited by Joanna B Wilson and Gerhard H W May, Humana Press, 2001; Adenovirus Methods and Protocols (Methods in Molecular Medicine, Vol 21), edited by William S M Wold, Humana Press, 1999; Molecular Methods for Virus Detection, edited by Danny L Wiedbrauk and Daniel H Farkas, Academic Press, 1995; Diagnostic Virology Protocols (Methods in Molecular Medicine, No 12), edited by John R Stephenson and Alan Warnes, Humana Press, 1998. A more extensive list of books with detailed description of standard methods is available at the Promega web site: http://www.promega.com/catalog/
   category.asp?catalog%5Fname=Promega%5FProducts
   &category%5Fname=Books&description%5Ftext=
   Books&Page=1. The Promega list includes 260 books.

For each element, one or more exemplary protocols are presented. All examples included in the application should be considered as illustrations, and, therefore, should not be construed as limiting the invention in any way.

More details regarding the presented exemplary protocols, and details of other protocols that can be used instead of the presented protocols, are available in the cited references, and in the books listed above. The contents of all references cited in the application, including, but not limited to, abstracts, papers, books, published patent applications, issued patents, available in paper format or electronically, are hereby expressly and entirely incorporated by reference.

The following sections first present protocols for formulation of a drug candidate, then protocols, that as elements of above assays, can be used to test a drug candidate for a desired biological activity during drug discovery, development and clinical trials. The assays can also be used for diagnostic purposes. Finally, the following sections also present protocols for effective use of a drug as treatment.

b) Formulation Protocols

One aspect of the invention pertains to administration of a molecule of interest, equivalent molecules, or homologous molecules, isolated from, or substantially free of contaminating molecules, as treatment of a chronic disease.

(1) Definitions (a) Molecule of Interest

The terms "molecule of interest" or "agent," is understood to include small molecules, polypeptides, polynucleotides and antibodies, in a form of a pharmaceutical or nutraceutical.

(b) Equivalent Molecules

The term "equivalent molecules" is understood to include molecules having the same or similar activity as the molecule of interest, including, but not limited to, biological activity, chemical activity, pharmacological activity, and therapeutic activity, in vitro or in vivo.

(c) Homologous Molecules

The term "homologous molecules" is understood to include molecules with the same or similar chemical structure as the molecule of interest.

In one exemplary embodiment, homologous molecules may be synthesized by chemical modification of a molecule of interest, for instance, by adding any of a number of chemical groups, including but not limited to, sugars (i.e. glycosylation), phosphates, acetyls, methyls, and lipids. Such derivatives may be derived by the covalent linkage of these or other groups to sites within a molecule of interest, or in the case of polypeptides, to the N-, or C-termini, or polynucleotides, to the 5' or 3' ends.

In one exemplary embodiment, homologous polypeptides or homologous polynucleotides include polypeptides or polynucleotides that differ by one or more amino acid, or nucleotides, respectively, from the polypeptide or polynucleotide of interest. The differences may arise from substitutions, deletions or insertions into the initial sequence, naturally occurring or artificially formulated, in vivo or in vitro. Techniques well known in the art may be applied to introduce mutations, such as point mutations, insertions or deletion, or introduction of premature translational stops, leading to the synthesis of truncated polypeptides. In every case, homologs may show attenuated activities compared to the original molecules, exaggerated activities, or may express a subset or superset of the total activities elicited by the original molecule. In these ways, homologs of constructive or disruptive polypeptides or polynucleotides have biological activities either diminished or expanded compared to the original molecule. In every case, a homolog may, or may not prove more effective in achieving a desired therapeutic effect. Methods for identifying homologous polypeptides or polynucleotides are well known in the art, for instance, molecular hybridization techniques, including, but not limited to, Northern and Southern blot analysis, performed under variable conditions of temperature and salt, can formulate nucleic acid sequences with different levels of stringency. Suitable protocols for identifying homologous polypeptides or polynucleotides are well known in the art (see for instance. Sambrook 2001[139] and above listed books of standard protocols). Homologous polypeptides or polynucleotides can also be generated, for instance by a suitable combinatorial approach.

It is well known in the art that the ribonucleotide triplets, termed codons, encoding each amino acid, comprise a set of similar sequences typically differing in their third position. Variations, known as degeneracy, occur naturally, and in practice mean that any given amino acid may be encoded by more than one codon. For instance, the amino acids arginine, serine and leucine can be encoded by 6 codons. As a result, in one exemplary embodiment, homologous DNA and RNA polynucleotides can be produced which encode the same polypeptide of interest.

In another exemplary embodiment, a set of homologous polypeptides may be generated by incorporating a population of synthetic oligodeoxyribonucleotides into expression vectors already carrying additional portions of the polypeptide of interest. The site into which the oligonucleotide-gene fusion is incorporated must include appropriate transcriptional and translational regulatory sequences flanking the inserted oligonucleotides to permit expression in host cells. Once introduced into an appropriate host cell, the resulting collection of gene-oligonucleotide recombinant vectors expresses polypeptide variants of the polypeptide of interest. The expressed polypeptide may be separately purified by cloning the vector bearing host cells, or by employing appropriate bacteriophage vectors, such as gt-11 or its derivatives, and screening plaques with antibodies against the polypeptide of interest, or against an immunological tag included in the recombinants.

(d) Isolated

The terms "isolated from, or substantially free of contaminating molecules" is understood to include a molecule containing less than about 20% contaminating molecules, based on dry weight calculations, preferably, less than about 5% contaminating molecules.

The terms "isolated" or "purified" do not refer to materials in a natural state, or materials separated into elements without further purification. For example, separating a preparation of nucleic acids by gel electrophoresis, by itself, does not constitute purification unless the individual molecular species are subsequently isolated from the gel matrix.

In one exemplary embodiment, a polynucleotide encoding a polypeptide of interest is ligated into a fusion polynucleotide encoding another polypeptide which facilitates purification, for instance, a polypeptide with readily available antibodies, such as VP6 rotavirus capsid protein, a vaccinia virus capsid protein, or the bacterial GST protein. When expressed, the facilitator polypeptide enables purification of the polypeptide of interest and immunological identification of host cells which express it. In the case of GST-fusion proteins, purification may be achieved by use of glutathione-conjugated sepharose beads in affinity chromatographic techniques well known in the art (see, for instance, Ausubel 1998[140]).

In a related exemplary embodiment, the fusion polypeptide includes a polyamino acid tract, such as the polyhistidine/enterokinase cleavage site, which confers physical properties that inherently enable purification. In this example, purification may be achieved through nickel metal affinity chromatography. Once purified, the polyhistidine tract included to enable purification can be removed by treatment with enterokinase in vitro to release the polypeptide fragment of interest.

For molecules synthesized by an organism, for instance, polypeptides or polynucleotides synthesized by human subjects, in a preferred exemplary embodiment, a purified polynucleotide or polypeptide is free of other molecules synthesized by same organism, accomplished, for example, by expression of a human gene in a non-human host cell.

The following sections present standard protocols for the formulation of certain types of agents.

(2) Small Molecules

One aspect of the invention pertains to administration of a small molecule of interest, equivalent small molecules, or homologous small molecules, isolated from, or substantially free of contaminating molecules, as treatment of a chronic disease.

The following sections present standard protocols for formulation of small molecules.

(a) Production

Small molecules, organic or inorganic, may be synthesized in vitro by any of a number of methods well known in the art. Those small molecules, and others synthesized in vivo, may by purified by, for instance, liquid or thin layer chromatography, high performance liquid chromatography (HPLC), electrophoresis, or some other suitable technique.

(3) Polypeptides

Another aspect of the invention pertains to administration of a polypeptide of interest, equivalent polypeptides, or homologous polypeptides, isolated from, or substantially free of contaminating molecules, as treatment of a chronic disease.

The following sections present standard protocols for the formulation of polypeptides.

(a) Production (i) In vitro

In one exemplary embodiment, a polypeptide of interest is produced in vitro by introducing into a host cell by any of a number of means well known in the art (see protocols below) a recombinant expression vector carrying a polynucleotide, preferably obtained from vertebrates, especially mammals, encoding a polypeptide of interest, equivalents of such polypeptide, or homologous polypeptides. The recombinant polypeptide is engineered to include a tag to facilitate purification. Such tags include fragments of the GST protein, or polyamino acid tracts either recognized by specific antibodies, or which convey physical properties facilitating purification (see also below). Following culture under suitable conditions, the cells are lysed and the expressed polypeptide purified. Typical culture conditions include appropriate host cells, growth medium, antibiotics, nutrients, and other metabolic byproducts. The expressed polypeptide may be isolated from either a host cell lysate, culture medium, or both depending on the expressed polypeptide. Purification may involve any of many techniques well known in the art, including but not limited to, gel filtration, affinity chromatography, gel electrophoresis, ion-exchange chromatography, and others.

Polynucleotides, both mRNA and DNA, can be extracted from prokaryotic or eukaryotic cells, or whole animals, at any developmental stage, for instance, adults, juveniles, or embryos. Polynucleotides may be isolated, or cloned from a gehomic library, cDNA library, or freshly isolated nucleic acids, using protocols well known in the art. For instance, total RNA is isolated from cells, and mRNA converted to cDNA using oligo dT primers and viral reverse transcriptase. Alternatively, a polynucleotide of interest may be amplified using PCR. In any case, the initial nucleic acid preparation may include either RNA or DNA and the protocols chosen accordingly. The resulting DNA is inserted into an appropriate vector, for instance, bacterial plasmid, recombinant virus, cosmid, or bacteriophage, using procedures well known in the art.

Nucleotide sequences are considered functionally linked if one sequence regulates expression of the other. To facilitate expression of a polypeptide of interest, the cloning vector should include suitable transcriptional regulatory sequences well known in the art, for instance, promoter, enhancer, polyadenylation site, etc., functionally linked to the polynucleotide expressing the polypeptide of interest. In one exemplary embodiment, an expression vector is constructed to carry a polynucleotide, a naturally occurring sequence, a gene, a fusion of two or more genes, or some other synthetic variant, under control of a regulatory sequence, such that when introduced into a cell expresses a polypeptide of interest.

Both viral and nonviral gene transfer methods may be used to introduce desirable polynucleotides into cells. Viral methods exploit natural mechanisms for viral attachment and entry into target cells. Nonviral methods take advantage of normal mammalian transmembrane transport mechanisms, for example, endocytosis. Exemplary protocols employ packaging of deliverable polynucleotides in liposomes, encasement in synthetic viral envelopes or poly-lysine, and precipitation with calcium phosphate (see also below).

The variety of suitable expression vectors is vast and growing. For example, mammalian expression vectors typically include prokaryotic elements which facilitate propagation in the laboratory, eukaryotic elements which promote and regulate expression in mammalian cells, and genes encoding selectable markers. The list of appropriate vectors includes, but is not limited to, pcDNA/neo, pcDNA/amp, pRSVneo, pZIPneo, and a host of others. Many viral derivatives are also available, for instance, pHEBo, derived from the Epstein-Barr virus, BPV-a derived from the bovine papillomavirus, and the pLRCX system (BD Biosciences Clonetech, Inc.). The use of mammalian expression vectors is well known in the art (see, for example, Sambrook 2001, ibid, chapters 15 and 16). Similarly, many vectors are available for expression of recombinant polypeptides in yeast, including, but not limited to, YEP24, YEP5, YEP51, pYES2. The use of expression vectors in yeast is well known in the art.

In addition to mammalian and yeast expression systems, a system of vectors is available which permits expression in insect cells. The system, derived from baculoviruses, includes pAcUW-1 based vectors (for instance, pAcUW1), pVL-based vectors (for instance, pVL1292 and pVL1393), and pBlueBac-based vectors which carry the gene encoding β-galactosidase to facilitate selection of host cells harboring recombinant vectors.

(ii) In Situ

In another exemplary embodiment, a polypeptide of interest is expressed in situ by administering to an animal or human subject by any of a number of means well known in the art (see protocols below) a recombinant expression vector carrying a polynucleotide encoding the polypeptide of interest, equivalent polypeptides, or homologous polypeptides.

In the present invention, such vectors may be used as therapeutic agents to introduce polynucleotides into cells that express constructive or disruptive polypeptides (for exemplary applications see, for instance, Friedmann 1999[141]).

It is critical that the potential effects of microcompetition between the enhancer, or other polynucleotide sequences carried in the delivery vector, and cellular genes be considered and manipulated where needed. As an example consider a case where the polypeptide of interest binds an enhancer carried by the vector, for instance, a delivery vector that expresses GABP under control of a promoter that includes an N-box. In one exemplary embodiment, the vector expresses, in situ, a high enough concentration of the polypeptide of interest such that any binding of the polypeptide to the enhancer sequences within the vector itself is negligible. In other words, the vector expresses enough free polypeptides to produce the desired biological activity in treated cells. In another example, the polypeptide is not a transcription factor, but the delivery vector carries a polynucleotide that microcompetes with cellular genes for a cellular transcription factor, for instance, a vector that expresses Rb and microcompetes with cellular genes for GABP. In an exemplary embodiment, the delivery vector also includes a polynucleotide sequence that expresses the microcompeted transcription factor, or is delivered in conjunction with another vector that expresses the microcompeted transcription factor. In the example, the Rb vector includes a sequence that expresses GABP, or is delivered in conjunction with a vector that expresses GABP.

(4) Polynucleotides

Another aspect of the invention pertains to administration of a polynucleotide as antisense/antigene, ribozyme, triple helix, homologous nucleic acids, peptide nucleic acids, or microcompetitiors, equivalent polynucleotides, or homologous polynucleotides, isolated from or substantially free of contaminating molecules as treatment for a chronic disease.

The following sections present standard protocols for the formulation of such polynucleotides. Since antisense/antigene, ribozyme, triple helix, homologous nucleic acids, peptide nucleic acids, and microcompetition agents are nucleic acid based, they share protocols for their synthesis, mechanisms of delivery and potential pitfalls in their use including, but not limited to, susceptibility to extracellular and intracellular nucleases, instability and the potential for nonspecific interactions. In consideration of these common issues, the general methods for the formulation and delivery, as well as caveats regarding the use of nucleic agents, described first, apply similarly to each subsequent agent.

(a) Antisense/antigene

In the present invention, the terms "antisense" and "antigene" polynucleotides is understood to include naturally or artificially generated polynucleotides capable of in situ binding to RNA or DNA, respectively. Antisense binding to mRNA may modify translation of bound mRNA, while antigene binding to DNA may modify transcription of bound DNA. Antisense/antigene binding may modify binding of a polypeptide of interest to RNA or DNA, for instance binding of an antigene to a foreign N-box may reduce binding of cellular GABP to the foreign N-box resulting in attenuated microcompetition between the foreign polynucleotide and a cellular gene for GABP. Antisense/antigene binding may also modify, i.e., decrease or increase, expression of a polypeptide of interest.

Binding, or hybridization of the antisense/antigene agent, may be achieved by base complementarity, or by interaction with the major groove of the cellular DNA duplex. The techniques and conditions for achieving such interactions are well known in the art.

The target of antisense/antigene agents has been thoroughly studied and is well known in the art. For instance, the antisense preferred target is the translational initiation site of a gene of interest, from approximately 10 nucleotides upstream to approximately 10 nucleotides downstream of the translational initiation site. Oligonucleotides targeting the 3' untranslated mRNA regions are also effective inhibitors of translation. Therefore, oligonucleotides targeting the 5' or 3' UTRs of a polynucleotide of interest may be used as antisense agents to inhibit translation. Antisense agents targeting the coding region are less effective inhibitors of translation but may be used when appropriate.

Effective synthetic agents are typically between 20 and 30 nucleotides in length. However, to be effective, a complementary sequence must be sufficiently complementary to bind tightly and uniquely to the polynucleotide of interest. The degree of complementarity is generally understood by those skilled in the art to be measured relative to the length of the antisense/antigene agent. In other words, three bases of mismatch in a 20 base oligonucleotide has a more profoundly detrimental effect than three bases of mismatch in a 100 base oligonucleotide. Inadequate complementarity results in ineffective inhibition, or unwanted binding to sequences other than the polynucleotide of interest. In the latter case, inadvertent effects may include unwanted inhibition of genes other than a gene of interest. Specificity and binding avidity are easily determined empirically by methods known in the art.

Several methods are suitable for the delivery of antisense/antigene agents. In one exemplary embodiment, a recombinant expression plasmid is engineered to express antisense RNA following introduction into host cells. The RNA is complementary to a unique portion of DNA or mRNA sequence of interest. In an alternative embodiment, chemically derivatized synthetic oligonucleotides are used as antisense/antigene agents.

Such oligonucleotides may contain modified nucleotides to attain increased stability once exposed to cellular nucleases. Examples of modified nucleotides include, but are not limited to, nucleotides carrying phosphoramidate, phosphorothioate and methylphosphonate groups.

Whichever sequence of the polynucleotide of interest is targeted by antisense/antigene agents, in vitro studies should be undertaken first to determine the effectiveness and specificity of the agent. Control treatments should be included to differentiate between effects specifically elicited by the agent and non-specific biological effects of the treatment. Control polynucleotides should have same length and nucleotide composition as the agent with the base sequence randomized.

Antisense/antigene agents can be oligonucleotides of RNA, DNA, mixtures of both, chemical derivatives of either, and single or double stranded. Nucleotides within the oligonucleotide may carry modifications on the nucleotide base, the sugar or the phosphate backbone. For example, modifications to the nucleotide base involves a number of compounds including, but not limited to, hypoxanthine, xanthine, 2-methyladenine, 2-methylguanine, 7-methylguanine, 5-fluorouracil, 3-methylcytosine, 2-thiocytosine, 2-thiouracil, 5-methylcytosine, 5-methylaminomethyluracil, and a host of others well known in the art. Modifications are generally incorporated to increase stability, e.g. infer resistance to cellular nucleases, stabilize hybridization, or increase solubility of the agent, increased cellular uptake, or some other appropriate action.

In a related exemplary embodiment, adducts of polypeptides, to target the agent to cellular receptors in vivo, or other compounds which facilitate transport into the target cell are included. Additional compounds may be adducted to the antisense/antigene agent to enable crossing of the blood-brain barrier, cleavage of the target sequence upon binding, or to intercalate in the duplex which results from hybridization to stabilize that complex. Any such modification, intended to increase effectiveness of the antisense/antigene agent, is included in the present invention.

Similarly, the antisense/antigene agent may include modifications to the phosphate backbone including, but not limited to, phosphorothioates, phosphordamidate, methylphosphonate, and others. The agent may also contain modified sugars including, but not limited variants of arabinose, xylulose and hexose.

In another exemplary embodiment, the antisense/antigene agent is an alpha anomeric oligonucleotide capable of forming parallel, rather than antiparallel, hybrids with a cellular mRNA of interest.

It is common for antisense agents to be targeted against the coding regions of an RNA of interest to effect translational inhibition. In a preferred embodiment, antisense agents are targeted instead against the transcribed but untranslated region of an RNA transcript. In this case, rather than achieving translational inhibition, it is likely that oligonucleotides hybridized to the target transcript will lead to mRNA degradation through a pathway mediated by RNaseH or similar cellular enzymes.

For optimal efficacy, the antisense/antigene agents must be delivered to cells carrying the polynucleotide of interest in vivo. Several delivery methods are known in the art, including but not limited to, targeting techniques employing polypeptides linked to the antisense/antigene agent which bind to specific cellular receptors. In this instance the agents may be provided systemically. Alternatively the agents may be injected directly into the tissue of interest, or packaged in a virus, including retroviruses, chosen because its host range includes the target cell. In every case, the agent must enter the target cell to be effective.

Antisense/antigene methodologies often face the problem of achieving sufficient intracellular concentration of the agent to effectively compete with cellular transcription and/ or translation factors. To overcome this challenge, those skilled in the art introduce recombinant expression vectors carrying the antisense/antigene agent. Once introduced into the target cell, expression of the antisense/antigene agent from the incorporated RNA polymerase II or III promoter results in sufficient intracellular concentrations. Vectors can be chosen to integrate into the host cell chromosomes, thereby becoming stable through multiple rounds of cell division, or vectors may be used which remain un integrated and therefore are lost when the target cell divides. In either case, the primary goal is attaining levels of transcription that produce sufficient antisense/antigene agents to be effective. The choice of a suitable vector and the development of an effective antisense construct involves techniques standard in the art.

Antisense/antigene expression man be regulated by any promoter known to be active in mammalian, especially human, cells and may be either constitutively active or inducible. Regardless of the promoter chosen, it is important to test for the effect of any enhancer regions intrinsic to those promoters as they may participate in microcompetition with cellular genes. In the case of inducible promoters, the biological effects of the expressed antisense can be discerned from any effect the promoter has on microcompetition by assaying any bioactivity with and without induced gene expression. Suitable promoters, inducible or not, are well known in the art (see, for example, Jones 1998[142]).

Antisense agents may be prepared using any of a number of methods commonly known to those skilled in the art. In on exemplary embodiment, oligonucleotides, up to approximately 50 nucleotides in length, may be synthesized using automated processes employing solid phase, e.g. controlled pore glass (CPG) technology, such as that used on the Applied Biosystems model 394 medium throughput synthesizer, or 5'-phosphate ON (cyanoethyl phosphoramidite) chemistry developed by Clonotech Laboratories, Inc. In each of these procedures, oligonucleotides are synthesized from a single nucleotide using a series of deprotection and ligation steps. The underlying chemistry of the reactions is standard practice and the availability and accessibility of automated synthesizers bring these synthetic technologies within the grasp of anyone skilled in the art.

Despite the ease of synthesis, the selection of effective antisense agents involves the identification of a suitable target for the agent. This process is simplified somewhat by the many software programs available, such as, for example, Premier Primer 5, available from Premier Biosoft International or Primer 3, available online at http://www-genome.wi.mit.edu/cgi-bin/primer/primer3.cgi. Alternatively, antisense agents may be designed manually by a scientist skilled in the art. Relevant aspects of the design process which need attention include selection of the target region to which the antisense agent will bind. Ideally it will be the gene promoter, if the target is DNA, or the translation initiation site if the target is an mRNA. Attention also needs to be paid to the length of the agent, typically at least 20 nucleotides are needed for specificity. Shorter oligonucleotides carry the risk of non-specific binding and therefore may lead to undesired side effects. Also, the agents must be composed of a sequence that will not promote hybridization between the oligonucleotides in the agent during application. Taken together, these considerations are well known and are addressed by standard procedures well known in the art.

Longer antisense agents may be produced within the target cell from recombinant expression vectors. In one exemplary embodiment, the desired antisense-encoding sequences can be incorporated into an appropriate expression vector selected because it contains the regulatory sequences necessary to ensure expression in the target cell type. Selection of the sequence composition of the antisense agent must take into account the same considerations used to design shorter oligonucleotides as described in the previous paragraph including, but not limited to, binding specificity for the target sequence and minimizing interactions between the expressed agents. Techniques for the design and construction of appropriate recombinant expression vectors are well known to those skilled in the art.

Control agents, whether synthetic oligonucleotides or longer antisense agents expressed in vivo by expression vectors, are employed to validate the efficacy and specificity of the therapeutic agents. Each control agent should have the same nucleotide composition and length as the therapeutic agent but the sequence should be random. Employment of this agent will permit the determination of whether any effects observed after treatment with the therapeutic agent are indeed specific. Specificity will reduce the potential for binding to targets other than those desired, thereby reducing associated unwanted side effects.

Purification of Oligonucleotides: The efficacy of synthetic oligonucleotide agents is impacted by their purity. Under typical conditions, approximately 75% of the synthesis products are full length while the remaining 25% of the oligonucleotides are shorter. This proportion of full length to shorter products varies with the length of the desired product. The synthesis of longer oligonucleotides is less efficient, and therefore the synthesis products contain a smaller proportion of full length products, than that of shorter ones. Unwanted, shorter synthesis products have reduced specificity compared to the full length products and are therefore undesirable in a therapeutic formulation due to their reduced specificity which in turn leads to an increased risk of side effects.

In one exemplary embodiment, full length oligonucleotides greater than 50 bp in length are purified by virtue of their size. Gel permeation chromatography is used to separate full length products from the shorter synthetic byproducts. In a complementary exemplary embodiment, full length synthetic oligonucleotides shorter than 50 bp may be purified by liquid chromatography using charged resins such as hydroxyapatite or nucleic acid specific resins such as RPC-5 (which is composed of trioctylmethylamine adsorbed onto hydrophobic plastic particles). This latter technique exploits both hydrophobic and ion exchange methods to achieve high reagent purity and is amenable to use in HPLC.

Regardless of the method of purification used, the desired oligonucleotides are concentrated by precipitation with ice cold ethanol followed by lyophilization and dissolution in an appropriate carrier for treatment. Carrier selection is another important component of agent formulation. It is essential that the carrier used is first tested for biological activity in the target cell type. This control measure, well known to those skilled in the art, will ensure that any effects observed upon administration of the nucleic acid agent are indeed due to the agent and not the carrier in which it is administered (on purification of oligonucleotides see, for instance, Deshmukh (1999[143]).

Delivery of Oligonucleotides: Methods for effective administration of antisense agents vary with the agent used. In one exemplary embodiment, synthetic oligenucleotides are delivered by simple diffusion into the target cells. Advantages of this delivery method include the ability to administer the agent systemically, for example by intravenous injection. This method, while effective carries several risks, not the least of which is the potential to introduce oligonucleotides into cells other than those of the desired target. Another disadvantage involves the risk of degradation by nucleases in blood and interstitial fluid. This second disadvantage may be partially avoided by modification of the synthetic oligonucleotide in such a way, for example by incorporated modified nucleotides such as those carrying phosphorothioate or methyl phosphonate moieties, which renders them relatively resistant to exonuclease degradation.

In a related embodiment those same agents may be delivered by way of liposome mediated transfection as described by Daftary and Taylor (2001[144]). This method enhances diffusion into the target cell by encasing the antisense agent in a lipophilic liposome. However, this method too has drawbacks. While cellular uptake is enhanced, the ratio of liposome components to DNA must be carefully controlled in order to maximize delivery efficiency. This technique is commonly employed and is well known to those skilled in the art.

In another exemplary embodiment, antisense expressing viral vectors may be used to confer target cell specificity. In some cases, viral delivery agents may be selected which include the target cell type in their respective host range. This delivery method minimizes unwanted side effects that otherwise may arise from delivery of the therapeutic agent to the incorrect cell type. However, this advantage may be negated if the multiplicity of infection is too high and non-specific infection is thereby promoted. This potential problem may be avoided by thoroughly testing any viral deliver agent, using techniques well known in the art, prior to its clinical administration.

(b) Ribozymes

While antisense agents act by either inhibiting transcription or translation of the target gene, or by inducing enzyme-mediated transcript degradation by RNase H or a similar enzyme, ribozymes offer an alternative approach. Ribozymes are RNA molecules which natively bind to and cleave target transcripts. Typical ribozymes bind to and cleave RNA at specific sites, however hammerhead ribozymes cleave target transcripts at sites directed by flanking nucleotide sequences which bind to the target site. The use of hammerhead ribozymes is preferred because the only sequence requirement for their activity is the UG dinucleotide arranged in the 5'-3' orientation. Hammerhead technologies are well known in the art (see, for example Doherty 2001[145], or Goodchild2000[146]). In a preferred embodiment, the sequence targeted by the ribozyme lies near the 5' end of the transcript. That will result cleavage of the transcript near the translation initiation site thereby blocking translation of a full-length protein.

Ribozymes identified in *Tetrahymena thermophila*, which employ an eight base pair active site which duplexes with the target RNA molecule, are included in this invention. This invention includes those ribozymes, described and characterized by Cech and coworkers (i.e. IVS or L-19IVS RNA), which target eight base-pair sequences in a gene of interest and any others which may be effective in inhibiting expression of a disrupted gene or a gene in a disrupting pathway. For the catalytic sequence of these agents see, for instance, U.S. Pat. No. 5,093,246, incorporated entirely herein by reference. Any ribozyme or hammerhead ribozyme molecules that targets RNA sequences expressed by a foreign polynucleotide, disrupted gene or gene in a disrupted pathway are included in this invention.

Ribozymes, being RNA molecules of specific sequence, may be synthesized with modified nucleotides which enable better targeting to the host cell of interest or which improve stability. As described above for conventional antisense agents, the preferred method of delivery involves introduction into the target cell, a recombinant expression vector encoding the ribosome. Inclusion of an appropriate transcriptional promoter will ensure sufficient expression to cleave and disrupt transcripts of foreign DNA or disrupted genes or genes in a disrupting pathway. The catalytic nature of ribozymes permits their effective use at concentrations below those needed for traditional antisense agents.

Identification of ribozyme cleavage sites within a transcript of interest is accomplished with any of a number of computer algorithms which scan linear oligonucleotide sequences for alignments with a query sequence. The identified sequence, commonly containing the trinucleotide sequences GUC, GUA or GUU, will serve as the nucleus of a longer sequence of approximately 20 nucleotides in length. That longer sequence will be examined, again with appropriate computer algorithms well known in the art, for their potential to form secondary structures which may interfere with the action of targeted ribozyme agents. Alternatively, empirical assays employing ribonucleases may be used to probe the accessibility of identified target sequences.

Ribozymes comprise a unique class of oligonucleotides which bind to specific ribonucleic acid targets and promote their hydrolysis. The design of ribozyme agents is well known to those skilled in the art. In order to prepare effective ribozyme agents, initially a suitable target sequence must be identified which confers specificity to the agent in order to minimize unwanted side effects and maximize efficacy. Once that target is identified the ribozyme agent is synthesized using standard oligonucleotide synthesis procedures such as those exemplified herein. Delivery to the target cell may be accomplished by direct transfection ex vivo or by liposome-mediated transfection.

Ensuring the purity and efficacy of ribozyme agents may be more important than for other nucleic acid agents because their intended effects, namely the hydrolysis of target sequences, are irreversible. In this light extensive preclinical testing is essential to minimize unwanted side effects. These risks are, however, outweighed by the potential effectiveness of ribozyme agents.

(c) Triple Helix

In a related embodiment, synthetic single-stranded deoxyribonucleotides can be chosen which form triple helices according to the Hoogsteen base pairing rules. The rules necessitate long stretches of either purines or pyrimidines on one strand of the DNA duplex. In either case, triplexes are formed, with pyrimidines pairing with purines within the target sequence and vice versa, which inhibit transcription of the target sequence. The effectiveness of a targeted triplex forming oligonucleotide may be enhanced by including a "switchback" motif composed of alternating 5'-3' and 3'-5' regions of purines and pyrimidines. This "switchback" reduces the length of the required purine or pyrimidine tract in the target because the oligonucleotide can form duplexes alternatively with each strand of the target sequence.

Triple helix forming agents are oligonucleotides which have been designed to interact with cellular nucleic acids and form triple helices. The resulting structure may be targeted by intracellular degradation pathways or may provide a steric block to nucleic acid replication, transcription or translation depending on the target.

Triplex agent formulation begins with selection of an appropriate target sequence within the cells to be treated. That target may be within the cellular DNA or RNA or within that of an exogenous source such as an infecting virus. Suitable target sequences should contain long stretches of homopyrimidines or homopurines and the most effective targets contain alternative stretches of each. If the target is double stranded DNA, the most effective targets surround and include the transcriptional regulatory regions. Formation of a triplex between the agent and the target will inhibit the binding of RNA polymerase or other requisite transcriptional regulatory factors which otherwise bind the promoter and upstream regulatory regions.

Triplex agents may be synthesized to be more resistant to cellular and extracellular nucleases by the inclusion of modified nucleotides such as those containing phosphorothioate or methyl phosphonate groups. In the event that such modifications interfere with base pairing, additional adducts, such as derivatives of the base intercalating agent acridine, may be incorporated into the therapeutic agent to restore desirable binding properties to the triplex forming oligonucleotide. Alternatively, if the intracellular target is an mRNA, C-5 propyne pyrimidines may be included in the synthetic oligophosphorothioate agent to increase its binding affinity for mRNA and therefore decrease the concentration required for effectiveness.

The affinity of triplex agents for their respective targets may be assessed by electrophoretic gel retardation assays. The formation of triplex structures will retard migration through an electrophoretic gel. Similarly, the stability of any triplex agent binding to its target can be assessed by UV melting experiments. In these assays triplex agents are mixed with their intended target in vitro and the resulting triplexes are heated (with, for example, a Haake cryothermostat) while monitoring their UV absorbance (with, for example, a Kontron-Uvikon 940 spectrophotometer) (on design of triplex forming oligonucleotides see, for instance, Francois (1999[147])).

Triplex forming agents are simply oligonucleotides designed to form triple helices with the target intracellular nucleic acid. Accordingly, their synthesis, purification and delivery parallels the procedures described herein for other oligonucleotide agents. Each of these processes is commonly known to those skilled in the art.

(d) Homologous Recombination Agents

Binding of factors to foreign polynucleotides (either DNA or RNA), or polynucleotides of disrupted genes, or polynucleotides of a gene in a disrupted or disrupting pathway, or expression of a foreign gene, or a disrupted gene, or a gene in a disrupted or disrupting pathway can also be reduced by mutating the DNA, inactivating, or "knocking out" the gene or its promoter using targeted homologous recombination.

In one exemplary embodiment, a polynucleotide of interest flanked by DNA homologous to the polynucleotide interest (encompassing either the coding or regulatory regions of the polynucleotide) can be introduced into cells carrying the same sequence. Homologous recombination mediated by the flanking sequences disrupts expression of the polynucleotide of interest and result in reduced expression. The technique is frequently used by those skilled in the art to engineer transgenic animals that produce offspring with same disruption. However, the same approach may be used in humans by administering the engineered construct into target cells. Regardless of expression vector platform chosen, it is important to recognize and control for any microcompetition effects that may be elicited by transcriptional enhancers carried by the viral vectors (see also above). Control experiments must be carried out which study the biological activity of a non-recombinant viral vector to reveal any effects its intrinsic enhancers have on the target biological activities.

Nucleic acid agents for homologous recombination are designed to interact with specific cellular DNA targets and undergo recombination. The specificity of the therapeutic agent is conferred by the nucleotide sequences at its termini, they must be complementary to adjacent cellular targets and bind them through Watson-Crick base pairing.

Formulation of these agents involves careful selection of the desired cellular target. The nucleotide sequence of that target must be available in public or private sequence databases. The agent itself may be comprised of a synthetic oligonucleotide or a recombinant nucleic acid carried in a suitable vector.

In one exemplary embodiment, a synthetic oligonucleotide may be used for homologous recombination in order to interrupt the coding sequence or regulatory sequences of the target gene. The oligonucleotide is designed to include nucleotides at its termini which are complementary to those of the target sequence and the central regions may contain any sequence that is neither complementary to the target sequence nor carry an in-frame insertion into the target sequence.

In a related embodiment, a longer sequence of nucleic acid may be used. The sequence of interest, which is intended to either interrupt a cellular gene or insert additional coding capacity into it, is flanked by sequences homologous to the cellular target. That entire DNA fragment is then inserted into an appropriate prokaryotic or viral vector for delivery to the target cells. Once inside the cell the agent will bind to and recombine with the target gene.

(e) Peptide Nucleic Acids

In various embodiments, hybridization of the nucleic acid agents described herein may be enhanced by the substitution of amino acids for the deoxyribose of the nucleic acid backbone. This substitution, thereby creating peptide nucleic acids (see, for example, Hyrup 1996[148]). This modification leads to a reduction of the overall negative charge on the backbone and therefore reduces the need for counter ions to permit sequence-specific hybridization of two strands of negatively charged polynucleotides. Peptide nucleic acids can be synthesized using techniques well known in the art such as the solid phase protocols described by Hyrup and Nielsen (1996, ibid), and Perry-O'Keefe 1996[149], included herein in their entirety by reference.

Oligonucleotides so modified can be used in the same therapeutic techniques as unmodified homologs. They can be used as antisense agents designed to interfere with the expression of a foreign polynucleotide, a disrupted gene, or a gene in a disrupted pathway. Similarly, by virtue of their enhanced hybridization qualities, peptide nucleic acids can be used, for example, as primers for the PCR, for S1 nuclease mapping of single stranded regions and for other enzyme-based techniques. Similarly, peptide nucleic acids may be modified by the addition of lipophilic moieties to enhance the cellular uptake of therapeutic oligonucleotide agents. In related embodiments, peptide nucleotide agents may be synthesized as chimeras comprised of peptide nucleic acids and unmodified DNA. This configuration exploits the advantages of a peptide nucleic acid while the DNA portion of the molecule can serve as a substrate for cellular enzymes.

Peptide Nucleic Acid (PNA) is a DNA analog in which the sugar-phosphate backbone contains a pseudopeptide rather than the sugars characteristic of DNA. Like DNA, PNA agents bind complementary nucleic acid strands thereby mimicking the behavior of DNA. This activity is enhanced by the neutral, rather than negatively charged, backbone of PNA which promotes more tenacious and more specific binding than that of DNA. These are among many favorable properties of PNA and include, in addition, increased stability and exhibit improved hybridization properties compared to their DNA analogs. While the mechanism of PNA action is currently not fully understood, for example PNA-RNA hybrids are not targets for RNase H degradation as are DNA-RNA hybrids, it is likely that they inhibit translation by blocking the binding of RNA polymerase or other critical factors to the target mRNA.

In this light, it is important to select targets which include the translation initiation codon. Other target sites further downstream on the mRNA may be effective at inhibiting translation by interfering with ribosome transit although the role of this activity will need to be determined empirically for each agent developed. In any case the actual mechanism of action, while interesting, is not necessary to ascertain as long as the agent is effective and does not induce undesired side effects.

Homopurines are best targeted by homopyrimidine PNAs with stretches of greater than 8 bp providing suitable targets within double stranded DNA. The synthesis of PNA agents is achieved using automated solid-phase techniques employing Boc-, Fmoc- or Mmt-protected monomers. Alternatively, commercial sources of custom synthetic PNAs, including Applied Biosystems (Foster City, Calif.) may be exploited to minimize in-house expenses and expertise (on design of PNA see, for instance, Nielsen 1999[150]).

(5) Antibodies and Antigens

Another aspect of the invention pertains to the administration of an antibody of interest, equivalent of such antibody, homolog of such antibody, as treatment of a chronic disease.

For example, using standard protocols, one skilled in the art can use immunogens derived from a foreign polynucleotide, foreign polypeptide, disrupted gene, disrupted polypeptide, gene or polypeptide in a disruptive or disrupted pathway, to produce anti-protein, anti-peptide antisera, or monoclonal antibodies (see, for example, Harlow and Lane 1999[151], Sambrook 1989[152]).

Animals which have been injected with an immunogenic agent can serve as sources of antisera containing polyclonal antibodies. Monoclonal antibodies, if desired, may be prepared by isolating lymphocytes from the immunized animals and fusing them, in vitro with immortal, oncogenically transformed cells. Clonal lines from the resulting somatic cell hybrids, or hybridomas, can be used as sources of monoclonal antibodies specific for the immunogen of interest. Techniques for developing hybridomas and for isolating and characterizing monoclonal antibodies are well known in the art (see for instance, Kohler 1975[153] and Zola 2000[154]).

In the context of this invention, "antibody" refers to entire molecules or their fragments which react specifically with polypeptides or polynucleotides of interest, whether they are monospecific, bispecific or chimeras which recognize more than two antigenic determinants. Those skilled in the art employ well known methods for producing specific antibodies and for fragmenting same. While several methods are known to produce antibody fragments, pepsin, for example, is used to treat whole antibody molecules to produce $F(ab)_2$ fragments. These fragments can be further dissociated with chemicals, such as beta mercaptoethanol or dithiothreotol, which reduce intra and intermolecular disulfide bridges resulting in the release of Fab fragments.

Once produced, isolated and characterized, antibodies, or fragments thereof, which bind to antigenic determinants of interest may be used for diagnostic and analytical purposes. For example, they may be used in immunohistochemical assays to assess expression levels of polynucleotides or polypeptides of interest. They may also be employed in other immunoassays, including but not limited to, Western blots, immunoaffinity chromatography, and immunoprecipitation carried out to quantify protein levels in cells or tissues of interest. The assays, individually or together, may also be used by one skilled in the art to measure the concentration a protein of interest before and after therapy to assess therapeutic efficacy.

Similarly, it is common in the art to use specific antibodies to screen libraries of recombinant expression vectors for those expressing a protein or polypeptide of interest. Suitable expression vectors are commonly derived from bacteriophage, including, for example, λgt11 and its derivatives. Identification of expression vectors, from among a library of similar recombinants, can lead to the identification of vectors expressing a polypeptide of interest which may then itself be used in diagnostic or therapeutic assays. In a preferred embodiment, antibodies specific for a particular polypeptide, protein or antigenic determinant carried thereon, will cross react with homologous counterparts from different species to facilitate antibody characterization and assay development.

Antibodies may serve as effective therapeutic agents for the inactivation of specific cellular proteins or for targeting other therapeutic agents to cells expressing particular surface antigens to which an antibody may bind. Polyclonal antibodies are prepared in a suitable host organism, typically rabbit, goat or horse, by injecting the appropriate purified antigen into the host. Following a regimen of repeated challenges by the desired antigen, using protocols well known to those skilled in the art, serum is drawn from the host and assayed for the presence of antibodies. Once a suitable response is detected, additional serum is removed, perhaps leading to exsanguination of the producing organism, and the desired antibodies are purified.

Monoclonal antibodies may be prepared by any number of techniques well known to those skilled in the art. In one exemplary embodiment, cells expressing the desired target antigen are fused with immortalized cells in vitro. The resulting hybridomas are cultured and clonal lines are derived using standard tissue culture techniques. Each resulting clone is assayed for expression of antibodies against the desired antigen, typically but not necessarily by ELISA.

Antibodies may be purified by a number of chromatographic techniques. In one exemplary embodiment, antibodies may be bound to S. aureus protein A cross-linked to a suitable support resin (e.g. sepharose). The crude antibody preparation is slowly applied to the chromatographic column under conditions which permit antibody-protein A interactions. The resin is then washed with several column volumes of buffer to remove adventitiously bound and trapped proteins, leaving only specifically bound antibodies on the column. Those are eluted by washing the column with 100 mM glycine (pH 3.0) and monitoring protein elution spectrophotometrically.

In an alternative embodiment, antibodies are purified by binding to an affinity column comprised of antigen cross-linked to an appropriate solid support. Bound antibodies may be eluted by any of a number of methods and may include the use of an elution buffer containing glycine at low (e.g. 3.0) pH or 3M potassium thiocyanate and 0.5M NH$_4$OH. Due to the varied mechanisms involved with antibody-antigen interactions, the actual optimal elution conditions must determined empirically.

The therapeutic efficacy of polyclonal compared to monoclonal antibodies cannot be predicted. Each has strengths and weaknesses. For example, polyclonal antibodies necessarily target multiple antigenic determinants on the target antigen. This feature may increase reactivity but, at the same time, may decrease specificity. On the other hand, monoclonal antibodies are exquisitely specific for a single antigenic determinant on the target antigen. This specificity greatly reduces the risk of unwanted reactivity with other antigens, and the associated side effects, yet carries the risk that the target antigenic determinant may be inaccessible in the cellular environment, either due to the natural folding of the protein or through interactions with other cellular molecules. In every case, the efficacy of any antibody agent must be determined empirically using a variety of techniques well known to those skilled in the art.

Antibody production is necessarily preceded by the isolation and purification of appropriate antigens. Cellular proteins may be purified by any of a number of techniques well known to those skilled in the art. In one exemplary embodiment, cells expressing the desired antigen are lysed in the presence of non-ionic detergents and the resulting lysate is subjected to purification. That lysate is then fractionated by precipitation in the presence of ammonium sulfate. Sequentially higher concentrations of ammonium sulfate are used to derive protein mixtures which differ by their solubility in ammonium sulfate. Each fraction is then assessed for the presence of the desired antigen.

The fraction carrying the protein of interest is subjected to further purification by any of a number of well known methods. For instance, if an antibody against the protein is available, the protein may be purified by affinity chromatography using a resin of substrate, typically sepharose, dextran or some similar insoluble polymer, to which the antibody is conjugated. The protein mixture containing the desired antigen is exposed to the resin under conditions which promote antibody-antigen interactions. Adventitiously bound proteins are washed from the resin with an excess of binding buffer and the antigens are eluted with buffer containing an ionic detergent such as sodium dodecylsulfate (SDS).

In an alternative embodiment, crude fractions of cellular proteins are further purified using methods well known in the art involving ion exchange or molecular exclusion chromatographic techniques. The purity of antigens isolated by any technique may be assessed by electrophoresis through denaturing polyacrylamide gels followed by visualization by staining.

c) Assay Protocols

One aspect of the invention pertains to assaying the effect of an agent on a molecule of interest, equivalent molecules, or homologous molecules during drug discovery, development, use as treatment, or during diagnosis.

(1) Definitions (a) Molecule of Interest

The term "molecule of interest" is understood to include, but not limited to, p300/cbp, p300/cbp polynucleotides, p300/cbp factors, p300/cbp regulated genes, p300/cbp regulated polypeptides, p300/cbp factor kinases, p300/cbp factor phophatases, p300/cbp agents, foreign p300/cbp polynucleotides, p300/cbp viruses, disrupted genes, disrupted polypeptides, genes in disrupted pathways, polypeptides in disrupted pathways, genes in disruptive pathways, polypeptides in disruptive pathways.

Every gene and protein mentioned in this invention is uniquely defined by its sequence as published in public databases. See, for instance, the sequences in the nucleotide and protein sequence databases at NCBI (also known as Entrez, the name of the search and retrieval system), GenBank, the NIH genetic sequence database, DDBJ, the DNA DataBank of Japan, EMBL, the European Molecular Biology Laboratory database (GenBank, DDBJ and EMBL comprise the International Nucleotide Sequence Database Collaboration), SWISS-PROT, the protein knowledgebase, and TrEMBL, the computer-annotated supplement to SWISS-PROT (see also the search and retrieval system Expasy), PROSITE, the database of protein families and domains, and TRANSFAC, the database of transcription factors. By a gene it is meant the coding and non coding regions, the promoters, enhancers, and the 5' and 3' UTRs. Published sequences are considered standard information and are well known in the art.

(b) Equivalent Molecules

The term "equivalent molecules" is understood to include molecules having the same or similar activity as the molecule of interest, including, but not limited to, biological activity and chemical activity, in vitro or in vivo.

(c) Homologous Molecules

The term "homologous molecules" is understood to include molecules with the same or similar chemical structure as the molecule of interest (see exemplary embodiments above).

The following section presents standard assays which can be used, in conjunction with the assays in the new elements section, to test the effect of an agent on a molecule of interest.

(d) During

The term "during drug discovery, development, use as treatment, or during diagnosis" is understood to include, but not be limited to, drug screening, rational design, optimization, in laboratory or clinical trials, in vitro or in vivo (see exemplary embodiment below).

(2) Assaying Protein Concentration (a) UV Absorbance

In one exemplary embodiment, cellular protein concentration is measured by virtue of its absorbance of ultraviolet light at the wavelength of 280 nm (Ausubel 1999[155]). To calibrate the reagents used, and to validate the spectrophotometer, a standard curve is established using protein solutions of known concentration. Typically solutions of bovine serum albumin, a commonly available protein, are used to establish the standard curve. Cells are lysed in a detergent-rich buffer to liberate membrane associated and intracellular proteins. Following lysis, insoluble materials are removed by centrifugation. The absorbance of UV light by the supernatant, which contains soluble proteins of unknown concentration, is then measured and compared to the standard curve. Comparison of the data obtained from the cellular extracts with those represented by the standard curve provides an indication of cellular protein concentration.

(b) Bradford Method

In another exemplary embodiment, protein concentration is determined using the Bradford method (Sapan 1999[156], Ausubel 1999, Ibid). A standard curve is constructed using solutions of known protein concentration mixed with coomassie brilliant blue. Following a brief incubation at room temperature, the absorbance of light at 595 nm is measured and a standard curve is constructed. Cells are lysed as described above, the lysate is mixed with coomassie brilliant blue and the absorbance measured in a manner identical to that of the standard curve. Comparison of the values obtained from the cellular extract with those of the solutions of known concentration reveals the concentration of cellular proteins.

(c) Immunoaffinity Chromatography

To measure concentration of a specific cellular protein, for instance, p300, GABP or CBP, additional steps are employed to purify the protein away from other cellular proteins. One exemplary embodiment involves the use of specific antibodies targeted against the protein of interest to remove it from the cellular lysate. Specific antibodies, for instance, anti-p300, anti-GABP or anti-CBP, are chemically bound to a resin and contained within a vertical glass or plastic column. Cell lysate is passed over that resin to permit antibody-antigen interactions, thereby allowing the protein to bind to the immobilized antibodies. Efficient removal of the protein of interest from the cell lysate is accomplished by using an excess of antibody. Protein bound to the column is removed which releases the bound protein. The eluted protein is collected and its concentration determined by an assay for protein concentration such as those exemplified above.

(3) Assaying mRNA Concentration (a) UV Absorbance

In certain embodiments, RNA concentration is measured by absorption of ultraviolet light at a wavelength of 260 nm (Manchester 1995[157], Davis 1986[158], Ausubel 1999, Ibid). RNA is purified from cells by first lysing the cells in a detergent rich buffer. Proteins in the cellular lysate are degraded by incubation overnight at 65° C. with proteinase K. After enzymatic degradation, proteins are extracted from the solution by mixing with phenol/chloroform/isoamyl alcohol followed by extraction with chloroform/isoamyl alcohol. Nucleic acids in the resulting protein deficient solution are precipitated by addition of salt, typically sodium acetate or ammonium acetate, and ethanol. After a brief incubation of the mixture at −20° C., the insoluble nucleic acids are removed by centrifugation, dried, and redissolved in a sterile, RNase free solution of Tris and EDTA. Contaminating DNA is removed from the lysate by treatment with RNase-free DNase I. Degraded DNA is removed by precipitation of the intact RNA with salt and ethanol. The dried, purified RNA is dissolved in Tris-EDTA and quantified by virtue of its absorbance of light at 260 nm. Since the molar extinction coefficient of RNA at 260 nm is well known, the concentration of RNA in the solution can be determined directly.

(b) Northern Blot

The concentration of a particular RNA species can also be determined. In one exemplary embodiment, the amount of mRNA which encodes a protein of interest, for instance, p300, GABP, CBP, within a population of cells is measured by Northern blot analysis (Ausubel 1999, Ibid, Gizard 2001[159]). Total cellular RNA is isolated and separated by electrophoresis through agarose under denaturing conditions, typically in a gel containing formaldehyde. The RNA is then transferred to, and immobilized upon a charged nylon membrane. The membrane is incubated with a solution of detergent and excess of low molecular weight DNA, typically isolated from salmon sperm, to prevent adventitious binding of the gene specific, for instance, p300-, GABP-, CBP-specific, radiolabeled DNA probe to the membrane. Radiolabeled cDNA probes representing the protein, e.g., p300, GABP, CBP, transcript are then hybridized to the membranes and bound probe is visualized by autoradiography.

(c) Reverse Transcriptase—Polymerase Chain Reaction (RT-PCR)

In another exemplary embodiment, the amount of mRNA encoding a protein of interest, for instance, p300, GABP, CBP, expressed by a population of cells is measured by first isolating RNA from cells and preparing cDNA by binding oligo deoxythymidine (dT) to the polyadenylated mRNA within the prepared RNA. Reverse transcriptase is then used to extend the bound oligo dT primers in the presence of all four deoxynucleotides to create DNA copies of the mRNA. The cDNA population is then amplified by the polymerase chain reaction in the presence of oligonucleotide primers specific for the sequence of the gene or RNA of interest and Taq DNA polymerase. The amplification products can be visualized by gel electrophoresis followed by staining with ethidium bromide and exposure to ultraviolet light. Quantification can be achieved by adding a radiolabeled deoxynucleotide to the PCR reaction. Radiolabel incorporated into the amplification products is visualized by autoradiography and quantified by densitometric analysis of the autoradiograph or by direct phosphorimager analysis of the electrophoretic gel.

(d) S1 Nuclease Protection

In a related exemplary embodiment, expression of RNA encoding a protein of interest, for instance, p300, GABP, CBP, can be assessed by hybridizing isolated cellular RNA with a radiolableled synthetic DNA sequence homologous to the 5' terminus of the RNA of the protein of interest. The synthetic deoxyribonucleotide, less than 40 nucleotides in length, is labeled at it 5' end with T4 polynucleotide kinase and $\gamma$-$^{32}$ P ATP. Once the oligonucleotide is bound to the RNA, the mixture is incubated in the presence of the single strand-specific nuclease S1. Any unhybridized, and therefore single stranded, molecules of RNA or DNA are degraded, leaving the DNA-RNA hybrids of the protein of interest intact. The undegraded hybrids are removed from the solution by precipitation with ammonium acetate and ethanol and resolved by nondenaturing gel electrophoresis. Radiolabeled bands on the gel are then visualized by autoradiography. The radiolabel can be quantified by densitometric analysis of the autoradiographs or by phosphorimager analysis of the electrophoretic gels themselves.

(4) Assaying Polynucleotide Copy Number (a) S1 Nuclease Protection

This same technique can be used to quantify the level of any nucleic acid, naturally expressed or exogenous, within a population of cells. In every case the sequence of the single stranded synthetic oligonucleotide must be designed so that it is complementary to the 5' terminal sequence of the species to be measured.

(b) Real Time PCR

In another exemplary embodiment, DNA copy number can be measured using real time PCR (Heid 1996[160]). This technique employs oligonucleotides doubly labeled. At the 5' ends they carry a reporter dye that fluoresces upon excitation by the appropriate wavelength of light. At the 3' end they carry a quencher dye that suppresses the fluorescence of the first dye. These oligonucleotides are prepared so that their sequence is complementary to the region of interest which lies between the forward and reverse PCR primers. Once hybridized to the DNA sequence of interest, the close proximity of the quencher dye and the fluorescent dye suppresses the fluorescent emissions of the reporter dye. However, during the process of PCR, Taq polymerase cleaves the reporter dye from the oligonucleotide and releases it. Once removed from the nearby quencher dye, fluorescence is permitted. Free fluorescent dye is quantified with a fluorimeter and is directly related to the number of molecules of interest present prior to PCR.

(5) Detection of Binding (a) General

In one exemplary embodiment, an assay to identify compounds that bind to a polynucleotide or polypeptide of interest involves binding of a test compound to wells of a microtiter plate by covalent or non-covalent binding. For instance, the assay may anchor a specific test compound to a microtiter plate substrate using a mono or polyclonal immobilized antibody. A solution of the test compound can also be used to coated the solid surface. Then, the nonimmobilized polynucleotide or polypeptide of interest may be added to the surface coated wells. After sufficient time is allowed for the reaction to complete, the residual components are removed by, for instance, washing. Care should be taken not to remove complexes anchored on the solid surface. Anchored complexes may be detected by several methods known in the art. For instance, if the nonimmobilized polynucleotide or polypeptide of interest, or test compound were labeled before the reaction, the label may be used to detect the anchored complexes. If the components were not prelabeled, a label may be added during or after complex formation, for instance, an antibody directed against the nonimmobilized polynucleotide or polypeptide of interest, or test compound, can be added to the surface coated wells.

In a variation of this assay, the polynucleotide or polypeptide of interest is anchored to the a solid surface and the nonimmobilized test compound is added to the surface coated wells.

In another variation of this assay, the reactions are performed in a liquid phase, and the complexes are removed from the reaction mixture by immunoaffinity chromatography, or immunoprecipitation, as described herein.

(b) Detection of Binding to DNA

In one exemplary embodiment, DNA fragments carrying a known, or suspected binding domain for a polypeptide of interest, for instance, p300, GABP, etc., are purified by gel electrophoresis and labeled with T4 polynucleotide kinase in the presence of $\gamma^{32}$ P-ATP (Bulman et al. 2001). Labeled DNA is then added to a solution containing the polypeptide of interest under conditions, ionic and thermal, which permit formation of DNA-polypeptide complexes. The solution is then maintained for a period of time sufficient for the reaction to complete. Following completion, the mixture is separated by electrophoresis through nondenaturing polyacrylamide in parallel to labeled, but otherwise unreacted test DNA. Following electrophoresis, the labeled DNA is detected by autoradiography or by phosphorimager analysis. Formation of complexes is detected by the shift in electrophoretic mobility (see also below).

The assay detects polypeptide-DNA complexes formed by direct binding of the polypeptide of interest with DNA, or by indirect binding through intermediary polypeptides, as long as the intermediary polypeptides are present in the reaction mixture. Further, the magnitude of the gel shift provides a semi-quantitative measure of the relative concentration of the polypeptide-DNA binding in the assay mixture. As such, changes in concentration can also be detected.

(i) Affinity Chromatography

In one exemplary embodiment, binding of a polypeptide of interest, that is, disrupted polypeptide, or polypeptide in a disrupted or disruptive pathway, such as p300, GABP, CBP, to DNA is measured by first expressing fragments of the polypeptide of interest as GST (glutathione sulfonyl transferase) fusion proteins in *E. coli* (Gizard 2001, Ibid). The expressed polypeptides are then bound to glutathione coupled sepharose. Radiolabeled DNA fragments, carrying $^{32}$P, representing the polypeptide binding site, are incubated with protein-bead complexes and subsequently washed three times to remove adventitiously bound DNA. Any DNA bound to the immobilized polypeptide of interest are released by boiling in presence of the ionic detergent SDS. Liberated radiolabeled DNA is quantified by liquid scintillation counting, or by direct measurement of Cerenkov radiation.

(ii) Electrophoretic Gel Mobility Shift Assay

In another exemplary embodiment, binding of a polypeptide of interest, or a group of polypeptides to DNA is assessed by electrophoretic gel mobility shift assay (Gizard 2001, Ibid, Ausubel 1999, Ibid, Nuchprayoon 1999[161]). Radiolabeled DNA carrying the polypeptide binding site, for instance, the p300 binding site, or N-box, is mixed with the recombinant polypeptide, for instance, p300, GABP, expressed as GST fusion protein. Subsequent resolution by electrophoresis through nondenaturing polyacrylamide gels in parallel with labeled DNA alone, reveals a shift in electrophoretic mobility only if the polypeptide is bound to DNA in the DNA/polypeptide mixtures. If the DNA binding site is unknown, or one is suspected to be carried in a collection of DNA fragments, this assay can be performed to test for, and potentially affirm the presence of such a binding site.

(6) Detection of Binding Interference

A polynucleotide or polypeptide of interest may bind with one or many cellular or extracellular proteins in vivo. Compounds that interfere with, or disrupt the binding may include, but are not limited to, antisense oligonucleotides, antibodies, peptides, and similar molecules.

In one exemplary embodiment, binding interference of a test compound is assessed by adding the compound to a mixture containing a polynucleotide or polypeptide of interest and a binding partner. After enough time is allowed for the reaction to be completed, the complex concentration in the test reaction mixture is compared to a control mixture prepared without the test compound, or with a placebo. A decreased concentration in the test reaction indicates interference. Reactants may be added at different orders regardless of the method used. For example, a test compound may be added to the reaction mixture before adding the polynucleotide or polypeptide of interest and their binding partners, or at the same time. A test compound that can disrupt an already formed complex, for instance, by displacing a complex component, can be added to the reaction mixture after complex formation. The interference assay can be conducted in two ways, in liquid, or in solid phases, as described above.

In another embodiment, a polynucleotide or polypeptide of interest is prepared for immobilization by fusion to glutathione-S-transferase (GST), while maintaining the binding capacity of the fusion protein. Another complex component, a cellular polynucleotide or polypeptide, or extracellular protein, can be purified, and then utilized in developing a monoclonal antibody using methods well known in the art. The GST-polynucleotide fusion protein is coupled to glutathione-agarose beads and exposed to the other complex component in the presence or absence of a test compound. After sufficient time has been allowed for the reaction to complete, unbound components are removed, for instance, by washing, and the labeled monoclonal antibody is added. Bound radiolabeled antibody is then measured to quantify the extent of complex formation. Inhibition of complex formation by a test compound decreases measured radioactivity. As above, a test compound capable of complex disruption can also be added after complex formation.

In one variation of the assay, the fusion protein is mixed with the other complex component in liquid, that is, without solid glutathione-agarose beads.

In another variation of the assay, peptide fragments of the binding domains, instead of full length complex components are used. Several methods well known in the art can be used to identify and isolate binding domains. For instance, one method entails mutating a gene and screening for a disruption in normal binding of the polypeptide encoded by the gene by co-immunoprecipitation or immunoaffinity. If the polypeptide shows disrupted binding, analysis of the gene sequence can reveal the binding domain, or the region of the polypeptide involved in binding. Another approach partially proteolyzes a labeled polypeptide anchored to a solid surface. Non bound fragments are removed by washing leaving a labeled polypeptide comprising the binding domain immobilized on the solid surface. The polypeptide fragments bound to the immobilized proteins are than isolated and analyzed by amino acid sequencing, using for instance the Edman degradation procedure (Creighton 1983[162]). Another approach expresses specific fragments of a polynucleotide, or gene, and tests the fragments for binding activity.

In another embodiment, an assay uses a complex with one component labeled. However, binding to the complex quenches the signal generated by the label (see, for instance, U.S. Pat. No. 4,109,496). A test compound which disrupts the complex, for instance, by displacing a part of the complex, restores the signal. This assay can be used to identify compounds which either interfere with complex formation, or disrupt an already formed complex.

Specifically, a test compound can interfere with binding between a disrupted gene or polypeptide, or a gene or polypeptide in a disruptive or disrupted pathway, for instance, a microcompeted or mutated gene or polypeptide, and their binding partner. The assay may be especially useful in identifying compounds capable of interfering in binding reactions between foreign polynucleotides and cellular polypeptides without interfering in binding between cellular polynucleotide and cellular polypeptides. The assay is also especially useful in identifying compounds capable of interfering in binding between mutant cellular polynucleotide or polypeptide and normal cellular polynucleotide or polypeptide without interfering in binding between normal polynucleotide or polypeptides.

(7) Identification of a Polypeptide Bound to DNA or Protein Complex (a) Immunoprecipitation In one exemplary embodiments, the identity of a bound polypeptide, for instance, p300, GABP, CBP, is confirmed by reacting antibodies specific to the polypeptide of interest with polypeptides bound to DNA. For example, p300-specific antibodies are mixed with the polypeptide-DNA complexes and incubated overnight at 4° C. Immune complexes are then precipitated by the addition of a secondary antibody directed against the primary p300-specific antibody. Precipitated antibody-antigen complexes are resolved by denaturing gel electrophoresis and the constituent proteins are visualized by staining with coomassie brilliant blue.

In a related exemplary embodiment, the interaction between a polypeptide of interest, for instance, p300, GABP, CBP, and other cellular proteins, such as transcription factors, may be detected by co-immunoprecipitation of the polypeptide of interest with antibodies specific to the polypeptide, for instance, p300-specific antibodies. For example, in the case of p300, cellular protein extracts are incubated with purified p300-GST fusion proteins to enable protein-protein interactions. p300-specific antibodies are then added and the mixture is incubated overnight at 4° C. Immune complexes are precipitated by addition of a secondary antibody directed against the primary p300 antibodies and the precipitates are resolved by electrophoresis on denaturing polyacrylamide gels. Proteins are subsequently detected by staining with coomassie brilliant blue.

(b) Antibody Supershift Assay

In a related exemplary embodiment, DNA-protein complexes are detected by electrophoretic gel mobility shift assay (Gizard 2001, Ibid, Ausubel 1999, Ibid). Radiolabeled DNA carrying the polypeptide binding site, for instance, p300 binding site, or N-box, is mixed with a recombinant polypeptide, for instance, p300, or GABP, expressed as GST fusion protein. Subsequent resolution by electrophoresis through nondenaturing polyacrylamide gels in parallel with labeled DNA alone, reveals a shift in electrophoretic mobility only if the polypeptide is bound to DNA in the DNA/polypeptide mixture. To identify the bound polypeptide, a specific antibody is reacted to the DNA/polypeptide mixture prior to electrophoresis. Bound antibody molecules cause a further change in gel mobility, namely a supershift, and serve to identify the polypeptide bound to DNA.

(8) Identification of a DNA Consensus Binding Site (a) PCR and DNA Sequencing

In one exemplary embodiment, DNA fragments are prepared containing potential polypeptide binding sites, either wild-type or variants, flanked by DNA fragments of known nucleotide sequence. The fragments are then reacted with the polypeptide-GST fusion proteins immobilized on sepharose beads. After washing to remove adventitiously bound DNA, bound fragments are eluted by heating in presence of a detergent. The eluted fragments are amplified by the polymerase chain reaction (PCR) using primers specific for the flanking DNA sequences. The nucleotide sequence of the amplification products is then determined by any sequencing method known in the art, for instance, the dideoxy chain termination sequencing method of Sanger (Sanger 1977[163]), using as sequencing primer one of the two PCR primers. Several sequence variants of the binding site are likely to be identified. Together they can be used to establish a consensus DNA sequence for the polypeptide binding site.

(9) Detection of a Genetic Lesion

Existence of a genetic lesion can be determined by observing one or more of the following irregularities.

1. Deletion of at least one nucleotide from a disrupted gene, or gene in a disrupted pathway.

2. Addition of at least one nucleotide to a disrupted gene, or a gene in a disrupted pathway.

3. Substitution of at least one nucleotide to a disrupted gene, or gene in a disrupted pathway.

4. Irregular modification of a disrupted gene, or gene in a disrupted pathway, such as change in DNA methylation patterns.

5. Gross chromosomal rearrangement of a disrupted gene, or gene in a disrupted pathway, for instance, translocation.

6. Allelic loss of disrupted gene, or gene in a disrupted pathway.

7. Different than wild-type mRNA concentration of a disrupted gene, or gene in a disrupted pathway.

8. Irregular splicing pattern of mRNA transcript of a disrupted gene, or gene in a disrupted pathway.

9. Irregular post-transcriptional modification of an mRNA transcript other than splicing, for instance, editing, capping or polyadenylation, of a disrupted gene or gene in a disrupted pathway.

10. Different than wild-type concentration of a disrupted polypeptide, or polypeptide in a disrupted pathway.

11. Irregular post-translational modification of a disrupted polypeptide, or a polypeptide in a disrupted pathway.

Many assays are known in the art for detection of the above, or other irregularities associated with a genetic lesion. Consider the following exemplary assays. Also consider the exemplary assays discussed in the following reviews on detection of genetic lesions, Kristensen 2001[164], Tawata 2000[165], Pecheniuk 2000[166], Cotton 1993[167], Prosser 1993[168], Abrams 1990[169], Forrest 1990[170].

(a) Sequencing

In one exemplary embodiment, a polynucleotide of interest can be sequenced using any sequencing techniques known in the art to reveal a lesion by comparing the test sequence to wild-type control, known mutant sequence, or sequences available in public databases.

An introduction to sequencing is available in Graham 2001[171]. Exemplary sequencing protocols are available in Rapley 1996[172]. Recent sequencing methods are available in Marziali 2001[173], Dovichi 2001[174], Huang 1999[175], Schmalzing 1999[176], Murray 1996[177], Cohen 1996[178]; Griffin 1993[179]. Automated sequencing methods are available in Watts 2001[180], MacBeath 2001[181], Smith 1996[182]. For classical sequencing methods see Maxam 1977[183], Sanger 1977 (Ibid).

(b) Restriction Enzyme Cleavage Patterns

In another exemplary embodiment, patterns of restriction enzyme cleavage are analyzed to reveal lesions in a polynucleotide of interest. For example, sample and control DNA are isolated, amplified, if necessary, digested with one or several restriction endonucleases, and the fragments separated by gel electrophoresis. Sequence specific ribozymes are then used to detect specific mutations by development or loss of a ribozyme cleavage site.

(c) Protection from Cleavage Agents

In another exemplary embodiment, cleavage agents, such as certain single-strand specific nucleases, hydroxylamine, osmium tetroxide or piperidine, are used to detect mismatched base pairs in nucleic acid hybrids comprised of either RNA/RNA or RNA/DNA duplexes. Wild-type and test DNA or RNA, with one or the other molecule labeled with radioactivity, are mixed under conditions permitting formation of heteroduplexes between the two species. Following hybridization, the duplexes formed are treated with an agent capable of cleaving single, but not double stranded nucleic acids. Examples include, but are not limited to S1 nuclease, piperidine, hydroxylamine and RNase H, in the case of RNA/DNA heteroduplexes. Since mismatches between wild-type and mutant oligonucleotide result in single stranded regions, mismatch sites are susceptible to digestion. Once cleaved, the nucleic acid fragments are separated according to size by native polyacrylamide gel electrophoresis. Genetic lesion are detected by, for instance, observing different fragment sizes in test relative to wild-type DNA or RNA.

Examples of such assay in practice are available in Saleeba 1992[184], Takahashi 1990[185], Cotton 1988[186], Myers 1985A[187], Myers 1985B[188].

(d) Mismatched Base Pairs Recognition

In another exemplary embodiment, mismatch cleavage reactions are carried out using one or more proteins capable of recognizing mismatched base pairs. The proteins are typically components of the naturally occurring DNA mismatch repair mechanism. In a preferred embodiment, the mutY enzyme derived from *E. coli* cleaves the adenine at a G/A mismatch (Xu 1996[189]). The enzyme thymidine DNA glycosylase, isolated from the human cell line HeLa, cleaves the thymidine at G/T mismatches (Hsu 1994[190]). In practice, a probe is used comprising the wild-type sequence of interest. The probe is hybridized to DNA, or cDNA corresponding to mRNA of interest. Once duplex formation has reached completion, a DNA mismatch repair enzyme is added to the reaction, and the products of the cleavage are detected by, for instance, separating reactants by denaturing polyacrylamide gel electrophoresis.

(e) Alterations in Electrophoretic Mobility

In another exemplary embodiment, variations in electrophoretic mobility are used to identify genetic lesions, by standard techniques, such as single strand conformation polymorphism (SSCP) (Miterski 2000[191], Jaeckel 1998[192], Cotton 1993, Ibid, Hayashi 1992[193]). Dilute preparations of radiolabeled single-stranded DNA fragments of test and control nucleic acids, separately, are denatured by heat and permitted to renature slowly. Upon renaturation, single stranded nucleic acids in the dilute solutions form secondary structures. Each molecule forms internal base paired regions depending on each molecule sequence. Consequently, wild-type and mutant sequences, otherwise identical except for regions of mutation, form different secondary structures. Each preparation is separated in adjacent lanes by electrophoresis through native polyacrylamide gels while preserving the secondary structure formed during renaturation. Alterations in electrophoretic mobility reveal differences between wild-type and mutant oligonucleotides as small as single nucleotide differences. Following electrophoresis the radiolabeled nucleic acids are detected by autoradiography or by phosphorimager analysis. A variation of this assay employs RNA rather than DNA.

In a related exemplary embodiment, wild-type and mutant DNA molecules are separated by electrophoresis through polyacrylamide gels containing a gradient of denaturant. The method, termed "denaturing gradient gel electrophoresis," (DGGE) (Myers 1985B, Ibid) is commonly used to detect differences between similar oligonucleotides. Prior to analysis, test DNA is often modified by addition of up to 40 base pairs of GC rich DNA through PCR. The relatively stable region, termed "GC clamp," ensures only partial denaturation. A variation of the assay employs a temperature rather than chemical gradient of denaturant.

(f) Selective Oligonucleotide Hybridization

In another embodiment, selective hybridization involves the use of synthetic oligonucleotide primers prepared to carry a known mutation in a central position. Primers are then mixed with test DNA under conditions permitting hybridization for perfectly matched molecules (Lipshutz 1995[194], Guo 1994[195], Saiki 1989[196]). The allele specific oligonucleotide (ASO) hybridization method can be used to test a single mutation per reaction mixture, or many different mutations if the ASO is first immobilized on a suitable membrane. The technique, termed "dot blotting," permits rapid screening of many mutations when nonimmobilized DNA is first radiolabeled to permit visualization of the immobilized hybrids.

(g) Allele Specific Amplification

Under certain conditions, polymerase extension occurs only if there is a perfect match between primer and the 3' terminus of the 5', left-most or upstream region of a sequence of interest. Therefore, in another embodiment, allele specific amplification, a selective PCR amplification based assay, a synthetic oligonucleotide primer is prepared carrying a mutation at the center, or extreme 3' end of the primer, such that mismatch between primer and test DNA prevents, or reduces efficiency of the polymerase extension during amplification (Efremov 1991[197], Gibbs 1989[198]). A mutation in the test DNA is detected by a change in amplification product concentration relative to controls, or, in special cases, by the presence or absence of amplification products.

A variation of the assay introduces a novel restriction endonuclease recognition site in the expected mutation region to permit detection by restriction endonuclease cleavage of the amplification products (see also above).

(h) Protein Truncation Test

Another embodiment uses the protein truncation test (PTT). If a mutation introduces a premature translation stop site, PTT offers an effective detection assay Geisler 2001[199], Moore 2000[200], van der Luijt 1994[201], Roest 1993[202]). In this assay, RNA is isolated from sample cells or tissue and converted to cDNA by reverse transcriptase. The sequence of interest is amplified by the PCR, and the products are subjected to another round of amplification with a primer carrying a promoter for RNA polymerase, a sequence for translation initiation. The products of the second round of PCR are subjected to transcription and translation in vitro. Electrophoresis of the expressed polypeptides through sodium dodecyl sulfate (SDS) containing polyacrylamide gels reveals the presence of truncated species arising from the presence of premature translation stop sites. In a variation of this assay, if the sequence of interest is contained within a single exon, DNA rather than cDNA can used as PCR amplification template.

(i) General Comments

Any tissue or cell type expressing a sequence of interest may be used in the described assays. For instance, bodily fluids, such as blood obtained by venipuncture or saliva, or non-fluid samples, such as hair, or skin, may be used. Samples of fetal polynucleotides collected from maternal blood, amniocytes derived from amniocentesis, or chorionic villi obtained for prenatal testing, can also be used.

Pre-packaged diagnostic kits containing one or more nucleic acid probes, primer set, and antibody reagent may be useful in performing the assays. Such kits are designed to provide an easy to use instrument especially suitable for use in the clinic.

The assays may also be applied in situ directly on the tissue to be tested, fixed or frozen. Typically, such tissue is obtained in biopsies, or surgical procedures. In situ analysis precludes the need for nucleic acid purification.

While the exemplary assays described so far primarily permit the analysis of one nucleic acid sequence of interest, they may be also used to generate a profile of multiple sequences of interest. The profile may be generated, for example, by employing Northern blot analysis, a differential display procedure, or reverse transcriptase-PCR (RT-PCR).

In addition to nucleic acid assays, antibodies directed against a mutated polynucleotide, or polypeptide product of a mutated polynucleotide may be used in various assays (see below).

(10) Assaying Methylation Status of DNA (a) Sodium Bisulfite Method

In one exemplary embodiment, the methylation status of DNA sequences can be determined by first isolating cellular DNA, and then converting unmethylated cytosines into uracil by treatment with sodium bisulfite, leaving methylated cytosines unchanged. Following treatment, the bisulfite is removed, and the chemically treated DNA is used as a template for PCR. Two parallel PCR reactions are performed for each DNA sample, one using primers specific for the DNA prior to bisulfite treatment, and one using primers for the chemically modified DNA. The amplification products are resolved on native polyacrylamide gels and visualized by staining with ethidium bromide followed by UV illumination. Amplification products detected from the sodium bisulfite treated samples indicate methylation of the original sample.

Specifically, this assay can be used to asses the methylation status of DNA binding sites of a polypeptide of interest, such as GABP, p300, CBP, etc.

(11) Assaying Protein Phosphorylation (a) Western Blot with Antiphosphotyrosine

In one exemplary embodiment, protein phosphorylation is measured using antiphosphotyrosine antibodies (for instance, antibodies available from Santa Cruz Biotechnology, catalog numbers sc-508 or sc-7020). Cultured cells are lysed by boiling in detergent-containing buffer. Proteins contained in the cell lysate are separated by electrophoresis through SDS polyacrylamide gels followed by transfer to a nylon membrane by electrophoresis, a process termed electroblotting (Burnett 1981[203]). Prior to incubation with antibody, the membrane is incubated with blocking buffer containing the nonionic detergent Tween 20 and nonfat dry milk as a source of protein to later block adventitious binding of specific antibodies to the nylon membrane. The immobilized proteins are then reacted with anti-phosphotyrosine antibodies and visualized after reaction with a secondary antibody conjugated to horse radish peroxidase. Exposure to hydrogen peroxide in presence of the chromogenic indicator diaminobenzidine produces visible bands where secondary antibodies are bound, thereby enabling their localization.

A variation of this assay can be performed with antibodies directed against phosphothreonine (for instance, those available from Santa Cruz Biotechnology, catalog number sc-5267) or a host of phosphorylated molecules. Sources of available phosphoprotein specific antibodies include, but are not limited to, Santa Cruz Biotechnology of Santa Cruz, Calif., Calbiochem of San Diego, Calif. and Chemicon International, Inc. of Temecula, Calif.

The protein phosphorylation detection assays may be employed before and/or after treatment with an agent of interest to detect changes in phosphorylation status of a polypeptide, or group of polypeptides. Moreover, detection of changes in phosphorylation status of polypeptides of interest may be used to monitor efficacy of a therapeutic treatment or progression of a chronic disease.

(b) Immunoprecipitation

In one complementary embodiment, the relative levels of phosphorylated and nonphosphorylated forms of any particular protein may be measured. The levels of the phosphorylated forms are measured as described above. Nonphosphorylated proteins are measured by first immunoprecipitating all forms of the protein of interest with a specific antibody directed toward that protein. The immune complexes are then analyzed by Western blotting as described. Comparison of the levels of total protein of interest to those of the phosphorylated forms provide some insight into the relative levels of each form of the polypeptide of interest.

(12) Assaying Gene Activation and Suppression (a) Co-transfection with Report Gene to Identify Transactivators In one exemplary embodiment, interactions between regulatory proteins and a DNA sequence of interest can be revealed through co-transfection of two recombinant vectors. The first vector carries a full length cDNA for the regulatory factor driven by a promoter known to be active in the transfected cells. The second recombinant vector carries a reporter gene driven by the DNA sequence of interest. Examples of suitable reporter genes include chloramphenicol acetyltransferase (CAT), luciferase or β-galactosidase (Virts 2001[204]). Detection of reporter gene expression by methods known in the art (see examples below) indicates transactivation of the DNA sequence of interest by the regulatory factor.

Transfection of appropriate recombinant vectors can be mediated either with calcium phosphate (Chen 1988[205]) or DEAE-dextran (Lopata 1984[206]). In one exemplary embodiment, exponentially growing cells are exposed to precipitated DNA. A DNA solution, prepared in 0.25 M $CaCl_2$ is added to an equal volume of HEPES buffered saline and incubated briefly at room temperature. The mixture is then placed over cells and incubated overnight to permit DNA adsorption and absorption into the cells. The next day the cells are washed and cultured in complete growth medium.

In a related exemplary embodiment, calcium chloride precipitation is replaced with DEAE-dextran as a carrier for the DNA to be transfected. Growth medium is made 2.5% with respect to fetal bovine serum (FBS) and 10 μM with respect to chloroquine. The medium is prewarmed, and DNA is added prior to addition of DEAE-dextran. The mixture is then added to exponentially growing cells, and incubated for 4 hours to allow DNA adsorption. The transfection medium is replaced by a 10% solution of DMSO causing the DNA to enter the cells. The cells are incubated for 2-10 hours. The DMSO solution is then replaced by growth medium, and the cells are incubated until assayed for exogenous gene expression.

CAT

Detection of CAT gene expression is achieved by mixing lysates of the cells in which the reporter gene has been co-transfected along with a recombinant vector carrying the putative activating factor with $^{14}C$-labeled chloramphenicol (Gorman 1982[207]).

Acetylated and unacetylated forms of the compound, the latter resulting from enzymatic degradation of the substrate by expressed CAT, are separated by thin layer chromatography and visualized by autoradiography. Quantitation of each radiolabeled species is attained by densitometric analysis of the autoradiograph, or by direct phosphorimager analysis of the chromatograph.

Luciferase

Detection of expressed luciferase is achieved by exposure of transfected cell lysates to the luciferase substrate luciferin in presence of ATP, magnesium and molecular oxygen (Luo 2001[208]). The presence of luciferase results in transient release of light detected by luminometer.

β-Galactosidase

Detection of β-galactosidase gene expression is achieved by mixing cell lysates with a chromogenic substrate for the enzyme, such as o-nitrophenyl-β-D-galactopyranoside (ONPG), or a chemiluminescent substrate containing 1,2 dioxetane. Products of the catalytic degradation of the chromogenic substrate are easily visualized, or alternatively, quantified by spectrophotometry, while the products of the chemiluminescent substrate are detected by luminometer. The latter assay is especially sensitive and can detect minute levels, or minute changes in levels of β-galactosidase reporter gene expression.

These assays were applied to demonstrate binding of GABP to the promoter regions of a number of genes including the retinoblastoma gene (Sowa 1997[209]), CD 18 (Rosmarin 1998[210]), cytochrome C oxidase Vb (Sucharov 1995[211]) and the prolactin gene (Ouyang 1996[212]).

(b) Co-Transfection with Reporter Gene to Identify Trans-acting Repressors

These assays can be applied to assess trans-acting factors which potentially repress rather than stimulate reporter gene expression. In this embodiment, putative repression factors are expressed from a recombinant vector in cells which carry a reporter gene driven by a constitutively active promoter which may interact with the repression factor. The assays described above are applied to determine whether expression of the repression factor reduces reporter gene activity.

(13) Assaying Gene Expression Levels (a) Northern Blot Analyses

In one exemplary embodiment, the relative expression levels of a gene of interest are measured by Northern blot analysis (Ausubel 1999, Ibid). RNA is isolated from untreated cells and cells after treatment with an agent expected to modulate gene expression. The RNA is separated by electrophoresis through a denaturing agarose gel, typically incorporating the denaturant formaldehyde, and transferred to a nylon membrane. Immobilized RNA is hybridized to a radiolabeled DNA probe representing the gene of interest. Bound radiolabel is visualized by autoradiography. Levels of bound radiolabel can be quantified by scanning the resulting autoradiograph with a densitometer and integrating the area under the traces. Alternatively, incorporated radiolabel can be quantified by phosphorimager analysis of the blot itself.

(b) RT-PCR

In a related embodiment, RNA is isolated from similarly treated cells. The RNA is then subjected to reverse transcription (RT) and amplification by the polymerase chain reaction (PCR) in the presence of radiolabeled deoxynucleotides. The amplification products are resolved by gel electrophoresis and visualized by autoradiography. Levels of incorporated radiolabel can be quantified by scanning the resulting autoradiograph with a densitometer and integrating the area under the traces. Alternatively, incorporated radiolabel can be quantified by phosphorimager analysis of the electrophoretic gel.

(14) Assaying viral replication (a) Viral Titer

In one exemplary embodiment, viral replication is measured by titration of infectious particles on cultured host cells. Virus replication is permitted in host cells, with or without chemical treatment, or with or without co-expression of a regulatory gene, for a measured period of time. The cells are lysed by exposure to a hypotonic solution, and the lysates are subjected to a series of dilutions in isotonic buffer. Several concentrations of cell lysate are separately plated onto cultured host cells. The culture cells are incubated until the cytopathic effects (CPE) are evident. The cultured cells are then fixed and stained with a contrast enhancing dye, such as crystal violet, to facilitate identification of viral plaques. Several culture plates are counted, and the number of plaques multiplied by the appropriate dilution factor, representing the dilution from the original cell lysate. The result reveals the viral titer of the original cell lysate.

(b) In situ PCR

In a related exemplary embodiment, a latent, low copy number virus can be detected with the polymerase chain reaction in situ (Staskus 1994[213]). Cells grown either in suspension culture or on a solid substrate are fixed and permeabilized. PCR reaction components, including synthetic primers complementary to the gene of interest, Taq polymerase, deoxyribonucleotides, are then added to the cells and subjected to thermal cycling typical of PCR. The amplification products, retained in each cell, are detected by in situ hybridization with appropriately labeled DNA probes. An exemplary detection method involves hybridization with radiolabeled probes followed by autoradiography. Similarly, hybridization probes may be nonradioactively labeled by including digoxygenin-11-dUTP into the PCR reaction. Incorporated label is detected either enzymatically or chemically.

(15) Assaying Cell Morphology and Function (a) Light Microscopy

In one exemplary embodiment, the morphology of cells is ascertained by microscopic examination. Living and dead cells are distinguished by treating cells with the stain trypan blue (Schuurhuis 2001[214]). Living cells, with intact cellular membranes, exclude trypan blue while dead cells, with leaky, or perforated outer membranes, permit trypan blue to enter the cytoplasm. Following treatment, examination by phase contrast microscopy reveals the proportion of dead vs. living cells. Similarly, cellular morphology can be ascertained by examination with phase contrast microscopy, with or without prior staining, with, for example, crystal violet, to enhance contrast. Such examination reveals morphologies common to known cell types, and concomitantly reveals irregularities present in the cell population under examination.

(b) Functional Assessment by Immunocytochemistry

In a related exemplary embodiment, the functional status of a given cell population may be determined by treatment with specific antibodies. Cells are dehydrated and fixed with a series of methanol washes using increasing concentrations of methanol. Once fixed, the cells are exposed to cell-type specific antibodies. Examples of suitable antibodies include, but are not limited to, anti-filaggrin for epidermal cells, anti-CD4 for T cells, thymocytes and monocytes, and anti-macrosialin for macrophages. After incubation with differentiation-specific marker antibodies, fluorescently labeled secondary antibodies specific for the first antibody are added. Bound secondary antibodies are visualized by illumination with light of appropriate wavelength to excite the bound fluorochrome followed by microscopic examination. The use of different antibodies, each conjugated to a different fluorochrome, permits the identification of multiple differentiation-specific antigens simultaneously in the same population of cells.

(16) Assaying Cellular Oxidation Stress (a) Cellular Indicators

In one exemplary embodiment, oxidation stress within a population of cells can be measured by assaying the activity levels of certain indicators such as lipid hydroperoxides (Weyers 2001[215]). Cell lysates are prepared and mixed with the substrate 1-napthyldiphenylphosphiine (NDPP). Any resulting oxidized form of the substrate, ONDPP, can be quantified by high performance liquid chromatography (HPLC). ONDPP concentration provides an indirect measure of the oxidation capacity of the cell lysate.

(b) H2DCFDA as Indicator

In another exemplary embodiment, the production of cellular reactive oxygen species can be detected by mixing cell lysates with 2',7'-dichlorodihydrofleuoescein diacetate (H2DCFDA) (Brubacher 2001[216]). In the presence of cellular esterases, H2DCFDA is deacetlyated to produce 2',7'-dichlorodihydrofleuoescein (H2DCF), an oxidant-sensitive indicator. Increased cellular oxidation excites the fluorogenic indicator. Increased sensitivity can be attained by using H2DCF directly, but caution must be exercised by one skilled in the art to ensure that none of the experimental buffers contain contaminants, such as metals, which may lead to spontaneous fluorescence.

d) Optimization Protocols

Once a single constructive or disruptive agent (polynucleotide, polypeptide, small molecule, etc.) is identified in the manner described above, variant agents can be formulated that improve upon the original agent.

The expression "variant agents . . . that improve upon the original agent" is understood to include, but not be limited to, agents that increase therapeutic efficacy, increase prophylactic potential, increase, or decrease stability in vivo or in storage, or increase the number, or variety of post-translational modifications in vivo, including, but not limited to, phosphorylation, acetylation and glycosylation, relative to the original agent.

Variant agents are not limited to those produced in the laboratory. They may include naturally occurring variants. For example, variants with increased stability, due to alterations in ubiquitination or modifications of other target sites conferring resistance to proteolytic degradation.

e) Treatment Protocols (1) Introduction

According to the present invention, a polypeptide has a constructive effect if it attenuates microcompetition with a foreign polynucleotide or attenuates at least one effect of microcompetition with a foreign polynucleotide, or one effect of another foreign polynucleotide-type disruption. For example, a constructive polypeptide can reduce copy number of the foreign polynucleotide, stimulate expression of a GABP regulated gene, increase bioactivity of a GABP regulated protein, through, for instance, GABP phosphorylation and/or increase bioavailability of a GABP regulated protein, through, for instance, a reduction in copy number of microcompeting foreign polynucleotides which bind GABP. A constructive polypeptide can also, for example, inhibit expression of a microcompetition suppressed gene, such as, tissue factor, androgen receptor, and/or inhibit replication of a p300/cbp virus (see more examples below).

Agents of the present invention are designed to address and ameliorate symptoms of chronic diseases, specifically, diseases resulting from microcompetition between a foreign polynucleotide and cellular genes. For instance, introduction of an oligonucleotide agent into a cell may disrupt this microcompetition and restore normal regulation and expression of a microcompeted gene. Agents directed against a foreign polynucleotide may reduce binding or cellular transcription factors to the foreign polynucleotide by, for instance, reducing the copy number of the foreign polynucleotide, or its affinity to the transcription factor, resulting in increased microavailability of the factors towards normal levels. Alternatively, binding of the transcription factors to cellular genes can be stimulated. In yet another exemplary embodiment, insufficient, or excessive expression of a cellular gene in a subject can be modified by administration of nucleic acids or polypeptides to the subject that return the concentration of a cellular polypeptide of interest towards normal levels.

The following section describes standard protocols for determining effective dose, and for agent formulation for use. Additional standard protocols and background information are available in books, such as In vitro Toxicity Testing Protocols (Methods in Molecular Medicine, 43), edited by Sheila O'Hare and C K Atterwill, Humana Press, 1995; Current Protocols in Pharmacology, edited by: S J Enna, Michael Williams, John W Ferkany, Terry Kenakin, Roger D Porsolt, James P Sullivan; Current Protocols in Toxicology, edited by: Mahin Maines (Editor-in-Chief), Lucio G Costa, Donald J Reed, Shigeru Sassa, I Glenn Sipes; Remington: The Science and Practice of Pharmacy, edited by Alfonso R Gennaro, 20$^{th}$ edition, Lippincott, Williams & Wilkins Publishers, 2000; Pharmaceutical Dosage Forms and Drug Delivery Systems, by Howard C Ansel, Loyd V Allen, Nicholas G Popovich, 7$^{th}$ edition, Lippincott Williams & Wilkins Publishers, 1999; Pharmaceutical Calculations, by Mitchell J Stoklosa, Howard C Ansel, 10$^{th}$ edition, Lippincott, Williams & Wilkins Publishers, 1996; Applied Biopharmaceutics and Pharmacokinetics, by Leon Shargel, Andrew B C Yu, 4$^{th}$ edition, McGraw-Hill Professional Publishing, 1999; Oral Drug Absorption: Prediction and Assessment (Drugs and the Pharmaceutical Sciences, Vol 106), edited by Jennifer B Dressman, Hans Lennernas, Marcel Dekker, 2000; Goodman & Gilman's The Pharmacological Basis of Therapeutics, edited by Joel G Hardman, Lee E Limbird, 10$^{th}$ edition, McGraw-Hill Professional Publishing, 2001. See also above referenced.

(2) Effective Dose

Compounds can be administered to a subject, at a therapeutically effective dose, to treat, ameliorate, or prevent a chronic disease. Carefull monitoring of patient status, using either systemic means, standard clinical laboratory assays or assays specifically designed to monitor the bioactivity of a foreign polynucleotide, is necessary to establish the therapeutic dose and monitor its effectiveness.

Prior to patient administration, techniques standard in the art are used with any agent described herein to determine the $LD_{50}$ and $ED_{50}$ (lethal dose which kills one half the treated population, and effective dose in one half the population, respectively) either in cultured cells or laboratory animals. The ratio $LD_{50}/ED_{50}$ represents the therapeutic index which indicates the ratio between toxic and therapeutic effects. Compounds with a relatively large index are preferred. These values are also used to determine the initial therapeutic dose. While unwanted side effects are sometimes unavoidable, they may be minimized by delivery of the therapeutic agent directly to target cells or tissues, thereby avoiding systemic exposure.

Those skilled in the art recognize that animal or cell culture models are imperfect predictors of the efficacy of any treatment in humans. Factors affecting efficacy include route of administration, achievable serum concentration and formulation of the therapeutic agent (i.e. in pill or injectable forms, administered orally or intramuscularly, with accompanying carrier, formulation of an agent adducted with a specific antibody and injected directly into the target tissue, etc.). Regardless of the method of delivery or formulation of the therapeutic agent, it is important to monitor plasma levels using a suitable technique, such as atomic absorption spectroscopy, enzyme linked immunosorbant assay (ELISA), or high performance liquid chromatography (HPLC) among others.

(3) Formulation for Use

Those skilled in the art recognize a host of standard formulations for the agents described in this invention. Any suitable formulation may be prepared for delivery of the agent by injection, inhalation, transdermal diffusion or insufflation. In every case, the formulation must be appropriate for the means and route of administration.

Oligonucleotide agents, e.g. antisense oligonucleotides or recombinant expression vectors, may be formulated for localized or systemic administration. Systemic administration may be achieved by injection in a physiologically isotonic buffer including Ringer's or Hank's solution, among others. Alternatively, the agent may be given orally by delivery in a tablet, capsule or liquid syrup. Those skilled in the art recognize pharmaceutical binding agents and carriers which protect the agent from degradation in the digestive system and facilitate uptake. Similarly, coatings for the tablet or capsule may be used to ease ingestion thereby encouraging patient compliance. If delivered in liquid suspension, additives may be included which keep the agent suspended, such as sorbitol syrup and the emulsifying agent lecithin, among others, lipophilic additives may be included, such as oily esters, or preservatives may be used to increase shelf life of the agent. Patient compliance may be further enhanced by the addition of flavors, coloring agents or sweeteners. In a related embodiment the agent may be provided in lyophilized form for reconstitution by the patient or his or her caregiver.

The agents described herein may also be delivered via buccal absorption in lozenge form or by inhalation via nasal aerosol. In the latter mode of administration any of several propellants, including, but not limited to, trichlorofluoromethane and carbon dioxide, or delivery methods, including but not limited to a nebulser, can be employed. Similarly, compounds may be included in the formulation which facilitate transepithelial uptake of the agent. These include, among others, bile salts and detergents. Alternatively, the agents of this invention may be formulated for delivery by rectal suppository or retention enema. Those skilled in the art recognize suitable methods for delivery of controlled doses.

In related embodiments, the agents may be formulated for depot administration, such as by implantation, via regulated pumps, either implanted or worn extracorporally or by intramuscular injection. In these instances the agent may be formulated with hydrophobic materials, such as an emulsification in a pharmaceutically permissible oil, bound to ion exchange resins or as a sparingly soluble salt.

In every case, therapeutic agents destined for administration outside of a clinical setting may be packaged in any suitable way that assures patient compliance with regard to dose and frequency of admimistration.

Administration of the agents included in this invention in a clinical situation may be achieved by a number of means including injection. This method of systemic administration may achieve cell-type specific targeting by using a nucleic acid agent, described herein, modified by addition of a polypeptide which binds to receptors on the target cell. Additional specificity may be derived from the use of recombinant expression vectors which carry cell- or tissue-type specific promoters or other regulatory elements. In contrast to systemic injection more specific delivery may be achieved by means of a catheter, by stereotactic injection, by electorporation or by transdermal electrophoresis. Many suitable delivery techniques are well known in the art.

In an alternative embodiment the therapeutic agent may be administered by infection with a recombinant virus carrying the agent. Similarly cells may be engineered ex vivo which express the agent. Those cells may themselves become the pharmaceutical agent for implantation into the site of interest in the patient.

f) Diagnosis Protocols

Diagnosis may be achieved by a number of methods, well known in the art, using as reagents sequences of a foreign polynucleotide, disrupted gene or polypeptide, or a gene or polypeptide in a disruptive or disrupted pathway, or antibodies directed against such polynucleotides or polypeptides. Those reagents may be used to detect and quantify the copy number, level of expression or persistence of expression products of a foreign polynucleotide, disrupted gene or gene susceptible to microcompetition with a foreign polynucleotide.

Diagnostic methods may employ any suitable technique well known in the art. These include, but are not limited to, commercially available diagnostic kits which are specific for one or more foreign polynucleotides, a specific disrupted gene, a disrupted polypeptide, a gene or polypeptide in a disruptive or disrupted pathway, or an antibody against such polynucleotides or polypeptides. Well known advantages of commercial kits include convenience and reproducibility due to manufacturing standardization, quality control and validation procedures.

(1) Detection and Quantification of Polynucleotides

In one exemplary embodiment, nucleic acids, DNA or RNA, are isolated from a cell or tissue of interest using procedures well known in the art. Once isolated, the presence of a foreign polynucleotide may be ascertained by any of a number of procedures including, but not limited to, Southern blot hybridization, dot blotting and the PCR, among others. Mutations in those polynucleotides may be detected by single strand conformation analysis, allele specific oligonucleotide hybridization and related and complementary techniques. Alternatively nucleic acid hybridization with appropriately labeled probes may be performed in situ on isolated cells or tissues removed from the patient. Suitable techniques are described, for example, Sambrook 2001 (ibid), incorporated herein in its entirety by reference. Control cells and tissues are compared in parallel to validate any positive findings in clinical samples.

If the nucleic acid molecules specific to foreign polynucleotides or disrupted genes, or genes in disrupted or disruptive pathways are in low concentration, preferred diagnostic methods employ some means of amplification. Examples of suitable procedures include the PCR, ligase chain reaction, or any of a number of other suitable methods well known in the art.

In one exemplary embodiment of a diagnostic technique employing nucleic acid hybridization, RNA from the cell of interest is isolated and converted to cDNA (using the enzyme reverse transcriptase of avian or murine origin). Once cDNA is prepared, it is amplified by the PCR, or a similar method, using a sequence specific oligonucleotide primer of 20-30 nucleotides in length. Incorporation of radiolabeled nucleotides during amplification facilitates detection following electrophoresis through native polyacrylamide gels by autoradiography or phosphorimager analysis. If sufficient amplification products are attained, they may be visualized by staining of the electrophoretic gel by ethidium bromide or a similar compound well known in the art.

(2) Detection and Quantification of Polypeptides

Antibodies directed against foreign polypeptides, disrupted polypeptides, or polypeptides in disrupted or disruptive pathways, may also be used for the diagnosis of chronic disease. Diagnostic protocols may be employed to detect variations in the expression levels of polypeptides or RNA transcripts. Similarly, they may be used to detect structural variation including nucleic acid mutations and changes in the sequence of encoded polypeptides. The latter may be detected by changes in electrophoretic mobility, indicative of altered charge, or by changes in immunoreactivity, indicative of alterations in antigenic determinants.

For diagnositic purposes, protein may be isolated from the cells or tissues of interest using any of many techniques well known in the art. Exemplary protocols are described in Molecular Cloning: A Laboratory Manual, 3rd Ed (Third Edition) By Joe Sambrook, Peter MacCallum and David Russell (Cold Spring Harbor Laboratory Press 2001), incorporated herein by reference in its entirety.

In a preferred embodiment, detection of a foreign polypeptide molecule, or a cellular disrupted polypeptide molecule, or a polypeptide in a disruptive or disrupted pathway is achieved with immunological methods, including immunoaffinity chromatography, radial immunoassays, radioimmunoassay, enzyme linked immunsorbant assay, etc. These techniques, quantitative and qualitative, all well known in the art, exploit the interaction between specific antibodies and antigenic determinants on the target molecule. In each assay, polyclonal or monoclonal antibodies, or fragments thereof, may be used as appropriate.

Immunological assays may be employed to analyze histological preparations. In a preferred embodiment, tissue or cells of interest are treated with a fluorescently labeled specific antibody or an unlabeled antibody followed by reaction with a secondary fluorescently labeled antibody. Following incubation for sufficient time and under appropriate conditions for antibody-antigen interaction, the label may be visualized microscopically, in the case of either tissues or cells, or by flow cytometry, in the case of individual cells. These techniques are particularly suitable for antigens expressed on the cell surface. If they are not on the cell surface, the cells or tissue to be analyzed must be treated to become permeable to the diagnostic antibodies. In addition to the detection of antigens on the material studied, the distribution of that antibody will become evident upon microscopic examination. All immunological assays involve the incubation of a biological sample, cells or tissue, with an appropriately specific antibody or antibodies. These and other suitable diagnostic methods are familiar to those skilled in the art.

In an alternative embodiment, immunological techniques may be employed which involve either immobilized antibodies or immobilizing the cells to be analyzed on, for example, synthetic beads or the surface of a plastic dish, typically a microtiter plate (see above).

Immobilization of antibodies or cells to be analyzed is achieved through the use of any of several substrates well known in the art including, but not limited to, glass, dextran, nylon, cellulose, and polypropylene, among others. The actual shape or configuration of the substrate may vary to suite the desired assay. For example, polystyrene may be formed into tissue culture or microtitre plates, dextran may be formed into beads suitable for column chromatography, or polyacrylamide may be coated onto the inner surface of a glass test tube or bottle. These and related carriers and configurations are well known and can be tested for utility by those skilled in the art.

Detection of bound antibodies is achieved by labeling, either directly or indirectly, through the use of a secondary antibody specific for the first. The label may be either a chromophore which responds to excitation by a specific wavelength of light, thereby producing fluorescence or it may be an enzyme which reacts with a chromogenic substrate to produce detectable reaction products. Common florescent labels include fluorescineisothiocyanate (FITC), rhodamine and trans-1-bromo-2,5-bis-(3-hydroxycarbonyl-4-hydroxy)styrylbenzene (BSB), among others. Enzymes commonly conjugated with antibodies include, but are not limited to, alkaline phosphatase, horse radish peroxidase and β-galactosidase. Other alternatives are available and well known in the art.

In a related embodiment, the antibody is labeled with a fluorescent metal, for example $^{152}$Eu, which can be attached directly to the primary or secondary antibody in an immunoassay. Alternatively, the antibody may be labeled with a chemiluminescent compound, such as luminol, isoluminol or imidazole or a bioluminiscent compount, such as luciferin or aequorin. Subsequent reaction with the appropriate substrate for the labeling compound produces light which is detectable visually or by fluorimetry.

(3) Imaging of Diseased Tissues

Under suitable circumstances, foreign polypeptides, polypeptides expressed from disrupted genes, or from genes in a disruptive or disrupted pathway, may be detected on the surface of affected cells or tissues. In these instances the level and pattern of expression may be visualized and used to both diagnose disease and to guide and gauge therapy. For example, in atherosclerosis, such disrupted polypeptides may include, but are not limited to CD18 or tissue factor (see more details in examples below).

Under these circumstances, antibodies, monoclonal or polyclonal, which specifically interact with proteins expressed on the cell surface may be used for the diagnosis of chronic disease and for monitoring treatment efficacy. In this embodiment, an appropriate antibody or antibody fragment is labeled with a radioactive, fluorescent, or other suitable tag prior to reaction with the biomaterial to be assayed. Conditions for reaction and visualization are well known in the art and permit analyses to be carried out in vitro as well as in situ. In a preferred embodiment, antibody fragments are used for in situ or in vitro assays because their smaller size leads to more rapid accumulation in the tissue of interest and more rapid clearing from that tissue following the assay. A number of suitable and appropriate labels may be used for the assays in this invention that are well known in the art.

g) Clinical Trials

Another aspect of current invention involves monitoring the effect of a compound on a treated subject in a clinical trial. In such a trial, the copy number of a foreign polynucleotide, its affinity to cellular transcription factors, the expression or bioactivity of a disrupted gene or polypeptide, or expression or bioactivity of a gene or polypeptide in a disrupted or disruptive pathway, may be used as an indicator of the compound effect on a disease state.

For example, to study the effect of a test compound in a clinical trial, blood may be collected from a subject before, and at different times following treatment with such a compound. The copy number of a foreign polynucleotide may be assayed in monocytes as described above, or the levels of expression of a disrupted gene, such as tissue factor, may be assayed by, for instance, Northern blot analysis, or RT-PCR, as described in this application, or by measuring the concentration of the protein by one of the methods described above. In this way, the copy number, or expression profile of a gene of interest or its mRNA, may serve a surrogate or direct biomarker of treatment efficacy. Accordingly, the response may be determined prior to, and at various times following compound administration. The effects of any therapeutic agent of this invention may be similarly studied if, prior to the study, a suitable surrogate or direct biomarker of efficacy, which is readily assayable, was identified.

B. EXAMPLES

The current view holds that, in vivo, viral proteins are the sole mediators of viral effects on the host cell. Such proteins include, for example, the papilomavirus type 16 E6 and E7 oncoproteins, SV40 large T antigen, Epstein-Barr virus BRLF1 protein, and adenovirus E1A. The possibility that presence of viral DNA in the host cell can directly impact cell function, independent of viral protein, is typically ignored. The viral "protein-dependent" view is so ingrained in current research that in many cases, when a "protein-independent" effect on cellular gene expression, or other cell functions, presents itself in the laboratory, the effect is ignored. As a result, the significance of such effect, and specifically, its relation to disease is overlooked. Note that the effect of viral DNA on the cellular genome in cases of viral DNA integration which may result in mutations, deletions or methylation of host cell DNA, cannot be considered "protein-independent" since it is mediated by viral proteins, such as, HIV-1 IN protein, or retrovirus integrase. The following examples illustrate the invention. More examples can be found in patent application PCT/US01/05314, incorporated herein in its entirety by reference.

1. Foreign Polynucleotides and Aberrant Transcription a) Introduction

Microcompetition between a foreign polynucleotide and a cellular gene for a limiting cellular transcription complex result in aberrant transcription of the cellular gene. If the limiting complex stimulates the gene transcription, microcompetition with the foreign polynucleotide reduces transcription. If the limiting complex suppresses the gene transcription, microcompetition with the the foreign polynucleotide increases transcription. Aberrant transcription can result in abberant gene expression, abnormal gene product activity, and irregular cell function. Consider the following observations.

b) Examples

(1) Scholer 1984

The plasmid pSV2CAT expresses the chloramphenicol acethyltransferase (CAT) gene under the control of the SV40 promoter/enhancer. A study (Scholer 1984[217]) first transfected an increasing amount of pSV2CAT in CV-1 cells. CAT activity reached a plateau at 0.3 pmol pSV2CAT DNA per dish. Based on this observation, the study concluded that CV-1 cell contain a limited concentration of cellular factor needed for pSV2CAT transcription. Next, the study cotransfected a constant concentration of pSV2CAT with increasing concentrations of pSV2neo, a plasmid identical to pSV2CAT, except the reporter gene is neomycin-phosphotransferase (neo). The addition of pSV2neo resulted in a linear decrease of the CAT signal (Scholer 1984, ibid, FIG. 2B). Next, the study cotransfected pSV2CAT with a plasmid that included all SV40 early control elements except for the 72-bp enhancer. No competition was observed. A point mutation in the 72-bp enhancer, which abolished the enhancer functional activity, also eliminated competition. Based on these observations, Scholer, et al., (1984, ibid) concluded that "taken together, our data indicate that a limited amount of the cellular factors required for the function of the SV40 72-bp repeats is present in CV-1 cells. Increasing the number of functional SV40 enhancer elements successfully competes for these factors, whereas other elements necessary for stable transcription did not show such an effect." The study also observed competition between pSV2CAT and pSrM2Δ, a plasmid which harbors the Moloney murine sarcoma virus (MSV) enhancer (Scholer 1984, ibid, FIG. 5A and B). Note, that except the enhancers, the transcriptional control elements in pSV2CAT and pSrM2Δ are same. Based on these observations, Scholer, et al., (1984, ibid) concluded that "one class of (a limiting) cellular factor(s) is required for the activity of different enhancers. Furthermore, BK (BK virus) and RSV (Rous sarcoma virus) enhancers also interact with the same class of molecule(s)."

(2) Mercola 1985

The plasmid pSV2CAT expresses the chloramphenicol acethyltransferase (CAT) gene under the control of the SV40 promoter/enhancer. The pX1.0 plasmid contains the murine immunoglobulin heavy-chain (Ig H) enhancer. The pSV2neo expresses the neo gene under the control of the SV40 promoter/enhancer. The pA10neo and pSV2neo are identical except that pA10neo lacks most of the SV40 enhancer.

Figure 4:
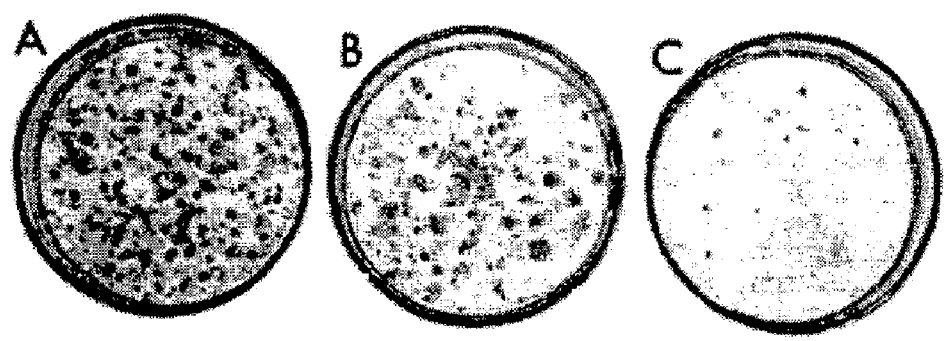
FIG. 4 shows accumulation of triglyceride assayed by oil red staining in untreated F442A cells or in cells transfected with either a vector expressing the SV40 large T antigen or the "empty vector" pZIPNeo.

A study (Mercola 1985[218]) cotransfected a constant amount of pSV2CAT into murine plasmacytoma P3×63-Ag8 cells, as test plasmid, with increasing amounts of pX1.0 as competitor plasmid. A plasmid lacking both reporter gene and enhancer sequences was added to produce equimolar amounts of plasmid DNA in the transfected cells. FIG. 1 illustrates the observed relative CAT activity as a function of the relative concentration of the competitor plasmid (Mercola 1985, ibid, FIG. 4A).

An increase in concentration of the contransfected murine immunoglobulin heavy-chain (H) enhancer decreased expression from the plasmid carrying the SV40 viral enhancer. Microcompetition between viral and cellular heavy-chain enhancers decreased expression of the gene under control of the viral enhancer. Based on these observations, Mercola, et al., (1985, ibid) concluded that in the plasmacytoma cells the heavy chain enhancer competes for a trans-acting factor required for the SV40 enhancer function.

Figure 2:
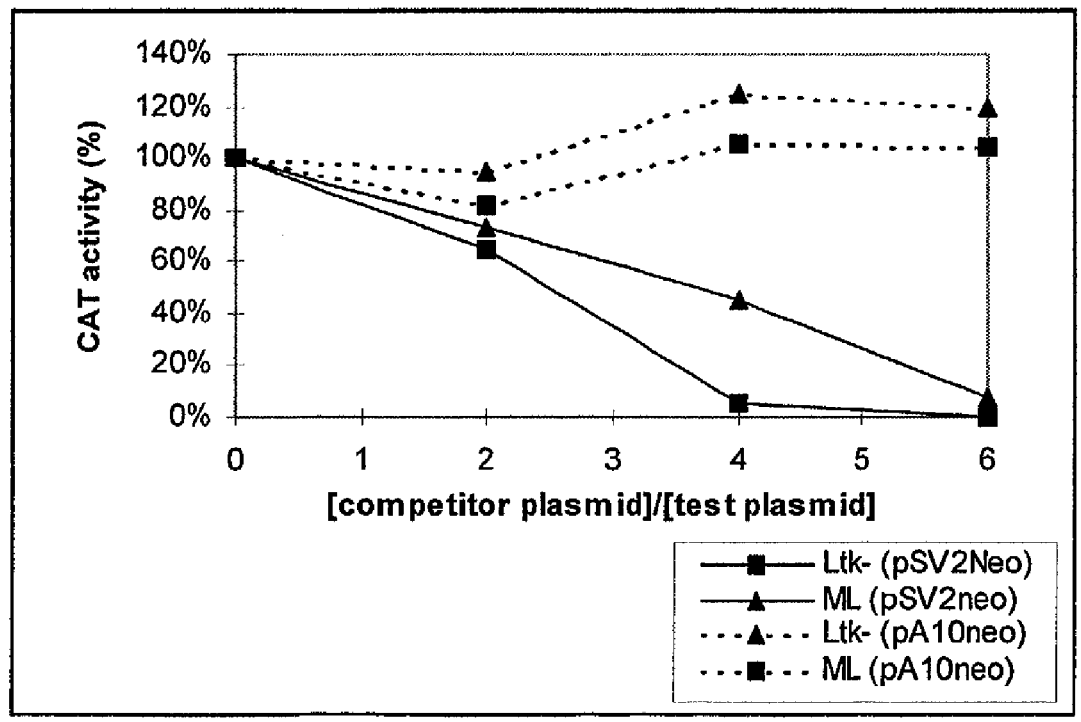
FIG. 2 shows the observed relative CAT activity as a function of the relative concentration of the competitor plasmid pSV2neo to the test plasmid pSV2CAT, and the relative concentration of the competitor plasmid pA10neo to the test plasmid pSV2CAT, in either Ltk- or ML fibroblast cells.

In another experiment, the study cotransfected a constant amount of pSV2CAT, as test plasmid, with increasing amount of pSV2neo, as competitior plasmid, in either Ltk- or ML fibroblast cells. To isolate the effect of the viral enhancer, the study also cotransfected a constant amount of the test plasmid pSV2CAT with increasing amount of the enhancerless pA10neo plasmid. FIG. 2 illustrates the observed relative CAT activity as a function of the relative concentration of the competitor plasmid (Mercola 1985, ibid, FIG. 4B).

An increase in concentration of the contransfected SV40 viral enhancer decreased expression from the plasmid also carrying the SV40 enhancer. An increase in concentration of a plasmid lacking the enhancer did not affect the test plasmid reporter gene activity.

Overall, the study concluded that "in vivo competition experiments revealed the presence of a limited concentration of molecules that bind to the heavy-chain enhancer and are required for its activity. In the plasmacytoma cell, transcription dependent on the SV40 enhancer was also prevented with the heavy-chain enhancer as competitor, indicating that at least one common factor is utilized by the heavy-chain and SV40 enhancers."

(3) Scholer 1986

Figure 3:
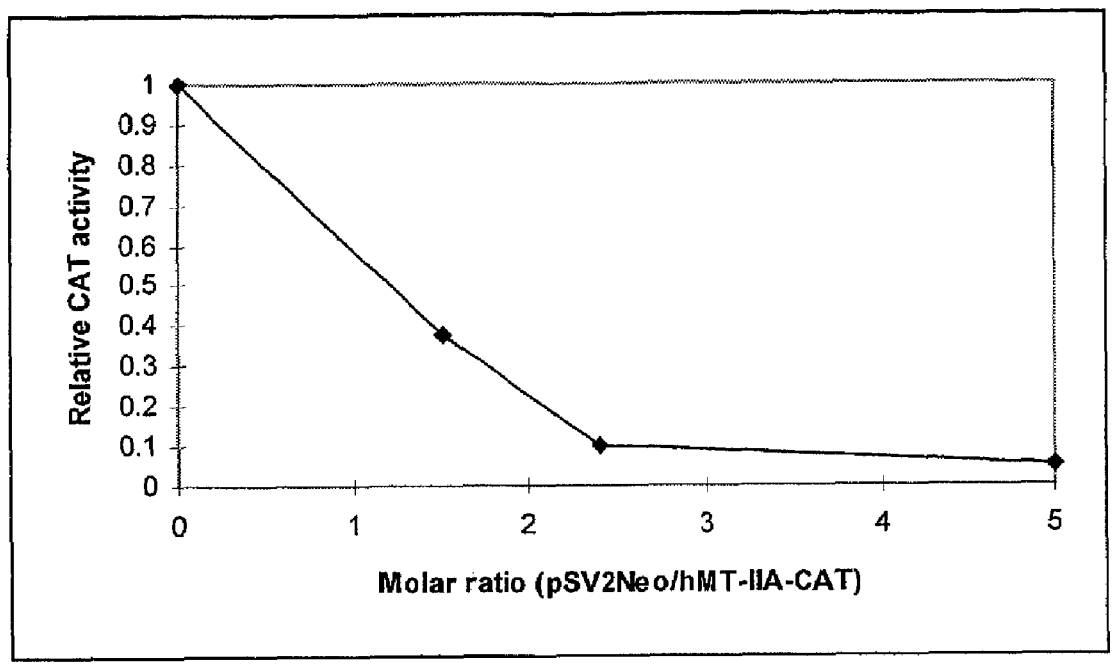
FIG. 3 shows the observed relative CAT activity, expressed as the ratio between CAT activity in the presence of pSV2neo and CAT activity in the absence of pSV2neo, as a function of the molar ratio of pSV2Neo to hMT-IIA-CAT.

Another study (Scholer 1986[219]) cotransfected CV-1 monkey kidney cells with a constant amount of a plasmid containing the hMT-II$_A$ promoter (−286 nt relative to the start of transcription to +75 nt) fused to the bacterial gene encoding chloramphenicol acetyltransferase (hMT-IIA-CAT) along with increasing concentrations of a plasmid containing the viral SV40 early promoter and enhancer fused to the bacterial gene conferring neomycin resistance (pSV2neo). FIG. 3 presents the observed relative CAT activity (expressed as the ratio between CAT activity in the presence of pSV2neo and CAT activity in the absence of pSV2neo) as a function of the molar ratio of pSV2Neo to hMT-IIA-CAT.

The figure illustrates the effect of competition between the two plasmids on the relative CAT activity. A 2.4-fold molar excess of the plasmid containing the viral enhancer reduced CAT activity by 90%. No competition was observed with the viral plasmid after deletion of the SV40 enhancer suggesting that elements in the viral enhancer are responsible for the observed reduction in reporter gene expression.

(4) Cherington 1988 pZIP-neo expresses the neomycin-resistant gene under control of the Moloney murine leukemia virus long terminal repeat (LTR) (Cepko 1984[220]).

Another study inserted the wild-type early region of SV40 into the "empty" pZIP-Neo plasmid and labled the new plasmid, which expressed the SV40 large T antigen, "wild-type" (WT). The study transfected 3T3-F442A preadipocytes with either WT or pZIPneo. Accumulation of triglyceride, assayed by oil red staining, was used as marker of differentiation. Seven days postconfluence, the number of staining of cells was recorded. Consider the following figure (Cherington 1988[221], FIG. 4A, B and C). Darker staining indicates increased differentiation. (A) marks untreated F442A cells, (B) marks cells transfected with pZIP-neo, (C) marks cells transfected with WT. Consider FIG. 4.

Transfection with WT, the vector expressing the SV40 large T antigen, reduced differentiation. Compare triglyceride staining in (C) and (A). Transfection with the "empty" vector, although less so than transfection with the WT vector, also reduced differentiation. Compare triglyceride staining in (B) relative to (A) and (C). The results demotstrate the effect of microcomopetition on cell differentiation.

(5) Adam 1996

Figure 5:
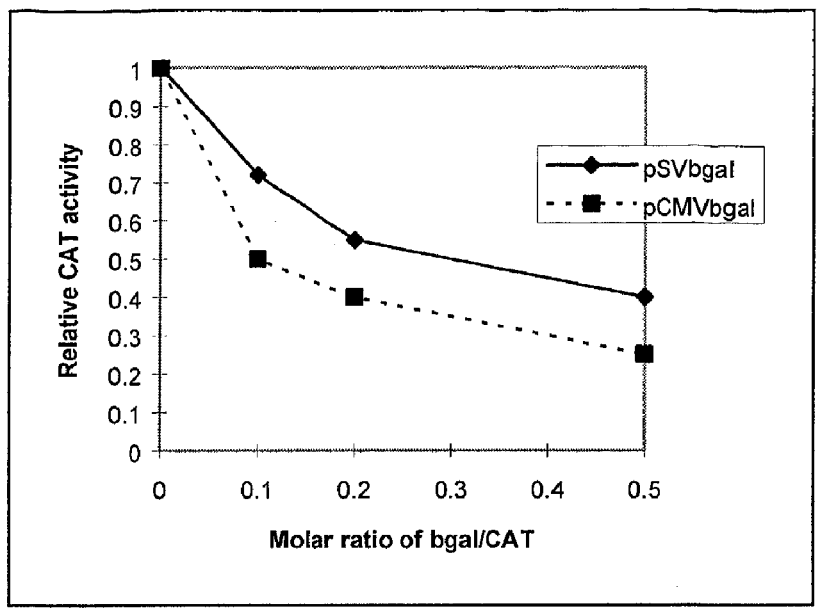
FIG. 5 shows the observed relative CAT activity as a function of the molar ratio between the competitor plasmid CMV-βgal and the test plasmid PDGF-B-CAT, or between the competitor plasmid SV40-βgal and the test plasmid PDGF-B-CAT.

Another study (Adam 1996[222]) cotransfected JEG-3 human choriocarcinoma cells with a constant concentration of a plasmid carrying CAT reporter gene under the control of the platelet derived growth factor-B (PDGF-B) promoter/enhancer (PDGF-B-CAT), and increasing concentrations of a second plasmid containing either the human cytomegalovirus promoter/enhancer fused to β-galactosidase (CMV-βgal), or the SV40 early promoter and enhancer elements fused to βgal (SV40-βgal). FIG. 5 present the observed relative CAT activity as a function of the molar ratio between the plasmids carrying βgal and CAT (based on Adam 1996, ibid, FIG. 1).

The results demonstrate the negative, concentration-dependent effect of microcompetition between the CMV promoter/enhancer, or SV40 promoter/enhancer, and the PDGF-B promoter.

(6) Higgins 1996

HSV-neo is a plasmid that expresses the neomycin-resistance gene under control of the murine Harvey sarcoma virus long terminal repeat (LTR) (Armelin 1984[223]). pZIP-neo expresses the neomycin-resistant gene under control of the Moloney murine leukemia virus long terminal repeat (LTR) (Cepko 1984, ibid).

A study (Higgins 1996[224]) transfected murine 3T3-L1 preadipocytes with PVU0, a vector carrying an intact early region of the SV40 genome expressing the SV40 large tumor antigen and the SV40 small tumor antigen. The cells were also transfected with HSV-neo and pZIP-neo as "empty" controls. Following transfection, the study cultured the cells under differentiation inducing conditions, and measured glycerophosphate dehydrogenase (GPD) activity as marker of differentiation. The results are presented in the following table (Higgins 1996[225], Table 1, first four lines).

| Vector | Cell line | GPD activity (U/mg of protein) |
| --- | --- | --- |
| None | L1 | 2,063 1,599 |
| HSV-neo | L1-HNeo | 1,519 1,133 |
| ZIP-neo | L1-ZNeo | 1,155 1,123 |
| PVU0 | L1-PVU0 | 47, 25 |

Transfection of PVU0 and expression of the large and small T antigens resulted in a statistically significant decrease in GPD activity. Transfection of the "empty" vectors, HSV-neo and ZIP-neo, although less effective than PVU0, also reduced GPD activity. In a t-test, assuming unequal variances, the p-value for the difference between the HSV-neo vector and no vector is 0.118, and the p-value for the difference between ZIP-neo and no vector is 0.103. Given that the sample includes only two observations, a p-value around 10% for vectors carrying two different LTRs indicates a trend. The observations demonstrate the effect of microcompetition with HSV-neo and Zip-Neo, the "empty vectors," on cell differentiation.

(7) Gordeladze 1997

The effect of microcompetition on hormone senstivie lipase (HSL) transcription can be demonstrated by combining observations from two studies. Swiss mouse embryo 3T3-L1 fibroblasts can be induced to differentiate into adipocyte-like cells. Undifferentiated cells contain very low level of HSL activity, while differentiated adipocyte-like cells show much higher activity (a 19-fold increase relative to undifferentiated cells) (Kawamura 1981[226]). 3T3-L1 preadipocytes were induced to differentiate by incubation with insulin (10 μg/ml), dexamethasone (10 nM), or iBuMeXan (0.5 mM) for 8 consecutive days following cell confluency. HSL mRNA was measured in undifferentiated confluent controls and differentiated 3T3-L1 cells transfected with the pZipNeo vector. Although differentiated 3T3-L1 cells usually show significant HSL activity, the 3T3-L1 differentiated cells transfected with pZipNeo showed decreased HSL mRNA (Gordeladze 1997[227], FIG. 11. Compare pZipNeo and Wtype columns in FIG. 6).

pZipNeo carries the Moloney murine leukemia virus LTR which microcompeted with HSL promoter. The results demostrate the effect of microcompetition with the viral LTR on HSL transcription.

(8) Awazu 1998

Figure 7:
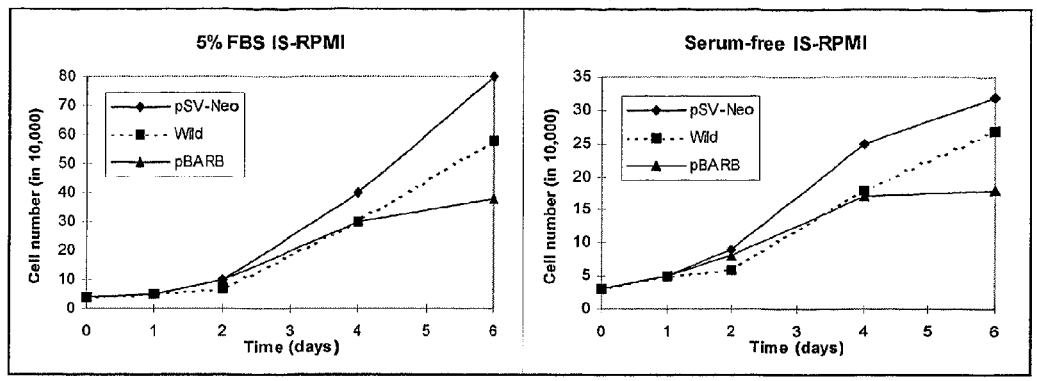
FIG. 7 shows the observed number of viable cells following transfection with either the pBARB vector or the "empty vector" pSV-neo.

A study (Awazu 1998[228]) transfected HuH-7 human hepatoma cells with pBARB, a plasmid in which the β-actin promoter regulates the expression of the Rb gene, and the simian virus (SV40) promoter regulates the expression of the neomycin-resistance (neo) gene. The study also transfected the cells with the pSV40-neo plasmid, which only includes the SV40 promoter and neo gene. Since pSV40-neo does not include the α-actin promoter and Rb gene, the study considered the pSV40-neo plasmid as "empty" and used it as control. The cell were incubated in IS-RPMI, with or without 5% FBS, and the number of viable cells were counted at the indicated times. FIG. 7 summarizes the results (Awazu 1998, ibid, FIG. 2A). The SD is about the size of the triangular symbols.

The result demonstrate the effect of microcompetition with pSV40-neo, the "empty vector" on cell proliferation.

(9) Hofman 2000

The pSG5 plasmid includes the early SV40 promoter to facilitate in vivo expression, and the T7 bacteriophage promoter to facilitate in vitro transcription of cloned inserts. Both the pcDNA1.1 and pIRESneo plasmids includes the human cytomegalovirus (CMV) immediate early (IE) promoter and enhancer.

Another study (Hofman 2000[229]) constructed a series of pSG5 based vectors by cloning certain sequences into the EcoRI restriction site ("insert plasmid," see list in table below). The inserts varied in length measured in base pair (bp). The study cotransfected each insert plasmid (650 ng) with pSG5-luc (20 ng), as test plasmid, in COS-7 cells. The test plasmid pSG5-luc was also cotransfected with the pGEM-7Zf(+) plasmid, or with herring sperm DNA. Luciferase (luc) activities were measured. Luc activity in presence of the empty pSG5 vector was arbitrarily set to 1. The following table presents the observed relative luc activity in every experiment (Hofman 2000, ibid, FIG. 3a).

| Plasmid | Size of insert (bp) | Luc activity from pSG5-luc (fold increase) |
|---|---|---|
| pGEM7zf+ | | 72 |
| herring | | 71 |
| pSG5-NuRIP183 | 4,776 | 47 |
| pSG5-TIF2 | 4,395 | 40 |
| pSG5-NuRIP183D1 | 4,326 | 36 |
| pSG5-NuRIP183D2 | 3,723 | 33 |
| pSG5-NuRIP183D3 | 3,219 | 30 |
| pSG5-NuRIP183D4 | 2,684 | 28 |
| pSG5-NuRIP183D5 | 2,400 | 25 |
| pSG5-NuRIP183D6 | 1,889 | 22 |
| pSG5-ARA70 | 1,800 | 20 |
| pSG5-TIF2.5 | 738 | 7 |
| pSG5-DBI | 259 | 3 |
| pSG5 | 0 | 1 |

Based on these observations Hofman, et al., (2000, ibid) concluded that "Remarkably, the measured luciferase activity tended to be inversely related to the length of the insert in the cotransfected pSG5-constructs." Moreover, "We can conclude from these data that the SV40 promoter driven expression of nuclear receptor or of luciferase in COS-7 cells is inhibited to various degrees by cotransfection, with maximal inhibition in the presence of the empty expression vector and minimal inhibition in the presence of pSG5 constructs containing large inserts." First note that the pGEM-7Zf(+) plasmid and the herring sperm DNA do not include a human viral promoter or enhancer. The promoters in pGEM-7Zf(+) is the bacteriophage SP6 and bacteriophage T7 RNA polymerase promoters (a bacteriophage is a virus that infects bacteria). Second note that a decrease in the size of the insert, increases the copy number of the insert plasmid resulting in accentuated microcompetition with the test plasmid.

Figure 8:
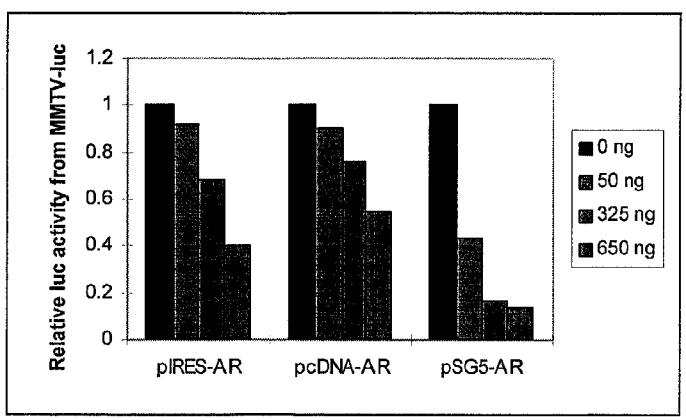
FIG. 8 shows the observed luc activity following transfection with 20 ng pIRES-AR, pcDNA-AR or pSG5-AR plasmids which express AR, 500 ng MMTV-luc which highly expresses luc following AR stimulation of the MMTV promoter, and increasing amounts of the empty expression vector, where luc activity in the presence of 650 ng pGEM-7Zf(+) was arbitrarily set to 1.

The study also measured the effect of cotransfection on the activity of the androgen receptor (AR). The study transfected COS-7 cells with 20 ng pIRES-AR, pcDNA-AR or pSG5-AR plasmids which express AR, 500 ng MMTV-luc which highly expresses luc following AR stimulation of the MMTV promoter, and increasing amounts of the empty expression vector. The pGEM-7Zf(+) plasmid was used instead of the expression plasmid to maintain a 650 ng final concentration of cotransfected DNA. Transfected cells were treated with 10 nM R1881, an AR ligand, and luciferase activity was measured. The luc activity in the presence of 650 ng pGEM-7Zf(+) was arbitrarily set to 1, and the relative luc activity was calculated. FIG. 8 presents the results (Hofman 2000, ibid, FIG. 5a).

According to Hofman, et al., (2000, ibid) "The MMTV-luciferase response was strongly reduced in the presence of increasing concentrations of the empty expression vector and the reduced receptor activities were proportional to AR expression levels." The decrease in MMTV-luc transcription resulted from decreased transcription of the AR gene expressed by the pIRES-AR, pcDNA-AR, and pSG5-AR plasmids (see also Hofman 2000, ibid, FIG. 5b). Transfection with the calcium phosphate precipitation method, instead of FuGENE-6™, produced similar results.

Figure 9:
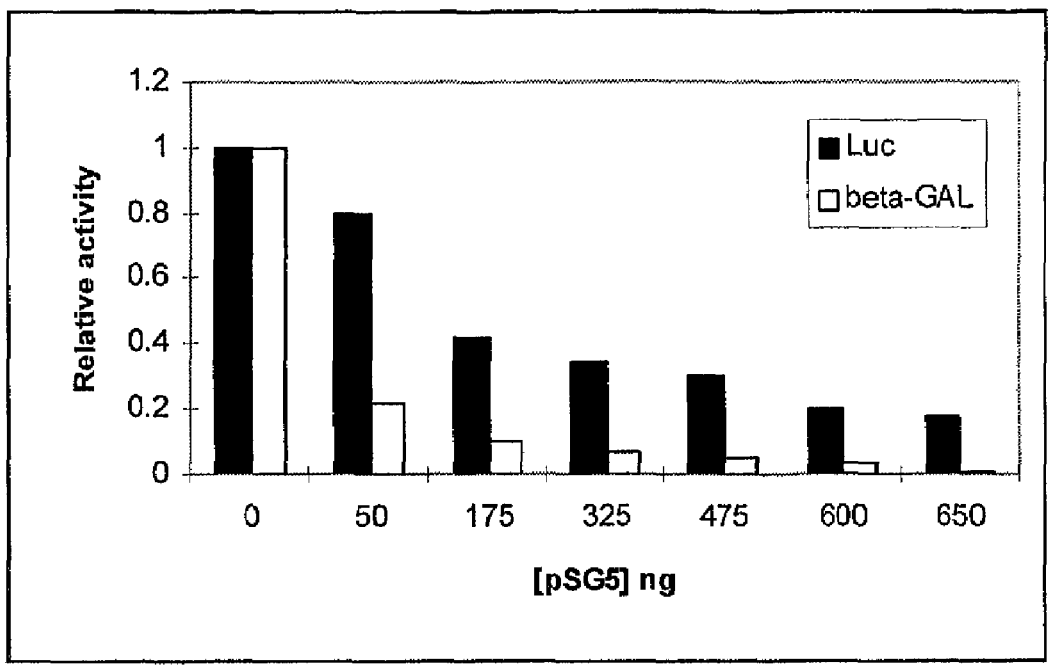
FIG. 9 shows the observed luc activity following transfection with 20 ng pSG5-AR, 20 ng pS40-β-galactosidase (βGAL) and increasing amounts of the empty vector pSG5, where luc and βGAL activities in the presence of 650 pGEM-7Zf(+) were arbitrarily set to 1.

Finally, the study transiently cotransfected COS-7 cells with 20 ng pSG5-AR, 20 ng pS40-β-galactosidase (βGAL) and increasing amounts of the empty pSG5 vector. pGEM-7Zf(+) was used to maintain the DNA concentration at a constant level. Luc and βGAL activities in the presence of 650 pGEM-7Zf(+) were arbitrarily set to 1, and the relative luc activity was calculated. FIG. 9 present the results (Hofman 2000, ibid, FIG. 7a).

Based on these observations, Hofman, et al., (2000, ibid) concluded that "The most likely explanation is that the total amount of transfected expression vectors largely exceeds the capacity of the transcriptional machinery of the cell. For that reason, competition occurs between the receptor construct and the cotransfected construct."

(10) Choi 2001

Figure 10:
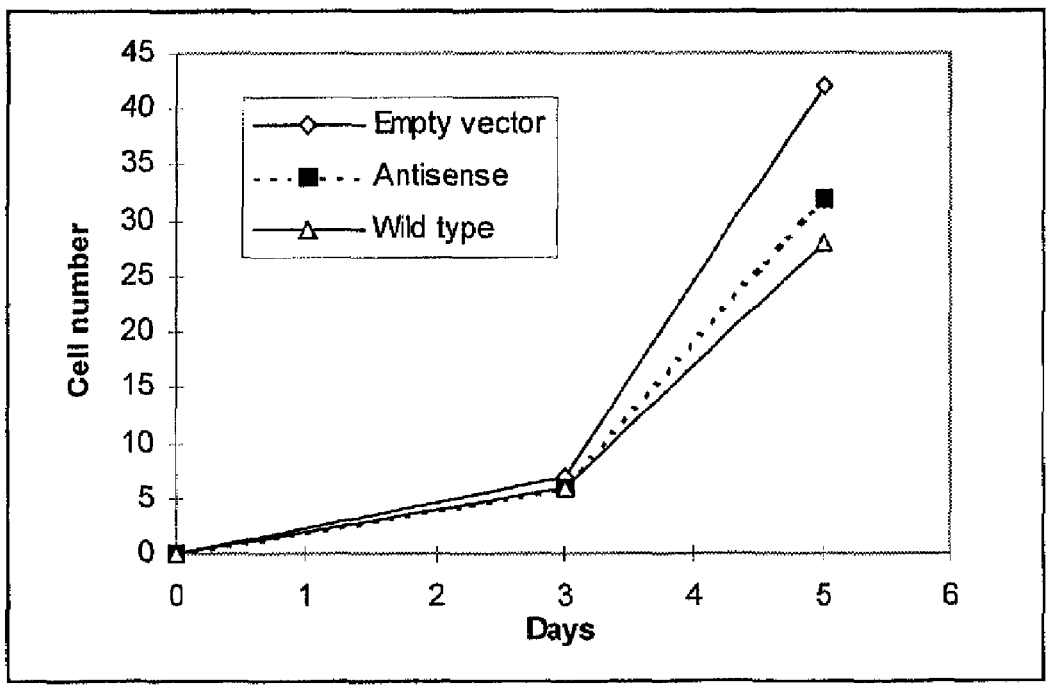
FIG. 10 shows the observed number of cells over time following transfection with either the pcDNA3 vector carrying an antisense to the macrophage inflammatory protein 1-α (MIP-1α) or with the "empty" pcDNA3 vector.

Another study (Choi 2001[230]) stably transfected the human MM-derived cell line ARH with the pcDNA3 vector carrying an antisense to the macrophage inflammatory protein 1-α (MIP-1α) (AS-ARH). As control, the study transfected other ARH cells with the "empty" pcDNA3 vector (EV-ARH). To measure the effect of the antisense on cell growth, the study cultured $10^5$ non-transfected (wild type), empty vector, and MIP-1a antisenese (antisense) transfected ARH cells in six-well plates with RPMI-1640 media containing 10% FBS. At days 3 and 5, the cells were sampled, stained and counted. FIG. 10 present the results (Choi 2001, ibid, FIG. 2a).

After 5 days in culture, the number of cell transfected with the empty vector was larger than the non-transfected cells.

The study also measured MIP-1α expression in vivo. Wild type, empty vector transfected, and antisense transfected ARH cell were infused intravenously into SCID mice (n=10 per group). The mice were sacrificed when they became paraplegic. Femurs and vertebrae were removed, and bone marrow plasma was obtained. Expression of hMIP-1α was measured with ELISA kits. The following table summarizes the results according to data points in Choi 2001 (ibid) FIG. 3a.

| | Wild type | Empty vector | P value |
|---|---|---|---|
| Femur | 193.33 | 591.20 | 0.042 |
| Vertebrae | 389.44 | 1031.25 | 0.059 |
| Combined | 291.39 | 786.78 | 0.012 |

Expression of hMIP-1α in mice femur was significantly higher after infusion with cells transfected with the empty vector relative mice infused with non-transfected cells. In mice vertebrae, the expression of hMIP-1α was borderline higher in mice infused with the cells transfected with the empty vector relative to mice infused with non-transfected cells. The combined data from the femur and the vertebrae shows a statistically significant effect of transfection with the empty vector on MIP-1α expression.

The pcDNA3 vector carries the cytomegalovirus (CMV) promoter. The observations demonstrate the effect of microcompetition with pcDNA3, the "empty" vector, on cell proliferation and on MIP-1α expression in vivo. Note that the pcDNA3 vector carries the cytomegalovirus (CMV) promoter.

(11) Hu 2001

Another study (Hu 2001[231]) measured the efficacy and safety of an immunoconjugate (icon) molecule, composed of a mutated mouse factor VII (mfVII) targeting domain, and the Fc effector domain of an IgG 1 Ig (mfVII/Fc icon), with the severe combined immunodeficient (SCID) mouse model of human prostatic cancer. First, the study injected the SCID mice s.c. in both rear flanks with the human prostatic cancer line c4-2.

Figure 11:
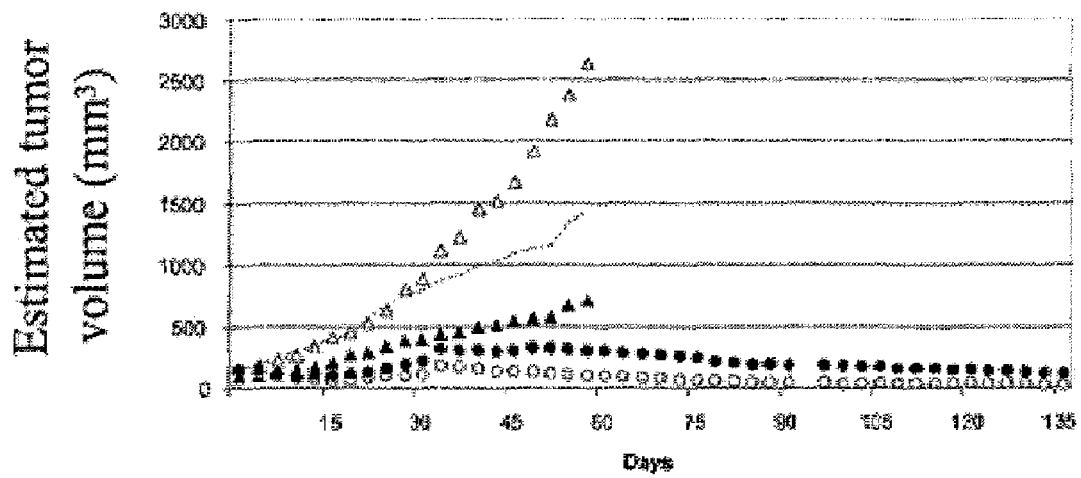
FIG. 11 shows the observed volume of tumors injected with the vector encoding the icon, volume of uninjected tumors in the icon treated mice, volume of tumors injected with the empty vector pcDNA3.1(+), and volume of uninjected tumors in the empty vector injected mice, over time, following injection of SCID mice s.c. in both rear flanks with the human prostatic cancer line c4-2.

The injection resulted in skin tumors. Then, on days 0,3,6,9,12,15,33,36,39, and 42, the study injected into the skin tumor on one flank, either the pcDNA3.1(+) vector carrying the icon (four mice), or the empty vector (four mice). The tumor on the other flank was left uninjected. The study measured tumor volume in the injected and non injected flanks. FIG. 11 presents the results (Hu 2001, ibid, FIG. 3). ○ denotes tumors injected with the vector encoding the icon, ●—uninjected tumors in the icon treated mice, Δ—tumors injected with the empty vector, ▲—uninjected tumors in the empty vector injected mice.

Figure 12:
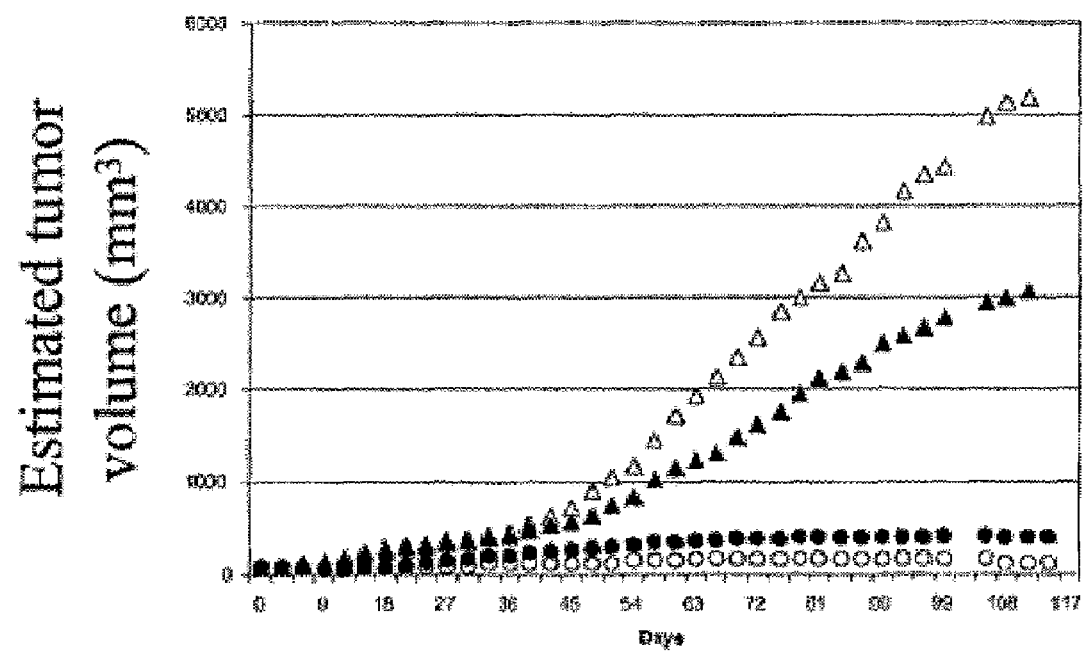
FIG. 12 shows the observed volume of tumors injected with the vector encoding the icon, volume of uninjected tumors in the icon treated mice, volume of tumors injected with the empty vector pcDNA3.1(+), and volume of uninjected tumors in the empty vector injected mice, over time, following injection of SCID mice s.c. in both rear flanks with the human melanoma line TF2.

The experiment was repeated with the human melanoma line TF2 instead of the human prostatic cancer line C4-2. The results are presented in FIG. 12 (Hu 2001, ibid, FIG. 5)

In both experiments, injection of the "empty vector" stimulated tumor growth. Compare tumors injected with empty vector (Δ) and uninjected tumors in the empty vector injected mice (▲).

c) Summary

The following table summarizes the studies above. Promoter means promoter/enhancer.

|  |  | Scholer 1984 | Mercola 1985 | Scholer 1986 | Cherington 1988 | Adam 1996 | Higgins 1996 |
|---|---|---|---|---|---|---|---|
| Viral promoter effect on cotransfected (exogenous) gene expression/activity | Viral promoter | SV40 MSV BK RSV | SV40 | SV40 |  | CMV SV40 |  |
|  | Plasmid | pSV2CAT pSV2neo pSRM2Δ | pSVCAT | pSV2neo |  | pCMV-βgal pSV-βgal |  |
|  | Gene | SV40 MSV BK RSV | murine IgH | hMT-IIA |  | PDGF-B |  |
| Viral promoter effect on cellular (endogenous) gene expression/activity | Viral promoter |  |  |  |  |  |  |
|  | Plasmid |  |  |  |  |  |  |
|  | Gene |  |  |  |  |  |  |
| Viral promoter effect on cellular function | Viral promoter |  |  |  | MMTV |  | HSV MMTV |
|  | Plasmid |  |  |  | pZIP-neo |  | HSV-neo pZIP-neo |
|  | Function |  |  |  | Cell Differentiation |  | Cell Differentiation |
| Study includes reference to effect of viral promoter (empty vector) |  | Yes (1) | Yes (2) | Yes (3) | No | Yes (4) | No |
| Study includes reference to disease |  | No | No | No | No | No | No |

|  |  | Gordeladze 1997 | Awazu 1998 | Hofman 2000 | Choi 2001 | Hu 2001 |
|---|---|---|---|---|---|---|
| Viral promoter effect on contransfected (exogenous) gene expression/activity | Viral promoter | MMTV |  | SV40 CMV |  |  |
|  | Plasmid | pZip-Neo |  | pSG5 PIRES pcDNA psV40 |  |  |
|  | Gene | HSL |  | SV40 CMV |  |  |
| Viral promoter effect on cellular (endogenous) gene expression/activity | Viral promoter |  |  |  | CMV |  |
|  | Plasmid |  |  |  | pcDNA3 |  |
|  | Gene |  |  |  | hMIP-1α |  |
| Viral promoter effect on cellular function | Viral promoter |  | SV40 |  | CMV | CMV |
|  | Plasmid |  | psV40-neo |  | pcDNA3 | pcDNA3 |
|  | Function |  | Cell growth |  | Cell growth | Tumor growth |

|  |  |  |  |  |  |
|---|---|---|---|---|---|
| Study includes reference to effect on viral promoter (empty vector) | No (5) | No (6) | Yes (7) | No (8) | No (9) |
| Study includes reference to disease | No | No | No | No | No |

References in the study to the effect of the viral promoter (empty vector):

(1) Scholer 1984: The study measured and discussed competition between different viral enhancers in contransfected studies. For instance, the study reports competition between the SV40 and MSV enhancers. The competition between viral enhancers was also observed in Hofman 2000 (see above). The study includes no discussion relating the effect of such competition with endogenous gene expression, cellular function, and disease.

(2) Mercola 1985: The study measured and discussed competition between SV40 enhancer and the cotransfected Ig H enhancer. The study includes no discussion relating the effect of such competition with endogenous gene expression, cellular function, and disease.

(3) Scholer 1986 (ibid): The study measured and discussed competition between SV40 enhancer and the cotransfected hMT-IIA promoter. The study includes no discussion relating the effect of such competition with endogenous gene expression, cellular function, and disease.

(4) Adam 1996 (ibid): The study measured and discussed microcompetition between the CMV and SV40 promoter/enhancer and the cotransfected PDGF-B promoter/enhancer. Based on the observations, the study concluded that "Of more general interest, these results indicate that care should be exercised when using commonly available reporter gene constructs to standardize transfection efficiencies. It is possible that the importance of some potential gene regulatory sequences could be under estimated, or overlooked entirely, given certain combinations of reference plasmid co-transfection conditions and cell-types. Moreover, "The results we present here indicate a warning note for the use of co-transfected reference plasmids under the control of viral enhancers: Initial calibration experiments to determine the appropriate reference plasmid and the optimal relative molar concentration may be worthwhile in order to avoid erroneous interoperations of such transfection data." The authors interpret the data in the narrow context of laboratory techniques, specifically, reference plasmids. No relation is suggested between microcompetition, endogenous gene expression, cellular function, or disease.

(5) Gordeladze 1997 (ibid): The only reference to the difference between pre-differentiated and post-differentiated 3T3-L1 cells transfected with the pZipNeo "empty vector" is the following sentence: "However, post-differentiated vector transfected cells exhibited a non-significant alteration compared to corresponding pre-differentiated cells." Note that, although the authors used the term "non-significant alteration," the paper reports no quantitative analysis of the blot in FIG. 11, and specifically, no statistical analysis that can justify the use of the term "significant." Contrary to the authors conclusion, a visual inspection of the blot in FIG. 11 shows a decline of HSL mRNA in the post-differentiated compared to the pre-differentiated cells transfected with the empty vector.

(6) Awazu 1998: The study does not compare between nontransfected (HuH-7 wild) and empty vector transfected (HuH-7 neo) cells. It is interesting that the study called both the "HuH-7 wild" and "HuH-7 neo" the nontransfected cells. In particular, the study does not mention a relation between microcompetition, endogenous gene expression, cellular function, or disease.

(7) Hofman 2000 (ibid): Measured competition between different viral enhancers in cotransfected experiments. In the discussion the authors remark that "Whether this competition occurs at the level of transcription initiation or at a later step is not clear." Moreover, based on the observations, the study concluded that "Moreover, it is recommended to limit the amount of (co)transfected expression plasmid and to avoid the use of empty expression plasmid as a control. Finally, one should be aware of similar misleading results in other experimental set-ups base on cotransfection." Similar to Adam 1996 (see above), the authors interpret the data in the narrow context of laboratory set-ups, specifically, the use of empty vectors as controls in cotransfection studies. No relation is suggested between the observed microcompetition, endogenous gene expression, cellular function, or disease.

(8) Choi 2001: The study includes comparisons between antisense transfected cells and either empty vector transfected cells or wild type cells as controls. The study does not include a comparison between the empty vector transfected and the wild type cells, that is, between the two "controls."

(9) Hu 2001: The study does not compare between the tumors injected with the control (empty) vector and the uninjected tumors in control mice. The only reference to the effect of the empty vector as reported in FIGS. 3 and 5 is the following sentence: "In mice injected with the control vector, the tumors on both flanks grew continuously, and the mice died or had to be euthanized by day 57."

Conclusion: these studies demonstrate the commitment of the research community to the "protein-dependent" paradigm. Each study used two types of plasmids, one with a gene of interest, for instance, cellular Rb or viral T antigen, an another with a reporter gene under control of a viral promoter/enhancer. The second plasmid was considered "empty," and was, therefore, used as control. All studies above report observations which clearly show a significant effect of the "empty" plasmid on gene expression, cell cycle progression, cell proliferation or cell differentiation. However, some of these studies include no reference to these observation, the observations are completely ignored. Moreover, even the studies which discuss the effect of the empty vector, miss the relation between microcompetition and disease.

2. Aberrant Transcription and Disease a) Introduction

It is a well known fact that aberrant transcription, resulting from, for instance, a mutation or hypermethylation, may result in disease. Consider, for instance, the Online Mendelian Inheritance in Man (OMIM™) database which catalogs specific mutations and their association with genetic disorders. The following examples demonstrate the effect of controlled mutation in three specific genes, MT, PDGF-B, and HSL on the subject health.

b) Examples (1) MT-I or MT-II Deficiency and Disease (Weight Gain)

Mice with mutated MT-I and MT-II genes are apparently phenotypically normal, despite reduced expression of the metallothionein genes. The disruption shows no adverse effect on their ability to reproduce and rear offspring. However, after weaning, MT-null mice consume more food and gain weight at a higher rate compared to controls. The majority of adult male mice in the MT-null colony showed moderate obesity (Beattie 1998[232]). Lead treated MT-null mice showed dose-related nephromegaly, and following exposure, reduced renal function compared to wild type (Qu 2002[233]). MT-I+II knock out (MTKO) mice showed higher susceptibility to autoimmune encephalomyelitis (EAE) compared to wild type (Penkowa 2001[234]), and increased susceptibility to the immunosuppresseive effects of ultraviolet B radiation and cis-urocanic acid (Reeve 2000[235]). MT-I/II null mice also showed increased liver and kidney damage following chronic exposure to inorganic arsenicals (Liu 2000[236]).

(2) PDGF-B Deficiency and Disease

In mice, a PDGF-B deficiency is embryonic lethal and is associated with cardiovascular, renal, placental and hematological disorders. Specifically, mice show formation of hemorrhage, microaneurysm, and microvessel leakage. The mice also show lack of kidney glomerular mesangial cells and microvascular pericytes, and reduced or complete loss of vascular smooth muscle cells (SMC) around small and medium sized arteries.

The mice also show dilated heart and aorta, anemia and thrombocytopenia (Kaminski 2001[237], Lindahl 1997[238]).

(3) HSL Deficiency and Disease (Adipocyte Hypertrophy)

HSL knockout mice were generated by homologous recombination in embryonic stem cells. Cholesterol ester hydrolase (NCEH) activities were completely absent from both brown adipose tissue (BAT) and white adipose tissue (WAT) in mice homozygous for the mutant HSL allele (HSL-/-). The cytoplasmic area of BAT adipocytes was increased 5-fold in HSL-/- mice (Osuga 2000[239], FIG. 3a) and the median cytoplasmic areas in WAT was enlarged 2-fold (Ibid, FIG. 3b). The HSL knockout mice showed adipocyte hypertrophy. HSL-deficient mice are normoglycemic and normoinsulinemic under basal conditions. However, after overnight fast, the mice showed reduce concentration of circulating free fatty acids (FFAs) relative to control and heterozygous mice. Moreover, an intraperitoneal glucose tolerance test of the HSL-null mice revealed insulin resistance (Roduit 2001[240]). HSL-deficient male mice are infertile (Chung 2001[241]). HSL-deficient mice also showed other defects associated with mobilization of triglycerides (TG), diglycerides (DG) and cholesteryl esters (Haernmerle 2002A[242], Haemmerle 2002B[243]).

c) Summary

Microcompetition between a foreign polynucleotide and a cellular gene for a limiting transcription complex result in aberrant transcription of the cellular gene. Aberrant transcription results in disease. Therefore, microcompetition between a foreign polynucleotide and a cellular gene for a limiting transcription complex results in disease. When the foreign polynucleotide persists in the host cell for an extended period of time, microcompetition between the foreign polynucleotide and the cellular gene results in a chronic disease.

3. Limiting Transcription Factors a) Examples

The coactivator p300 is a 2,414-amino acid protein initially identified as a binding target of the E1A oncoprotein. cbp is a 2,441-amino acid protein initially identified as a transcriptional activator bound to phosphorylated cAMP response element (CREB) binding protein (hence, cbp). p300 and cbp share 91% sequence identity and are functionally equivalent. Both p300 and cbp are members of a family of proteins collectively referred to as p300/cbp.

Although p300/cbp are widely expressed, their cellular availability is limited. Several studies demonstrated inhibited activation of certain transcription factors resulting from competitive binding of p300/cbp to other cellular or viral proteins. For example, competitive binding of p300 or CBP to the glucocorticoid receptor (GR), or retinoic acid receptor (RAR), inhibited activation of a promoter dependent on the AP-1 transcription factor (Kamei 1996[244]). Competitive binding of cbp to STAT1α inhibited activation of a promoter dependent on both the AP-1 and ets transcription factors (Horvai 1997[245]). Competitive binding of p300 to STAT2 inhibited activation of a promoter dependent on the NF-κB RelA transcription factor (Hottiger 1998[246]). Other studies also demonstrated limited availability of p300/cbp, see, for instance, Pise-Masison 2001[247], Banas 2001[248], Wang 2001[249], Ernst 2001[250], Yuan 2001[251], Ghosh 2001[252], Li 2000[253], Nagarajan 2000[254], Speir 2000[255], Chen 2000[256], and Werner 2000[257].

4. Transcription Factors Microcompeted by Foreign Polynucleotides a) Examples

One example of a foreign polynucleotide typically found in host cells is viral DNA. Several cellular transcription factors form complexes on viral DNA, and transactivate or suppress viral transcription. Consider GA binding protein (GABP), also called Nuclear Respiratory Factor 2 (NRF-2)[258], E4 Transcription factor 1 (E4TF1)[259], and Enhancer Factor 1A (EF-1A)[260], as an example. The literature lists five subunits of GABP: GABPα, GABPβ1, GABPβ2 (together called GABPβ), GABPγ1 and GABPγ2 (together called GABPγ). GABPα is an ets-related DNA-binding protein which binds the DNA motif (A/C)GGA(A/T)(G/A), termed the N-box. GABPα forms a heterocomplex with GABPβ which stimulates transcription efficiently both in vitro and in vivo. GABPα also forms a heterocomplex with GABPγ, but the heterodimer does not stimulate transcription. The degree of transactivation by GABP appears to correlate with the relative intracellular concentrations of GABPβ and GABPγ. An increase in GABPβ relative to GABPγ increases transcription, while an increase of GABPγ relative to GABPβ decreases transcription. The degree of transactivation by GABP is, therefore, a function of the ratio between GABPβ and GABPγ. Control of this ratio within the cell regulates transcription of genes with binding sites for GABP (Suzuki 1998[261]).

The N-box is the core binding sequence of many viral enhancers including the polyomavirus enhancer area 3

(PEA3) (Asano 1990[262]), adenovirus E1A enhancer (Higashino 1993[263]), Rous Sarcoma Virus (RSV) enhancer (Laimins 1984[264]), Herpes Simplex Virus 1 (HSV-1) (in the promoter of the immediate early gene ICP4) (LaMarco 1989[265], Douville 1995[266]), Cytomegalovirus (CMV) (IE-1 enhancer/promoter region) (Boshart 1985[267]), Moloney Murine Leukemia Virus (Mo-MuLV) enhancer (Gunther 1994[268]), Human Immunodeficiency Virus (HIV) (the two NF-κB binding motifs in the HIV LTR) (Flory 1996[269]), Epstein-Barr virus (EBV) (20 copies of the N-box in the +7421/+8042 oriP/enhancer) (Rawlins 1985[270]) and Human T-cell lymphotropic virus (HTLV) (8 N-boxes in the enhancer (Mauclere 1995[271]) and one N-box in the LTR (Kornfeld 1987[272])). Note that some viral enhancers, for example SV40, lack a precise N-box, but still bind the GABP transcription factor (Bannert 1999[273]).

Ample evidence exists supporting binding of GABP to the N-boxes in these viral enhancers. For instance, Flory, et al., (1996[274]) showed binding of GABP to the HIV LTR, Douville, et al., (1995[275]) showed binding of GABP to the promoter of ICP4 of HSV-1, Bruder, et al., (1991[276]) and Bruder, et al., (1989[277]) showed binding of GABP to the adenovirus E1A enhancer element I, Ostapehuk, et al., (1986[278]) showed binding of GABP (called EF-1A in their paper) to the polyomavirus enhancer and Gunther, et al., (1994[279]) showed binding of GABP to Mo-MuLV. Other studies demonstrate competition between the above viral enhancers and enhancers of other viruses. Scholer and Gruss, (1984[280]) showed competition between the Moloney Sarcoma Virus (MSV) enhancer and SV40 enhancer and competition between the RSV enhancer and the BK virus enhancer.

Other cellular transcription factors also form complexes on viral DNA, and transactivate or suppress viral transcription. For instance, AML1 binds the polyomavirus (Chen 1998[281]), Mo-MLV (Lewis 1999[282], Sun 1995[283]), and SL3 retrovirus (Martiney 1999A[284], Martiney 1999B[285]), NF-AT binds HIV-1 (NFAT1 binds the NF-κB site in the viral LTR) (Cron 2000[286]), HNF4α binds the Hepatitis B virus (Wang 1998[287]), the Smad3/Smad4 complex binds the Epstein-Barr virus (Liang 2000[288]), ets1 binds the human cytomegalovirus (Chen 2000[289]), NF-YB binds the human cytomegalovirus (Huang 1994[290]), hepatitis B virus (Lu 1996[291], Bock 1999[292]), minute virus (Gu 1995[293]), adenovirus (Song 1998[294]), and varicella-zoster virus (Moriuchi 1995[295]), ATF-2 binds the human T-cell leukemia type 1 (HTLV-1) (Xu 1996[296], Xu 1994[297]), and hepatitis B virus (Choi 1997[298]), p53 binds the polyomavirus (Py) (Kanda 1994[299]), human CMV (Allamane 2001[300], Deb 2001[301]), human immunodeficiency virus type 1 (HIV-1) (Deb 2001, ibid), and the Hepatitis B virus (Lee 1998[302], Ori 1998[303]), YY-1 binds the human papillomavirus type 18 (HPV-18) (Jundt 1995[304]), NF-kB binds HIV (Hottiger 1998, ibid), Stat2 binds HIV (Hottiger 1998, ibid), and C/EBPβ binds the Hepatitis B virus (Lai 1999[305], Gilbert 2000[306]), and HIV-1 (LTR) (Honda 1998[307]), and the glucocorticoid receptor (GR) binds the mouse mammary tumor virus LTR (Pfitzner 1998, ibid).

Note that all the above mentioned transcription factors bind the limiting coactivator p300/cbp (Bannert 1999[308], Kitabayashi 1998[309], Garcia-Rodriguez 1998[310], Sisk 2000[311], Soutoglou 2000[312], Janknecht 1998[313], Feng 1998[314], Pouponnot 1998[315], Jayaraman 1999[316], Li 1998[317], Duyndam 1999[318], Avantaggiati 1999[319] Van Order 1999[320], Hottiger 1998[321], Gerritsen 1997[322], Hottiger 1998, ibid, Paulson 1999, ibid, Gringras 1999, ibid, Bhattacharya 1996[323], Mink 1997[324], Pfitzner 1998, ibid).

Since p300/cbp is limiting, a transcription complex that includes p300/cbp is also limiting. For instance, since p300/cbp is limiting, GABP•p300/cbp is also limiting.

I claim:

1. A method for evaluating the effectiveness of a compound for use in modulating the progression of a chronic disease, the method comprising the steps of:
   (a) selecting a polynucleotide, wherein said polynucleotide is natural to a certain first organism, and wherein said polynucleotide is empty in respect to said first organism, and wherein said polynucleotide is foreign to a second organism;
   (b) introducing or identifying said polynucleotide in a cell of said second organism;
   (c) contacting said cell with said compound;
   (d) assaying microcompetition between said foreign polynucleotide and another polynucleotide;
   (e) detecting a change in said microcompetition, wherein said change is indicative of the effectiveness of said compound in modulating the progression of said chronic disease.

2. The method in claim 1, wherein said other polynucleotide is a polynucleotide natural to said cell.

3. The method as of one of claims 1 or 2, wherein said compound is foreign to said both organisms.

4. The method in claim 2, wherein said compound is a synthetic compound.

5. The method as of one of claims 1 or 2, wherein said introducing is by changing the copy number of a polynucleotide in the cell.

6. The method as of one of claims 1 or 2, wherein said introducing is by transfecting the cell with a polynucleotide.

7. The method as of one of claims 1 or 2, wherein said introducing is by infecting the cell with a virus, active or deactivated.

8. The method as of one of claims 1 or 2, wherein said introducing is by chemically modifying a polynucleotide in the cell.

9. The method as of one of claims 1 or 2, wherein said introducing is by mutating a polynucleotide in the cell.

10. The method as of one of claims 1 or 2, wherein said introducing is by modifying the binding affinity or avidity of a polynucleotide in the cell.

11. The method as of one of claims 1 or 2, wherein said cell is an animal or human cell.

12. The method as of one of claims 1 or 2, wherein said foreign polynucleotide is a viral polynucleotide.

13. The method as of one of claims 1 or 2, wherein said foreign polynucleotide is a viral regulatory element.

14. The method as of one of claims 1 or 2, wherein said assaying microcompetition is assaying formation of a complex between a transcription complex natural to said cell and said foreign polynucleotide.

15. The method as of one of claims 1 or 2, wherein said assaying microcompetition is assaying expression of a gene, or gene fragment, where said gene is under the control of said foreign polynucleotide.

16. The method as of one of claims 1 or 2, wherein said assaying microcompetition is assaying activity of a gene product of a gene, or gene fragment, where said gene is under the control of said foreign polynucleotide.

17. The method as of one of claims 1 or 2, wherein said assaying microcompetition is assaying formation of a complex between a transcription complex natural to said cell and said other polynucleotide.

18. The method as of one of claims 1 or 2, wherein said assaying microcompetition is assaying expression of a gene, or gene fragment, wherein said gene is under the control of said other polynucleotide.

19. The method as of one of claims 1 or 2, wherein said assaying microcompetition is assaying activity of a gene product of a gene, or gene fragment, wherein said gene is under the control of said other polynucleotide.

20. The method as of one of claims 1 or 2, wherein said assaying microcompetition is assaying the copy number of said foreign polynucleotide.

21. The method as of one of claims 1 or 2, wherein said evaluating the effectiveness of a compound for use in modulating the progression of a chronic disease is evaluating the effectiveness of a compound for use in stimulating or inhibiting the progression of a chronic disease.

22. The method as of one of claims 1 or 2, wherein said changes in microcompetition include increase or decrease in microcompetition.

23. A method for evaluating the effectiveness of a compound for use in inhibiting the progression of a chronic disease, comprising:
    (a) selecting a cell;
    (b) introducing or identifying a polynucleotide foreign to said cell in said cell;
    (c) contacting said cell with said compound;
    (d) assaying microcompetition between said foreign polynucleotide and another polynucleotide;
    (e) detecting a decrease in said microcompetition, wherein said decrease is indicative of the effectiveness of said compound in inhibiting the progression of said chronic disease.

24. A method for evaluating the effectiveness of a compound for use in modulating the progression of a chronic disease, comprising:
    (a) selecting a polynucleotide wherein said polynucleotide is natural to a certain first organism, wherein said polynucleotide expresses at least one polypeptide, wherein said polypeptide is inactive in a cell of a second organism, and wherein said polynucleotide is foreign to said second organism;
    (b) introducing or identifying said polynucleotide in said cell of said second organism;
    (c) contacting said cell with said compound;
    (d) assaying microcompetition between said foreign polynucleotide and a another polynucleotide;
    (e) detecting a change in said microcompetition, wherein said change is indicative of the effectiveness of said compound in modulating the progression of said chronic disease.

25. A method for evaluating the effectiveness of a compound for use in modulating the progression of a chronic disease, comprising:
    (a) selecting a cell;
    (b) introducing or identifying a polynucleotide in said cell, wherein said polynucleotide is foreign to said cell, wherein said polynucleotide and another polynucleotide natural to said cell microcompete for a transcription factor or complex, and wherein said factor or complex is limiting in said cell in respect to the natural polynucleotide;
    (c) contacting said cell with said compound;
    (d) assaying said microcompetition between said polynucleotides;
    (e) detecting a change in said microcompetition, wherein said change is indicative of the effectiveness of said compound in modulating the progression of said chronic disease.

26. A method for evaluating the effectiveness of a compound for use in modulating the progression of a chronic disease, comprising:
    (a) selecting a polynucleotide wherein said polynucleotide is natural to a certain first organism, wherein said polynucleotide is empty in respect to said first organism, wherein said polynucleotide is foreign to a second organism, wherein said polynucleotide and another polynucleotide natural to said second organism microcompetes for a transcription factor or complex;
    (b) introducing or identifying said foreign polynucleotide in a cell of said second organism, wherein said factor or complex is limiting in said cell in respect to the natural polynucleotide;
    (c) contacting said cell with said compound;
    (c) assaying said microcompetition between said polynucleotides;
    (d) detecting a change in said microcompetition, wherein said change is indicative of the effectiveness of said compound in modulating the progression of said chronic disease.

27. The method in claim 23, wherein said other polynucleotide is a polynucleotide natural to said cell.

28. The method in claim 24, wherein said other polynucleotide is a polynucleotide natural to said cell.

29. The method as in one of claims 23-28, wherein said assaying microcompetition is assaying formation of a complex between a transcription complex natural to said cell and said foreign polynucleotide.

30. The method as in one of claims 23-28, wherein said assaying microcompetition is assaying the expression of a gene, or gene fragment, where said gene is under the control of said foreign polynucleotide.

31. The method as in one of claims 23-28, wherein said assaying microcompetition is assaying activity of a gene product of a gene, or gene fragment, where said gene is under the control of said foreign polynucleotide.

32. The method as in one of claims 23-28, wherein said assaying microcompetition is assaying formation of a complex between a transcription complex natural to said cell and said other polynucleotide.

33. The method as in one of claims 23-28, wherein said assaying microcompetition is assaying expression of a gene, or gene fragment, where said gene is under the control of said other polynucleotide.

34. The method as in one of claims 23-28, wherein said assaying microcompetition is assaying activity of a gene product of a gene, or gene fragment, where said gene is under the control of said other polynucleotide.

35. The method as in one of claims 23-28, wherein said assaying microcompetition is assaying copy number of said foreign polynucleotide.

36. The method as in one of claims 23-28, wherein said evaluating the effectiveness of a compound for use in modulating the progression of a chronic disease is evaluating the effectiveness of a compound for use in stimulating or inhibiting the progression of a chronic disease.

37. The method as in one of claims 24-26, wherein said changes in microcompetition include decrease or increase in microcompetition.

38. The method in claim 24, wherein all polypeptides expressed by said foreign polynucleotide are inactive in said cell.

39. The method of claim 24, wherein said polypeptide is rendered inactive by contacting said polypeptide with inhibitors.

40. The method of claim 38, wherein said polypeptides are rendered inactive by contacting said polypeptides with inhibitors.

41. A method for evaluating the effectiveness of a compound for use in modulating the progression of a chronic disease, comprising:
(a) selecting a cell;
(b) introducing or identifying a polynucleotide in said cell, wherein said polynucleotide is foreign to said cell, and wherein said foreign polynucleotide microcompetes with a polynucleotide natural to said cell;
(c) contacting said cell with said compound;
(d) assaying the activity of said natural polynucleotide;
(e) detecting a change in said activity, wherein said change is indicative of the effectiveness of said compound in modulating the progression of said chronic disease.

42. A method for evaluating the effectiveness of a compound for use in modulating the progression of a chronic disease, comprising:
(a) selecting a cell;
(b) introducing or identifying polynucleotides in said cell, wherein at least two of said polynucleotides are foreign to said cell, wherein said foreign polynucleotides can microcompete, wherein one polynucleotide is natural to a second cell, and wherein the second polynucleotide is natural to an organism which can infect said second cell;
(c) contacting said cell with said compound;
(d) assaying the activity of said polynucleotide natural to said second cell;
(e) detecting a change in said activity, wherein said change is indicative of the effectiveness of said compound in modulating the progression of said chronic disease.

43. The method of claim 41, wherein said microcompetition is for a transcription factor or complex, wherein said factor or complex is limiting in said cell in respect to the natural polynucleotide.

44. The method of claim 42, wherein said microcompetition is for a transcription factor or complex, wherein said factor or complex is limiting in said selected cell in respect to at least one of the foreign polynucleotide.

45. The method of claim 41, wherein said foreign polynucleotide is empty.

46. The method of claim 42, wherein said polynucleotide natural to said infectious organism is empty.

47. The method of claim 41, wherein the foreign polynucleotide expresses at least one polypeptide in said cell, and wherein said polypeptide is inactive in said cell.

48. The method of claim 42, wherein at least one of said foreign polynucleotides expresses at least one polypeptide in said selected cell, and wherein said polypeptide is inactive in said selected cell.

49. The method of claim 41, wherein all polypeptides expressed by the foreign polynucleotide in said cell are inactive in said cell.

50. The method of claim 42, wherein all polypeptides expressed in said selected cell by the polynucleotide natural to said infectious organism and/or the polynucleotide natural to said second cell are inactive in said selected cell.

51. The method as in one of the claims 41-50, wherein said activity is formation of a complex on said polynucleotide.

52. The method as in one of the claims 41-50, wherein said activity is expression of a gene, or gene fragment, wherein said gene is under the control of said polynucleotide(s).

53. The method as in one of the claims 23-28, 41-42, wherein said introducing is by changing the copy number of a polynucleotide in the cell.

54. The method as in one of the claims 23-28, 41-42, wherein said introducing is by transfecting the cell with a polynucleotide.

55. The method as in one of the claims 23-28, 41-42, wherein said introducing is by infecting the cell with a virus, active or deactivated.

56. The method as in one of the claims 23-28, 41-42, wherein said introducing is by chemically modifying a polynucleotide in the cell.

57. The method as in one of the claims 23-28, 41-42, wherein said introducing is by mutating a polynucleotide in the cell.

58. The method as in one of the claims 23-28, 41-42, wherein said introducing is by modifying the binding affinity or avidity of a polynucleotide in the cell.

59. The method as in one of the claims 1, 23-28, 41-42, wherein said identifying is by finding in said cell a mutated polynucleotide otherwise natural to said cell.

60. The method as in one of the claims 23-28, 41-42, wherein said cell is an animal or human cell.

61. The method as in one of the claims 23-28, 41-42, wherein said foreign polynucleotide is a viral polynucleotide.

62. The method as in one of the claims 23-28, 41-42, wherein said foreign polynucleotide is a viral regulatory element.

63. A method for monitoring the efficacy of a treatment in clinical trials for treating a chronic disease in an animal or human subject, comprising:
(a) administrating said treatment to said subject;
(b) assaying microcompetition between a polynucleotide natural to said subject and a polynucleotide foreign to said subject;
(c) detecting a change in said microcompetition, wherein said change is indicative of the efficacy of said treatment.

64. The method in claim 63, wherein said foreign polynucleotide is latent in said subject.

65. The method in claim 63, wherein said assaying microcompetition is assaying the activity of said foreign polynucleotide.

66. The method in claim 63, wherein said assaying microcompetition is assaying the copy number of said foreign polynucleotide.

67. The method in claim 63, wherein said assaying microcompetition is assaying the activity of said natural polynucleotide.

68. The method according to claim 65 or 67, wherein said activity is formation of a transcription complex on said polynucleotide.

69. The method according to claim 65 or 67, wherein said activity is expression of a gene, or gene fragment, wherein said gene is under the control of said polynucleotide.

70. A method for evaluating the effectiveness of a compound for use in modulating microcompetition between polynucleotides, comprising:
(a) introducing andior identifying said polynucleotides in a cell;
(b) assaying microcompetition between said polynucleotides;

(c) contacting said cell with said compound;

(d) assaying microcompetition between said polynucleotides following said contact;

(e) detecting a change in said microcompetition, wherein said change is indicative of the effectiveness of said compound in modulating microcompetition between said polynucleotides.

71. The method of claim 70, wherein at least one polynucleotide is foreign to said cell and at least one polynucleotide is natural to said cell.

72. The method of claim 70, wherein said polynucleotides are foreign to said cell.

73. The method of claim 70, wherein said polynucleotides are natural to said cell.

74. The method as of one of claims 70-73, wherein said introducing is by changing the copy number of a polynucleotide in the cell.

75. The method as of one of claims 70-73, wherein said introducing is by transfecting the cell with a polynucleotide.

76. The method as of one of claims 70-73, wherein said introducing is by infecting the cell with a virus, active or deactivated.

77. The method as of one of claims 70-73, wherein said introducing is by chemically modifying a polynucleotide in the cell.

78. The method as of one of claims 70-73, wherein said introducing is by mutating a polynucleotide in the cell.

79. The method as of one of claims 70-73, wherein said introducing is by modifying the binding affinity or avidity of a polynucleotide in the cell.

80. The method as of one of claims 70-73, wherein said cell is an animal or human cell.

81. The method as of one of claims 71, 72, wherein said foreign polynucleotide(s) is a viral polynucleotide.

82. The method as of one of claims 71, 72, wherein said foreign polynucleotide(s) is a viral regulatory element.

83. The method as of one of claims 71, 72, wherein said assaying microcompetition is assaying formation of a complex between a transcription complex natural to said cell and said foreign polynucleotide(s).

84. The method as of one of claims 71, 72, wherein said assaying microcompetition is assaying expression of a gene, or gene fragment, where said gene is under the control of said foreign polynucleotide(s).

85. The method as of one of claims 71, 72, wherein said assaying microcompetition is assaying activity of a gene product of a gene, or gene fragment, where said gene is under the control of said foreign polynucleotide(s).

86. The method as of one of claims 71, 73, wherein said assaying microcompetition is assaying formation of a complex between a transcription complex natural to said cell and said polynucleotide(s) natural to said cell.

87. The method as of one of claims 71, 73, wherein said assaying microcompetition is assaying expression of a gene, or gene fragment, where said gene is under the control of said polynucleotide(s) natural to said cell.

88. The method as of one of claims 71, 73, wherein said assaying microcompetition is assaying activity of a gene product of a gene, or gene fragment, where said gene is under the control of said polynucleotide(s) natural to said cell.

89. The method as of one of claims 71, 72, wherein said assaying microcompetition is assaying copy number of said foreign polynucleotide(s).

90. The method as of one of claims 70-73, wherein said changes in microcompetition include increase or decrease in microcompetition.

91. The method as in one of claims 71, 72, wherein said identifying a foreign polynucleotide is by finding in said cell a mutated polynucleotide otherwise natural to said cell.

92. A method for monitoring the efficacy of a treatment in clinical trials for treating a chronic disease in anammal or human subject, comprising:

(a) selecting a treatment that can affect microcompetition between a polynucleotide natural to said subject and a polynucleotide foreign to said subject;

(b) administrating said treatment to said subject;

(c) assaying the progression of said disease;

(d) detecting a change in said progression, wherein said change is indicative of the efficacy of said treatment.

93. A method for monitoring the efficacy of a treatment in clinical trials for treating a chronic disease in an animal or human subject, comprising:

(a) selecting a treatment that can affect microcompetition between a polynucleotide natural to said subject and a polynucleotide foreign to said subject;

(b) administrating to said subject another treatment, wherein said other treatment can induce latency, or latency-like behavior of said foreign polynucleotide in said subject;

(c) administrating to said subject the treatment that can affect said microcompetition, wherein said administration is done before, after, or during the administration of said other treatment;

(d) assaying the progression of said disease;

(e) detecting a change in said progression, wherein said change is indicative of the efficacy of said treatment.

94. The method in claim 92, wherein said foreign polynucleotide is latent in said subject.

95. The method as in one of the claims 64, 92, 93, 94, wherein said microcompetition is for a transcription factor or complex, wherein said factor or complex is limiting in at least one animal or human cell type in respect to the natural polynucleotide.

* * * * *